(12) United States Patent
Badylak et al.

(10) Patent No.: US 11,291,688 B2
(45) Date of Patent: Apr. 5, 2022

(54) EXTRACELLULAR MATRIX (ECM) HYDROGEL AND SOLUBLE FRACTION THEREOF FOR THE TREATMENT OF CANCER

(71) Applicant: University of Pittsburgh-Of the Commonwealth System of Higher Education, Pittsburgh, PA (US)

(72) Inventors: Stephen Francis Badylak, West Lafayette, IN (US); George S. Hussey, Cranberry Township, PA (US); Lindsey Tamiko Saldin, El Segundo, CA (US); Mark Hikaru Murdock, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 31 days.

(21) Appl. No.: 16/490,056

(22) PCT Filed: Mar. 2, 2018

(86) PCT No.: PCT/US2018/020764
§ 371 (c)(1),
(2) Date: Aug. 29, 2019

(87) PCT Pub. No.: WO2018/161034
PCT Pub. Date: Sep. 7, 2018

(65) Prior Publication Data
US 2020/0069738 A1 Mar. 5, 2020

Related U.S. Application Data

(60) Provisional application No. 62/465,988, filed on Mar. 2, 2017.

(51) Int. Cl.
*A61P 35/00* (2006.01)
*A61K 35/22* (2015.01)
*A61K 35/37* (2015.01)
*A61K 45/06* (2006.01)

(52) U.S. Cl.
CPC .............. *A61K 35/22* (2013.01); *A61K 35/37* (2013.01); *A61K 45/06* (2013.01); *A61P 35/00* (2018.01)

(58) Field of Classification Search
None
See application file for complete search history.

(56) References Cited

U.S. PATENT DOCUMENTS

| | | |
|---|---|---|
| 4,582,640 A | 4/1986 | Smestad et al. |
| 4,902,508 A | 2/1990 | Badylak et al. |
| 4,956,178 A | 9/1990 | Badylak et al. |
| 4,970,298 A | 11/1990 | Silver et al. |
| 4,978,668 A | 12/1990 | Babbs et al. |
| 5,007,927 A | 4/1991 | Badylak et al. |
| 5,275,826 A | 1/1994 | Badylak et al. |
| 5,281,422 A | 1/1994 | Badylak et al. |
| 5,352,463 A | 10/1994 | Badylak et al. |
| 5,354,274 A | 10/1994 | Demeter et al. |
| 5,372,821 A | 12/1994 | Badylak et al. |
| 5,445,833 A | 8/1995 | Badylak et al. |
| 5,516,533 A | 5/1996 | Badylak et al. |
| 5,554,389 A | 9/1996 | Badylak et al. |
| 5,573,784 A | 11/1996 | Badylak et al. |
| 5,641,518 A | 6/1997 | Badylak et al. |
| 5,645,860 A | 7/1997 | Knapp, Jr. et al. |
| 5,658,594 A | 8/1997 | Al-Hassan |
| 5,695,998 A | 12/1997 | Badylak et al. |
| 5,700,486 A | 12/1997 | Canal et al. |
| 5,711,969 A | 1/1998 | Patel et al. |
| 5,753,267 A | 5/1998 | Badylak et al. |
| 5,755,791 A | 5/1998 | Whitson et al. |
| 5,762,966 A | 6/1998 | Knapp, Jr. et al. |

(Continued)

FOREIGN PATENT DOCUMENTS

| | | |
|---|---|---|
| WO | WO2010/056378 | 5/2010 |
| WO | WO 2010/056378 A2 | 5/2010 |

(Continued)

OTHER PUBLICATIONS

Badylak, "Esophageal tissue engineering," McGowan Institute for Regenerative Medicine, hhttp://www.mirm.pitt.edu/Badylak/projects/Esophageal_Tissue_Engineering.asp, 3 pages (printed to PDF on Dec. 21, 2016).

Hinderer et al., "ECM and ECM-like materials—Biomaterials for applications in regenerative medicine and cancer therapy," *Advanced Drug Delivery Reviews* 97: 260-269 (Epub Dec. 3, 2015).

(Continued)

*Primary Examiner* — Qiuwen Mi
(74) *Attorney, Agent, or Firm* — Klarquist Sparkman, LLP

(57) ABSTRACT

Methods are disclosed for reducing the proliferation of a tumor cell, increasing apoptosis of a tumor cell, and/or decreasing migration of a tumor cell. These methods include contacting the tumor cell with an effective amount of solubilized ECM or a soluble fraction of extracellular matrix (ECM), thereby reducing the proliferation of the tumor cell, increasing apoptosis of the tumor cell, and/or decreasing migration of the tumor cell. Methods are also disclosed for treating a subject with a tumor. The methods include administering to the subject a therapeutically effective amount of a pharmaceutical composition comprising a soluble fraction of an ECM and a pharmaceutically acceptable carrier, thereby treating the tumor in the subject. In specific non-limiting examples, the tumor is a glioma and/or the ECM hydrogel is a urinary bladder ECM hydrogel.

22 Claims, 30 Drawing Sheets

(56) References Cited

U.S. PATENT DOCUMENTS

| | | |
|---|---|---|
| 5,800,537 A | 9/1998 | Bell |
| 5,866,414 A | 2/1999 | Badylak et al. |
| 5,885,619 A | 3/1999 | Patel et al. |
| 5,955,110 A | 9/1999 | Patel et al. |
| 5,968,096 A | 10/1999 | Whitson et al. |
| 5,997,575 A | 12/1999 | Whitson et al. |
| 6,087,157 A | 7/2000 | Badylak et al. |
| 6,096,347 A | 8/2000 | Geddes et al. |
| 6,099,567 A | 8/2000 | Badylak et al. |
| 6,126,686 A | 10/2000 | Badylak et al. |
| 6,187,039 B1 | 2/2001 | Hiles et al. |
| 6,241,981 B1 | 6/2001 | Cobb et al. |
| 6,264,992 B1 | 7/2001 | Voytik-Harbin et al. |
| 6,331,319 B1 | 12/2001 | Badylak et al. |
| 6,375,989 B1 | 4/2002 | Badylak et al. |
| 6,379,710 B1 | 4/2002 | Badylak et al. |
| 6,444,229 B2 | 9/2002 | Voytik-Harbin et al. |
| 6,448,076 B2 | 9/2002 | Dennis et al. |
| 6,475,232 B1 | 11/2002 | Babbs et al. |
| 6,485,723 B1 | 11/2002 | Badylak et al. |
| 6,576,265 B1 | 6/2003 | Spievack |
| 6,579,538 B1 | 6/2003 | Spievack |
| 6,653,291 B1 | 11/2003 | Badylak et al. |
| 6,696,270 B2 | 2/2004 | Badylak et al. |
| 6,783,776 B2 | 8/2004 | Spievack |
| 6,793,939 B2 | 9/2004 | Badylak et al. |
| 6,849,273 B2 | 2/2005 | Spievack |
| 6,852,339 B2 | 2/2005 | Spievack |
| 6,884,619 B2 * | 4/2005 | Hockfield .......... C07K 14/4725 435/325 |
| 6,887,495 B2 | 5/2005 | Spievack |
| 6,890,562 B2 | 5/2005 | Spievack |
| 6,890,563 B2 | 5/2005 | Spievack |
| 6,890,564 B2 | 5/2005 | Spievack |
| 6,893,666 B2 | 5/2005 | Spievack |
| 6,918,396 B1 | 7/2005 | Badylak et al. |
| 6,962,814 B2 | 11/2005 | Mitchell et al. |
| 7,175,841 B2 | 2/2007 | Badylak et al. |
| 7,326,571 B2 | 2/2008 | Freyman |
| 7,402,319 B2 | 7/2008 | Schmidt et al. |
| 7,482,025 B2 | 1/2009 | Badylak |
| 7,771,717 B2 | 8/2010 | Badylak et al. |
| 7,776,596 B2 | 8/2010 | Badylak |
| 7,795,022 B2 | 9/2010 | Badylak |
| 7,815,686 B2 | 10/2010 | Badylak et al. |
| 7,820,634 B2 | 10/2010 | Badylak et al. |
| 7,919,121 B2 | 4/2011 | Badylak et al. |
| 8,003,131 B2 | 8/2011 | Badylak |
| 8,021,692 B2 | 9/2011 | Hiles et al. |
| 8,029,774 B2 | 10/2011 | Badylak et al. |
| 8,084,048 B2 | 12/2011 | Badylak |
| 8,192,763 B2 | 6/2012 | Johnson |
| 8,361,503 B2 | 1/2013 | Badylak et al. |
| 8,409,625 B2 | 4/2013 | Badylak |
| 8,535,719 B2 | 9/2013 | Badylak et al. |
| 8,647,677 B2 | 2/2014 | Badylak et al. |
| 8,673,295 B2 | 3/2014 | Fujimoto et al. |
| 8,691,276 B2 | 4/2014 | Badylak et al. |
| 8,716,438 B2 | 5/2014 | Agrawal et al. |
| 8,802,436 B1 | 8/2014 | Kentner et al. |
| 8,889,791 B2 | 11/2014 | Guan et al. |
| 8,927,003 B2 | 1/2015 | Badylak et al. |
| 8,974,542 B2 | 3/2015 | Fujimoto et al. |
| 9,023,972 B2 | 5/2015 | Chu et al. |
| 9,034,386 B2 | 5/2015 | Flynn |
| 9,119,831 B2 | 9/2015 | Kentner et al. |
| 9,186,435 B2 | 11/2015 | Hiles |
| 9,216,236 B2 | 12/2015 | Machluf et al. |
| 9,238,091 B2 | 1/2016 | Kentner et al. |
| 9,277,999 B2 | 3/2016 | Badylak |
| 9,314,340 B2 | 4/2016 | Badylak |
| 9,340,602 B2 | 5/2016 | Agrawal et al. |
| 9,421,307 B2 | 8/2016 | Amoroso et al. |
| 9,433,701 B2 | 9/2016 | Badylak |
| 9,474,829 B2 | 10/2016 | Kentner et al. |
| 9,480,776 B2 | 11/2016 | Badylak et al. |
| 9,795,713 B2 | 10/2017 | Kentner et al. |
| 9,814,744 B2 | 11/2017 | Badylak et al. |
| 9,848,987 B2 | 12/2017 | Badylak et al. |
| 9,861,662 B2 | 1/2018 | Badylak et al. |
| 10,004,827 B2 | 6/2018 | Badylak |
| 10,005,827 B2 | 6/2018 | Badylak et al. |
| 10,213,526 B2 | 2/2019 | Badylak |
| 10,286,119 B2 | 5/2019 | Badylak |
| 10,729,813 B2 | 8/2020 | Badylak et al. |
| 10,736,991 B2 | 8/2020 | Badylak et al. |
| 2002/0115208 A1 | 8/2002 | Mitchell et al. |
| 2003/0012822 A1 | 1/2003 | Voytik-Harbin et al. |
| 2004/0076657 A1 | 4/2004 | Wolfinbarger, Jr. et al. |
| 2004/0078076 A1 | 4/2004 | Badylak et al. |
| 2004/0175366 A1 | 9/2004 | Badylak et al. |
| 2004/0176855 A1 | 9/2004 | Badylak et al. |
| 2004/0187877 A1 | 9/2004 | Badylak et al. |
| 2004/0191226 A1 | 9/2004 | Badylak et al. |
| 2005/0013870 A1 | 1/2005 | Freyman et al. |
| 2005/0013872 A1 | 1/2005 | Freyman |
| 2005/0181016 A1 | 8/2005 | Freyman et al. |
| 2006/0147433 A1 | 7/2006 | Hiles |
| 2006/0201996 A1 | 9/2006 | Hodde |
| 2006/0292227 A1 | 12/2006 | McPherson |
| 2007/0082060 A1 | 4/2007 | Hiles et al. |
| 2007/0135906 A1 | 6/2007 | Badylak et al. |
| 2007/0196380 A1 * | 8/2007 | Firestone ................ A61P 35/00 424/184.1 |
| 2008/0107750 A1 | 5/2008 | Hodde et al. |
| 2008/0260831 A1 | 10/2008 | Badylak et al. |
| 2008/0268019 A1 | 10/2008 | Badylak et al. |
| 2009/0035855 A1 | 2/2009 | Ying et al. |
| 2009/0053279 A1 | 2/2009 | Badylak et al. |
| 2009/0138074 A1 | 5/2009 | Freyman et al. |
| 2009/0204228 A1 | 8/2009 | Hiles |
| 2010/0047305 A1 | 5/2010 | Naughton et al. |
| 2010/0196480 A1 | 8/2010 | Hiles et al. |
| 2010/0222882 A1 | 9/2010 | Badylak et al. |
| 2010/0226895 A1 | 9/2010 | Boruch |
| 2010/0266654 A1 | 10/2010 | Hodde et al. |
| 2011/0097403 A1 | 4/2011 | Naughton et al. |
| 2011/0151011 A1 | 6/2011 | Flynn |
| 2011/0165676 A1 | 7/2011 | Hopkins |
| 2011/0184439 A1 | 7/2011 | Anderson et al. |
| 2012/0264190 A1 | 10/2012 | Christman et al. |
| 2013/0202563 A1 | 8/2013 | Badylak et al. |
| 2014/0309739 A1 | 4/2014 | Badylak et al. |
| 2014/0356331 A1 | 12/2014 | Badylak et al. |
| 2016/0045552 A1 | 2/2016 | Ramer et al. |
| 2017/0049932 A1 | 2/2017 | Badylak et al. |
| 2018/0043057 A1 | 2/2018 | Kentner et al. |
| 2018/0200405 A1 | 7/2018 | Badylak et al. |
| 2018/0243473 A1 | 8/2018 | Badylak et al. |
| 2019/0015552 A1 | 1/2019 | Badylak et al. |
| 2019/0076574 A1 | 3/2019 | Ramer et al. |
| 2019/0117837 A1 | 4/2019 | Badylak et al. |
| 2020/0009187 A1 | 1/2020 | Badylak et al. |
| 2020/0030495 A1 | 1/2020 | Badylak et al. |
| 2020/0069738 A1 | 3/2020 | Badylak et al. |
| 2020/0261624 A1 | 8/2020 | Crapo et al. |
| 2021/0106526 A1 | 4/2021 | Badylak et al. |

FOREIGN PATENT DOCUMENTS

| | | |
|---|---|---|
| WO | WO2013/009595 | 1/2013 |
| WO | WO 2015/143310 A1 | 9/2015 |
| WO | WO 2015/164728 A1 | 10/2015 |
| WO | WO2017/049167 | 3/2017 |
| WO | WO 2008/109407 A2 | 9/2019 |

OTHER PUBLICATIONS

International Search Report and Written Opinion from parent PCT Application No. PCT/US2018/020764, 9 pages (dated May 17, 2019).

Lu et al., "The extracellular matrix: A dynamic niche in cancer progression," *Journal of Cellular Biology* 196(4): 395-406 (Feb. 20, 2012).

(56) References Cited

OTHER PUBLICATIONS

Saldin, Understanding esophageal adenocarcinoma progression using inflammatory and neoplastic extracellular matric hydrogels, http://grantome.com/grant/NHI/F31-CA210694-01, 3 pages (printed to PDF on Dec. 21, 2016)(Abstract).
Wolf et al., "A hydrogel derived from decellularized dermal extracellular Matrix," Biomaterials 33(29): 7028-7038 (Oct. 2012).
Abed A, Deval B, Assoul N, Bataille I, Portes P, Louedec L, Henin D, Letourneur D, Meddahi-Pellé A. A biocompatible polysaccharide hydrogel-embedded polypropylene mesh for enhanced tissue integration in rats. Tissue Eng Part A. Apr. 2008;14(4):519-27. doi: 10.1089/tea.2007.0134. PMID: 18370927.
Agrawal V, Kelly J, Tottey S, Daly KA, Johnson SA, Siu BF, Reing J, Badylak SF. An isolated cryptic peptide influences osteogenesis and bone remodeling in an adult mammalian model of digit amputation. Tissue Eng Part A. Dec. 2011;17(23-24):3033-44. doi: 10.1089/ten.TEA.2011.0257. Epub Aug. 29, 2011. PMID: 21740273; PMCID: PMC3226059.
Badylak S, Kokini K, Tullius B, Simmons-Byrd A, Morff R. Morphologic study of small intestinal submucosa as a body wall repair device. J Surg Res. Apr. 2002;103(2):190-202. doi: 10.1006/jsre.2001.6349. PMID: 11922734.
Badylak S, Meurling S, Chen M, Spievack A, Simmons-Byrd A. Resorbable bioscaffold for esophageal repair in a dog model. J Pediatr Surg. Jul. 2000;35(7):1097-103. doi: 10.1053/jpsu.2000.7834. PMID: 10917304.
Badylak SF, Brown BN, Gilbert TW, Daly KA, Huber A, Turner NJ. Biologic scaffolds for constructive tissue remodeling. Biomaterials, 2011. 32 (1): 316-319. PMID: 21125721.
Badylak SF, Freytes DO, Gilbert TW. Extracellular matrix as a biological scaffold material: Structure and function. Acta Biomater. Jan. 2009;5(1):1-13. doi: 10.1016/j.actbio.2008.09.013. Epub Oct. 2, 2008. PMID: 18938117.
Badylak SF, Kochupura PV, Cohen IS, Doronin SV, Saltman AE, Gilbert TW, Kelly DJ, Ignotz RA, Gaudette GR. The use of extracellular matrix as an inductive scaffold for the partial replacement of functional myocardium. Cell Transplant. 2006;15 Suppl 1:S29-40. doi: 10.3727/000000006783982368. PMID: 16826793.
Badylak SF, Reing J, Dearth C, Zhang L, Castleton A, White L, Keane T, Smoulder A, Turner N. The impact of sterilization upon extracellular matrix hydrogel structure and function. Journal of Immunology and Regenerative Medicine. Sep. 2018; 2:11-20.
Badylak SF, Valentin JE, Ravindra AK, McCabe GP, Stewart-Akers AM. Macrophage phenotype as a determinant of biologic scaffold remodeling. Tissue Eng Part A, 2008. 14 (11): 1835-1842. PMID: 18950271.
Badylak SF, Vorp DA, Spievack AR, Simmons-Byrd A, Hanke J, Freytes DO, Thapa A, Gilbert TW, Nieponice A. Esophageal reconstruction with ECM and muscle tissue in a dog model. J Surg Res. Sep. 2005;128(1):87-97. doi: 10.1016/j.jss.2005.03.002. PMID: 15922361.
Badylak SF. Regenerative medicine and developmental biology: the role of the extracellular matrix. Anat Rec B New Anat. Nov. 2005;287(1):36-41. doi: 10.1002/ar.b.20081. PMID: 16308858.
Badylak SF. The extracellular matrix as a scaffold material. Biomaterials. Sep. 2007;28(25):3587-93. doi: 10.1016/j.biomaterials. 2007.04.043. Epub May 8, 2007. PMID: 17524477.
Badylak SF. The extracellular matrix as a scaffold for tissue reconstruction. Semin Cell Dev Biol. Oct. 2002;13(5):377-83. doi: 10.1016/s1084952102000940. PMID: 12324220.
Badylak SF. Xenogeneic extracellular matrix as a scaffold for tissue reconstruction. Transpl Immunol. Apr. 2004;12(3-4):367-77. doi: 10.1016/j.trim.2003.12.016. PMID: 15157928.
Beattie AJ, Gilbert TW, Guyot JP, Yates AJ, Badylak SF. Chemoattraction of progenitor cells by remodeling extracellular matrix scaffolds. Tissue Eng Part A. May 2009;15(5):1119-25. doi: 10.1089/ten.tea.2008.0162. PMID: 18837648; PMCID: PMC2789572.
Boccafoschi F, Botta M, Fusaro L, Copes F, Ramella M, Cannas M. Decellularized biological matrices: an interesting approach for cardiovascular tissue repair and regeneration. J Tissue Eng Regen Med. May 2017;11(5):1648-1657. doi: 10.1002/term.2103. Epub Oct. 29, 2015. PMID: 26511323.
Brown BN, Badylak SF. Extracellular matrix as an inductive scaffold for functional tissue reconstruction. Transl Res. 163 (2014), pp. 268-285. PMID: 24291155.
Brown BN, Barnes CA, Kasick RT, Michel R, Gilbert TW, Beer-Stolz D, Castner DG, Ratner BD, Badylak SF. Surface characterization of extracellular matrix scaffolds. Biomaterials. Jan. 2010;31(3):428-37. doi: 10.1016/j.biomaterials.2009.09.061. Epub Oct. 13, 2009. PMID: 19828192; PMCID: PMC2783670.
Brown BN, Londono R, Tottey S, Zhang L, Kukla KA, Wolf MT, Daly KA, Reing JE, Badylak SF. Macrophage phenotype as a predictor of constructive remodeling following the implantation of biologically derived surgical mesh materials. Acta Biomater, 2012. 8 (3): 978-987. PMID: 22166681. PMCID: PMC4325370. NIHMSID: 346364.
Brown BN, Ratner BD, Goodman SB, Amar S, Badylak SF. Macrophage polarization: an opportunity for improved outcomes in biomaterials and regenerative medicine. Biomaterials, 2012. 33 (15): 3792-3802. PMID: 22386919. PMCID: 3727238.
Brown BN, Sicari BM, and Badylak SF (2014) Rethinking Regenerative Medicine: a Macrophage-Centered Approach. Front. Immunol. (5); 510: pp. 1-11. PMID: 25408693. PMCID: PMC4219501.
Brown BN, Valentin JE, Stewart-Akers AM, McCabe GP, Badylak SF. Macrophage phenotype and remodeling outcomes in response to biologic scaffolds with and without a cellular component. Biomaterials, 2009. 30 (8): 1482-1491. PMID: 19121538. PMCID: PMC2805023.
Choi JS, Yang HJ, Kim BS, Kim JD, Kim JY, Yoo B, Park K, Lee HY, Cho YW. Human extracellular matrix (ECM) powders for injectable cell delivery and adipose tissue engineering. J Control Release. Oct. 1, 2009;139(1):2-7. doi: 10.1016/j.jconrel.2009.05. 034. Epub May 28, 2009. PMID: 19481576.
Crapo PM, Gilbert TW, Badylak SF. An overview of tissue and whole organ decellularization processes. Biomaterials. Apr. 2011;32(12):3233-43. doi: 10.1016/j.biomaterials.2011.01.057. Epub Feb. 5, 2011. PMID: 21296410; PMCID: PMC3084613.
Crapo PM, Wang Y. Small intestinal submucosa gel as a potential scaffolding material for cardiac tissue engineering. Acta Biomater. Jun. 2010;6(6):2091-6. doi: 10.1016/j.actbio.2009.10.048. Epub Nov. 1, 2009. PMID: 19887120; PMCID: PMC2862886.
DeQuach JA, Lin JE, Cam C, Hu D, Salvatore MA, Sheikh F, Christman KL. Injectable skeletal muscle matrix hydrogel promotes neovascularization and muscle cell infiltration in a hindlimb ischemia model. Eur Cell Mater. Jun. 5, 2012;23:400-12; discussion 412. doi: 10.22203/ecm.v023a31. PMID: 22665162; PMCID: PMC3524267.
Dziki JL, Huleihel L, Scarritt M, Badylak SF. Extracellular Matrix Bioscaffolds as Immunomodulatory Biomaterials. Tissue Engineering Part A, 2017. 23(19-20): 1152-1159. PMID: 28457179.
Dziki JL, Wang D, Molina CP, Sicari B, Badylak SF. Solubilized Extracellular Matrix Bioscaffolds Derived from Diverse Source Tissues Differentially Influence Macrophage Phenotype. JBMR-A. 2017. 105(1):138-147. PMID: 27601305.
Faust A, Kandakatla, van der Merwe Y, Huleihel L, Hussey GS, Ren T, Johnson S, Badylak SF, Steketee MB. Urinary bladder extracellular matrix hydrogels and matrix-bound vesicles differentially regulate central nervous system neuron viability and axon growth and branching. Journal of Biomaterials Applications, 2017. 31 (9): 1277-1295. PMID: 28447547.
Fercana GR, Yerneni S, Billaud M, Hill JC, VanRyzin P, Richards TD, Sicari B, Badylak SF, Johnson S, Campbell PG, Gleason TG and Phillippi JA. Perivascular Extracellular Matrix Hydrogels Mimic Native Matrix Microarchitecture and Promote Angiogenesis via Basic Fibroblast Growth Factor. Biomaterials, 2017. 123: 142-154. PMID: 28167392. PMCID: PMC5319845.
Freytes DO, Martin J, Velankar SS, Lee AS, Badylak SF. Preparation and rheological characterization of a gel form of the porcine urinary bladder matrix. Biomaterials. Apr. 2008;29(11):1630-7. doi: 10.1016/j.biomaterials.2007.12.014. Epub Jan. 16, 2008. PMID: 18201760.
Freytes DO, Tullius RS, Badylak SF. Effect of storage upon material properties of lyophilized porcine extracellular matrix derived from

(56) References Cited

OTHER PUBLICATIONS the urinary bladder. J Biomed Mater Res B Appl Biomater. Aug. 2006;78(2):327-33. doi: 10.1002/jbm.b.30491. PMID: 16365866.
Freytes DO, Tullius RS, Valentin JE, Stewart-Akers AM, Badylak SF. Hydrated versus lyophilized forms of porcine extracellular matrix derived from the urinary bladder. J Biomed Mater Res A, 2008. 87(4): 862-872. doi:10.1002/jbm.a.31821 PMID: 18228251.
Freytes, DO, Lee AS, Badylak SF. Porcine Urinary Bladder Matrix Derived Gel for Tissue Engineering Applications. Regenerate World Congress and Society for Biomaterials: 2006. Pittsburgh, PA. (Poster and Abstract).
Ghuman G, Mauney C, Donnelly J, Massensini A, Badylak SF, Modo M. Biodegradation of ECM hydrogel promotes endogenous brain tissue restoration in a rat model of stroke. Acta Bio. Epub Sep. 16, 2018.
Ghuman H, Gerwig M, Nicholls FJ, Liu J; Donnelly J; Badylak SF, Modo M. Long-term retention of ECM hydrogel after implantation into a sub-acute stroke cavity reduces lesion volume. Acta Biomater 2017. 63 (2017) 50-63. PMID: 28917705.
Gilbert TW, Sellaro TL, Badylak SF. Decellularization of tissues and organs. Biomaterials, 2006. 27 (19): 3675-3683. PMID: 16519932.
Gilbert TW, Stolz DB, Biancaniello F, Simmons-Byrd A, Badylak SF. Production and characterization of ECM powder: implications for tissue engineering applications. Biomaterials. Apr. 2005;26(12):1431-1435. doi: 10.1016/j.biomaterials.2004.04.042. PMID: 15482831.
Huleihel L, Bartolacci JG, Dziki JL, Vorobyov T, Arnold B, Scarritt ME, LoPresti ST, Brown BN, Badylak SF. Matrix bound nanovesicles recapitulate extracellular matrix effects on macrophage phenotype. Tissue Engineering 2017. 23(21-22): 1283-1294. PMID: 28580875. PMCID: PMC5689118.
Huleihel L, Dziki JL, Bartolacci JG, Rausch T, Scarritt ME, Cramer MC, Vorobyov T, LoPresti ST, Swinehart IT, White LJ, Brown BN, Badylak SF. Macrophage Phenotype in Response to ECM Bioscaffolds. Seminars in Immunology 2017. 29: 2-13. PMID: 28736160. PMCID: PMC5612880.
Hussey GS, Dziki J, Badylak SF. Extracellular matrix-based materials for regenerative medicine. Nat. Rev. Mater. 3, 159-173 (2018).
Hussey GS, Dziki J, Lee Y, Turnquist H, Badylak SF. Matrix bound nanovesicle-associated IL-33 activates a pro-remodeling macrophage phenotype via a non-canonical, ST2-independent pathway. Journal of Immunology and Regenerative Medicine. 2019;3:26-35. DOI: 10.1016/j.regen.2019.01.001. PMID: 31656879. PMCID: PMC6814021.
Keane TJ, DeWard A, Londono R, Saldin LT, Castleton AA, Carey L, Nieponice A, Lagasse E, Badylak SF. Tissue-Specific Effects of Esophageal Extracellular Matrix. Tissue Eng Part A. Sep. 2015;21(17-18):2293-300. doi: 10.1089/ten.TEA.2015.0322. PMID: 26192009; PMCID: PMC4556088.
Keane TJ, Dziki JL, Castleton A, Faulk DM, Messerschmidt V, Londono R, Reing JE, Velankar SS, Badylak SF. Preparation and Characterization of a Biologic Scaffold and Hydrogel from Colonic Mucosa. JBMR Part B. 2017. 105(2):291-306. PMID: 26506408.
Keane TJ, Dziki JL, Sobieski E, Smoulder A, Turner NJ, LJ White, Badylak SF. Restoring Mucosal Barrier Function and Modifying Macrophage Phenotype with an Extracellular Matrix Hydrogel: Potential Therapy for Ulcerative Colitis. Journal of Crohn's and Colitis. 2017 11(3): 360-368. PMID: 27543807.
Keane TJ, Londono R, Carey RM, Carruthers CA, Reing JE, Dearth CL, D'Amore A, Medberry CJ, Badylak SF. Preparation and characterization of a biologic scaffold from esophageal mucosa. Biomaterials. Sep. 2013;34(28):6729-37. doi: 10.1016/j.biomaterials.2013.05.052. Epub Jun. 15, 2013. PMID: 23777917; PMCID: PMC3727430.
Keane TJ, Swinehart I, Badylak SF. Methods of Tissue Decellularization Used for Preparation of Biologic Scaffolds and In-vivo Relevance. Methods. 2015. 84:25-34. PMID: 25791470.
Loneker A, Faulk D, Hussey G, D'Amore A, Badylak SF. Solubilized Liver Extracellular Matrix Maintains Primary Rat Hepatocyte Phenotype In-Vitro. JBMR-A 2016. 104(7): 1846-1847. PMID: 26704367.
Medberry CJ, Crapo PM, Siu BF, Carruthers CA, Wolf MT, Nagarkar SP, Agrawal V, Jones KE, Kelly J, Johnson SA, Velankar SS, Watkins SC, Modo M, Badylak SF. Hydrogels derived from central nervous system extracellular matrix. Biomaterials. 2013. 34(4):1033-40. PMID: 23158935. PMCID: 3512573.
Mehrban N, Pineda Molina C, Quijano LM, Bowen J, Johnson SA, Bartolacci J, Chang JT, Scott DA, Woolfson DN, Birchall MA, Badylak SF. Host macrophage response to injectable hydrogels derived from ECM and α-helical peptides. Acta Bio. 2020; 111 (15): 141-152. DOI: 10.1016/j.actbio.2020.05.022. PMID: 32447065.
Meng FW, Slivka PF, Dearth CL, Badylak SF. Solubilized extracellular matrix from brain and urinary bladder elicits distinct functional and phenotypic responses in macrophages. Biomaterials. 2015. 46: pp. 131-140. PMID: 25678122.
Nadkarni SK, Pierce MC, Park BH, de Boer JF, Whittaker P, Bouma BE, Bressner JE, Halpern E, Houser SL, Tearney GJ. Measurement of collagen and smooth muscle cell content in atherosclerotic plaques using polarization-sensitive optical coherence tomography. J Am Coll Cardiol. Apr. 3, 2007;49(13):1474-81. doi: 10.1016/j.jacc.2006.11.040. Epub Mar. 21, 2007. PMID: 17397678; PMCID: PMC2785549.
Pineda Molina C, Giglio R, Gandhi RM, Sicari BM, Londono R, Hussey G, Bartolacci J, Dziki J, Badylak SF. Comparison of the host macrophage response to synthetic and biologic surgical meshes used for ventral hernia repair. Journal of Immunology and Regenerative Medicine. 2019;3:13-25. DOI:10.1016/J.REGEN.2018.12.002.
Pineda Molina C, Hussey GS, Eriksson J, Shulock MA, Cárdenas Bonilla LL, Giglio RM, Gandhi RM, Sicari BM, Wang D, Londono R, Faulk DM, Turner NJ, Badylak SF. 4-hydroxybutyrate promotes endogenous antimicrobial peptide expression in macrophages. Tissue Engineering Part A. 2019; 25 (9-10):693-706. DOI: https://doi.org/10.1089/ten.tea.2018.0377 PMID: 30982430.
Reing JE, Brown BN, Daly KA, Freund JM, Gilbert TW, Hsiong SX, Huber A, Kullas KE, Tottey S, Wolf MT, Badylak SF. The effects of processing methods upon mechanical and biologic properties of porcine dermal extracellular matrix scaffolds. Biomaterials. Nov. 2010;31(33):8626-33. doi: 10.1016/j.biomaterials.2010.07.083. Epub Aug. 21, 2010. PMID: 20728934; PMCID: PMC2956268.
Reing JE, Zhang L, Myers-Irvin J, Cordero KE, Freytes DO, Heber-Katz E, Bedelbaeva K, McIntosh D, Dewilde A, Braunhut SJ, Badylak SF. Degradation products of extracellular matrix affect cell migration and proliferation. Tissue Eng Part A. Mar. 2009;15(3):605-14. doi: 10.1089/ten.tea.2007.0425. PMID: 18652541.
Saldin LT, Cramer MC, Velankar SS, White LJ, Badylak SF. Extracellular Matrix Hydrogels from Decellularized Tissues: Structure and Function. Acta Bio, 2017. 49: 1-15. PMID: 27915024. PMCID: PMC5253110.
Saldin LT, Klimak M, Hill RC, Cramer MC, Huleihel L, Li X, Quidley-Martin, M, Cardenas D, Keane TJ, Londono R, Hussey GS, Kelly L, Kosovec JE, Lloyd EJ, Omstead AN, Zhang L, Nieponice A, Jobe B, Hansen K, Zaidi AH, Badylak SF. The effect of noraml, metaplastic, and neoplastic esophageal extracellular matrix upon macrophage activation. Journal of Immunology and Regenerative Medicine 2020. DOI:https://doi.org/10.1016/j.regen.2020.100037.
Sawkins MJ, Bowen W, Dhadda P, Markides H, Sidney LE, Taylor AJ, Rose FR, Badylak SF, Shakesheff KM, White LJ. Hydrogels derived from demineralized and decellularized bone extracellular matrix. Acta Biomater. 2013. 9(8):7865-73. PMID: 23624219; PMCID: PMC3711237.
Seif-Naraghi SB, Salvatore MA, Schup-Magoffin PJ, Hu DP, Christman KL. Design and characterization of an injectable pericardial matrix gel: a potentially autologous scaffold for cardiac tissue engineering. Tissue Eng Part A. Jun. 2010;16(6):2017-27. doi: 10.1089/ten.TEA.2009.0768. PMID: 20100033; PMCID: PMC2949214.
Sicari B, Turner N, Badylak SF. An in vivo model system for evaluation of the host response to biomaterials. Methods Mol Biol. 2013;1037:3-25. doi: 10.1007/978-1-62703-505-7_1. PMID: 24029927.
Sicari BM, Dziki JL, Siu BF, Medberry CJ, Dearth CL, Badylak SF. The promotion of a constructive macrophage phenotype by solubilized extracellular matrix. Biomaterials. Oct. 2014;35(30):8605-12. doi: 10.1016/j.biomaterials.2014.06.060. Epub Jul. 16, 2014. PMID: 25043569.

(56) References Cited

OTHER PUBLICATIONS

Slivka P, Badylak SF. Fractionation of an ECM Hydrogel into Structural and Soluble Components Reveals Distinctive Roles in Regulating Macrophage Behavior. Biomater. Sci., 2014, 2 (10), 1521-1534. PMID: 26829566.

Tukmachev D, Forostyak S, Zaviskova K, Koci Z, Vackova I, Vyborny K, Sandvig I, Sandvig A, Medberry C, Badylak SF, Sykova E, Kubinova S. Injectable extracellular matrix hydrogels as scaffolds for spinal cord injury repair. Tissue Engineering Part A Feb. 2016; 22 (3-4):306-17. PMID: 26729284. PMCID: PMC4799710.

Turner NJ, Yates AJ Jr, Weber DJ, Qureshi IR, Stolz DB, Gilbert TW, Badylak SF. Xenogeneic extracellular matrix as an inductive scaffold for regeneration of a functioning musculotendinous junction. Tissue Eng Part A. Nov. 2010;16(11):3309-17. doi: 10.1089/ten.TEA.2010.0169. Epub Aug. 1, 2010. PMID: 20528669.

Uraoka T, Saito Y, Yamamoto K, Fujii T. Submucosal injection solution for gastrointestinal tract endoscopic mucosal resection and endoscopic submucosal dissection. Drug Des Devel Ther. Feb. 6, 2009;2:131-8. doi: 10.2147/dddt.s3219. PMID: 19920900; PMCID: PMC2761197.

Valentin JE, Badylak JS, McCabe GP, Badylak SF. Extracellular matrix bioscaffolds for orthopaedic applications. A comparative histologic study. J Bone Joint Surg Am. Dec. 2006;88(12):2673-86. doi: 10.2106/JBJS.E.01008. PMID: 17142418.

Valentin JE, Stewart-Akers AM, Gilbert TW, Badylak SF. Macrophage participation in the degradation and remodeling of extracellular matrix scaffolds. Tissue Eng Part A, 2009. 15 (7): 1687-1694. PMID: 19125644. PMCID: PMC2792102.

Valentin JE, Turner NJ, Gilbert TW, Badylak SF. Functional skeletal muscle formation with a biologic scaffold. Biomaterials. Oct. 2010;31(29):7475-84. doi: 10.1016/j.biomaterials.2010.06.039. Epub Jul. 17, 2010. PMID: 20638716; PMCID: PMC2922042.

Voytik-Harbin SL, Brightman AO, Kraine MR, Waisner B, Badylak SF. Identification of extractable growth factors from small intestinal submucosa. J Cell Biochem, 1997. 67 (4): 478-491. PMID: 9383707. PMCID: NA.

Wang W, Zhang X, Chao NN, Qin TW, Ding W, Zhang Y, Sang JW, Luo JC. Preparation and characterization of pro-angiogenic gel derived from small intestinal submucosa. Acta Biomater. Jan. 2016;29:135-148. doi: 10.1016/j.actbio.2015.10.013. Epub Oct. 17, 2015. PMID: 26472613.

Wolf MT, Carruthers CA, Dearth CL, Crapo PM, Huber A, Burnsed OA, Londono R, Johnson SA, Daly KA, Stahl EC, Freund JM, Medberry CJ, Carey LE, Nieponice A, Amoroso NJ, Badylak SF. Polypropylene surgical mesh coated with extracellular matrix mitigates the host foreign body response. J Biomed Mater Res A. Jan. 2014;102(1):234-46. doi: 10.1002/jbm.a.34671. Epub Jul. 19, 2013. PMID: 23873846; PMCID: PMC3808505.

Wolf MT, Daly KA, Brennan-Pierce EP, Johnson SA, Carruthers CA, D'Amore A, Nagarkar SP, Velankar SS, Badylak SF. A hydrogel derived from decellularized dermal extracellular matrix. Biomaterials. Oct. 2012;33(29):7028-38. doi: 10.1016/j.biomaterials.2012.06.051. Epub Jul. 11, 2012. PMID: 22789723; PMCID: PMC3408574.

Wolf MT, Daly KA, Reing JE, Badylak SF. Biologic scaffold composed of skeletal muscle extracellular matrix. Biomaterials. Apr. 2012;33(10):2916-25. doi: 10.1016/j.biomaterials.2011.12.055. Epub Jan. 20, 2012. PMID: 22264525; PMCID: PMC5942557.

Wolf MT, Dearth CL, Ranallo CA, LoPresti ST, Carey LE, Daly KA, Brown BN, Badylak SF. Macrophage polarization in response to ECM coated polypropylene mesh. Biomaterials. Aug. 2014;35(25):6838-49. doi: 10.1016/j.biomaterials.2014.04.115. Epub May 21, 2014. PMID: 24856104; PMCID: PMC4347831.

Zhang L, Zhang F, Weng Z, Brown BN, Yan H, Ma XM, Vosler PS, Badylak SF, Dixon CE, Cui XT, Chen J. Effect of an inductive hydrogel composed of urinary bladder matrix upon functional recovery following traumatic brain injury. Tissue Eng Part A. 2013. 19(17-18):1909-18. PubMed PMID: 23596981; PMCID: PMC3726021.

Zhang Y, He Y, Bharadwaj S, Hammam N, Carnagey K, Myers R, Atala A, Van Dyke M. Tissue-specific extracellular matrix coatings for the promotion of cell proliferation and maintenance of cell phenotype. Biomaterials. Aug. 2009;30(23-24):4021-8. doi: 10.1016/j.biomaterials.2009.04.005. Epub May 1, 2009. PMID: 19410290.

Zhu Y, Hideyoshi S, Jiang H, Matsumara Y, Dziki JL, LoPresti ST, Huleihel L, Faria G, Fuhrman LC, Londono R, Badylak SF, Wagner WR. Injectable, porous, biohybrid hydrogels incorporating decellularized tissue components for soft tissue applications. Acta Biomater. 73 (2018) 112-126. PMID: 29649634.

* cited by examiner

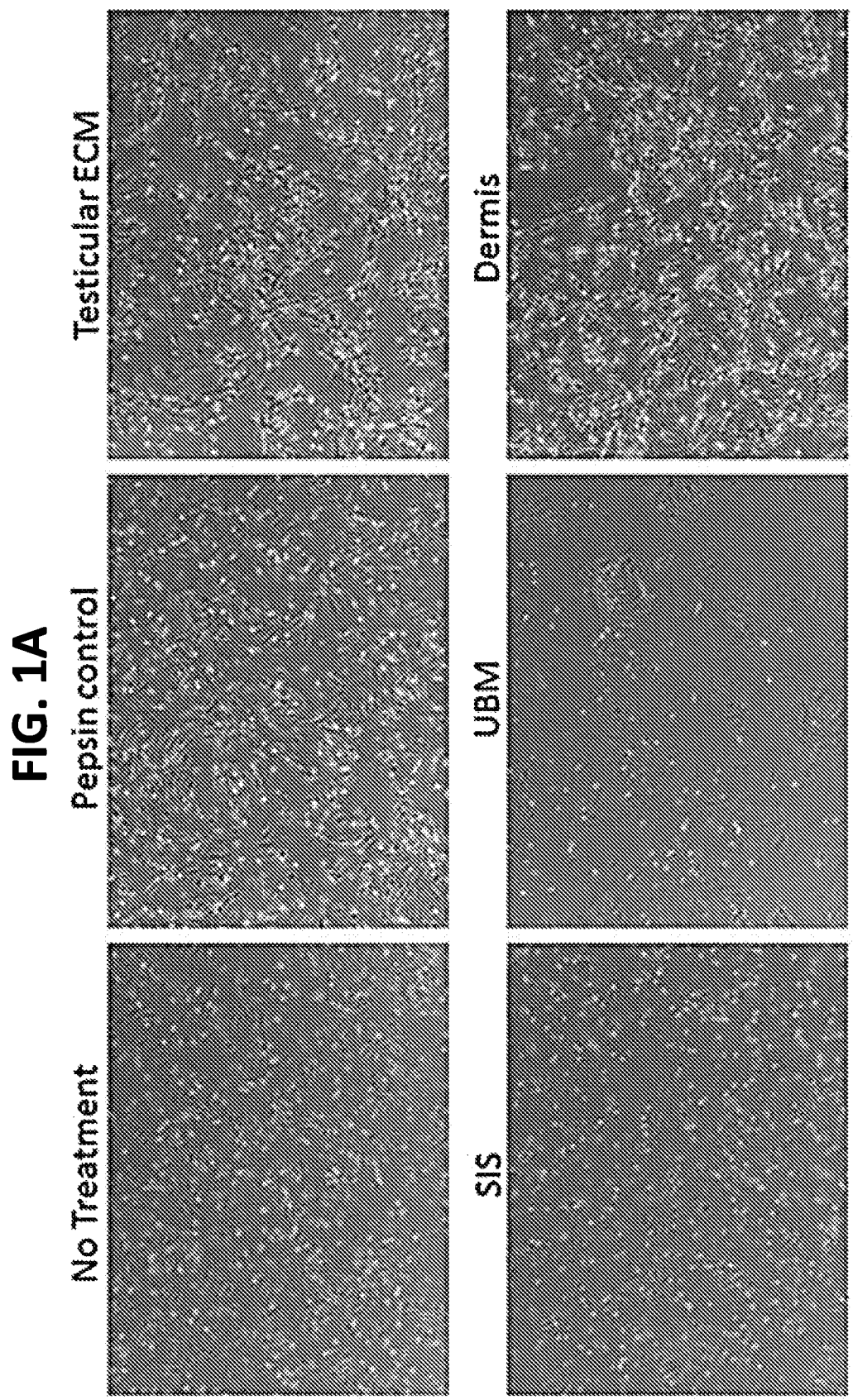

0319 high grade glioma cells

FIG. 3A
Het-1A
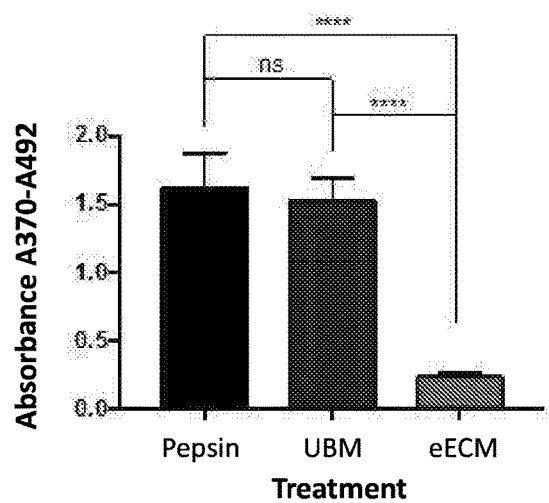
FIG. 3B
CP-A
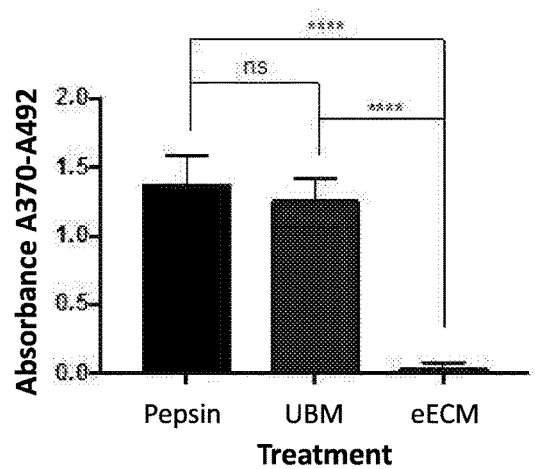
OE33
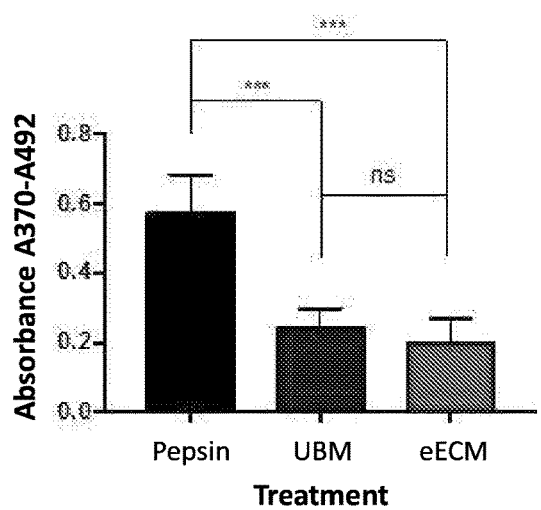
SK-GT-4
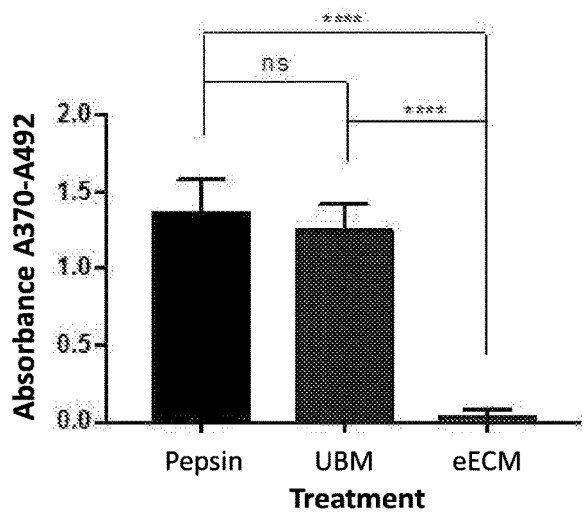
FIG. 3C
FIG. 3D

FIG. 4A
Het-1A
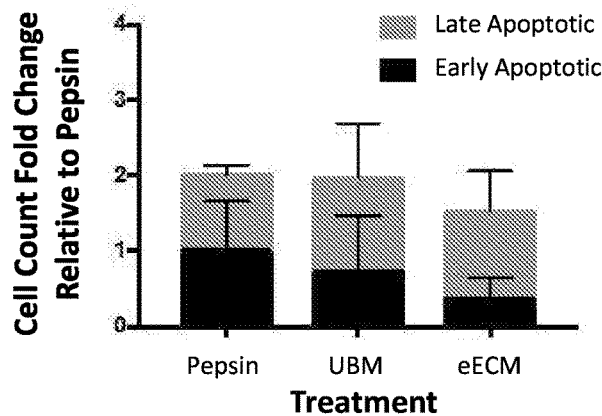
FIG. 4B
CP-A
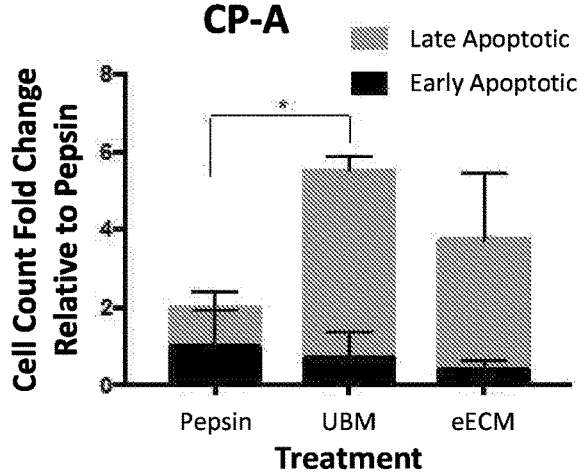
OE33
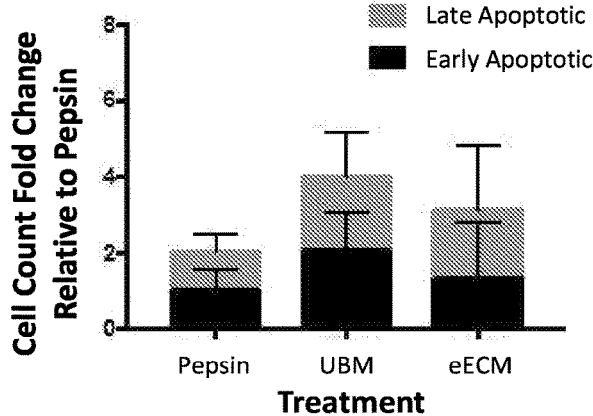
FIG. 4C
SK-GT-4
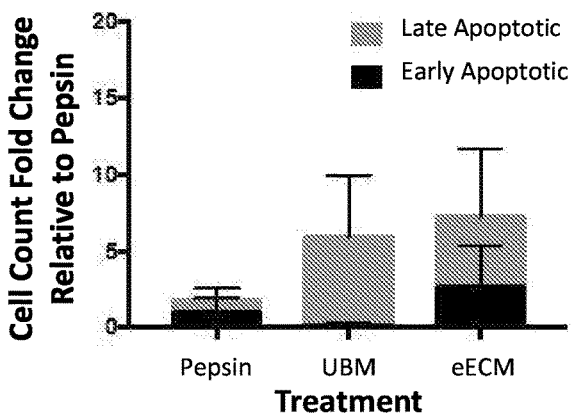
FIG. 4D 0319 high grade glioma cells

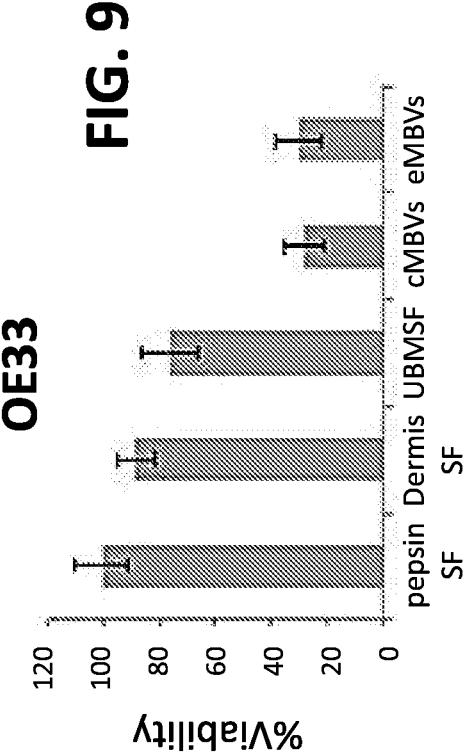
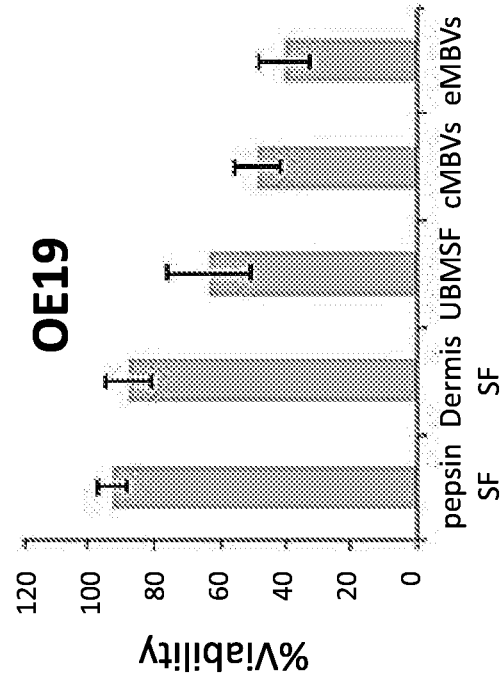
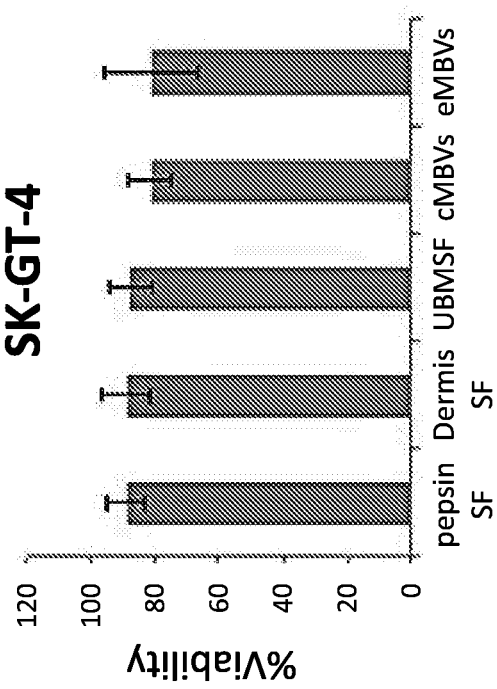
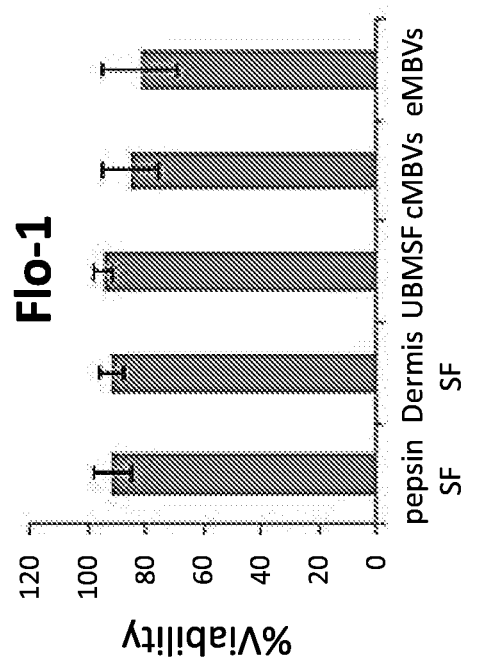
FIG. 9
SF = soluble fraction
cMBVs = collagenase MBVs
eMBVs = elastase MBVs

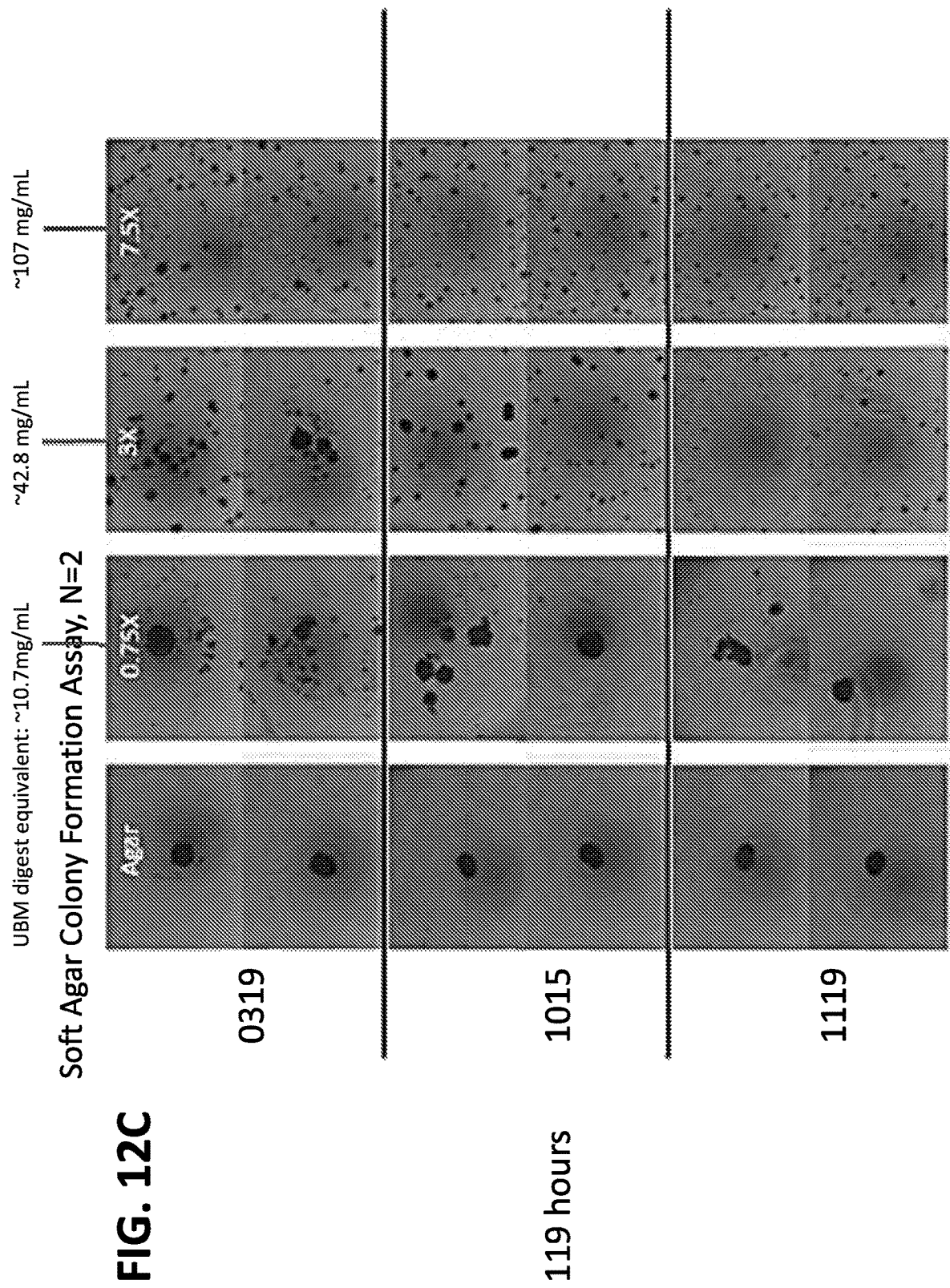

Glioma Cell Proliferation Controlled by ERK Activity-Dependent Surface Expression of PDGFRA "Up-regulated ERK phosphorylation is associated with a reduction of surface PDGFRA expression and a decline of glioma cell proliferation."

Scratch assay

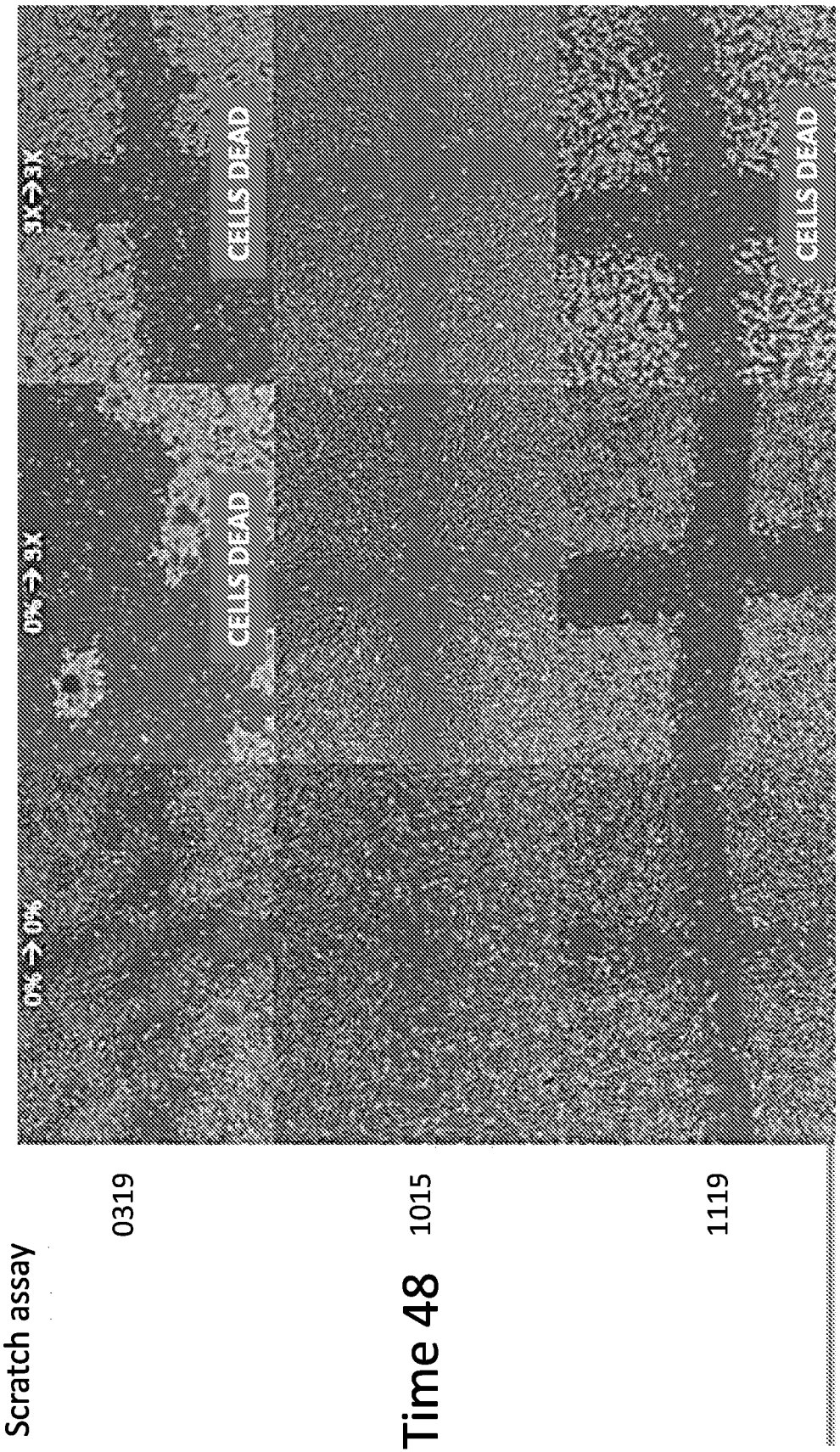

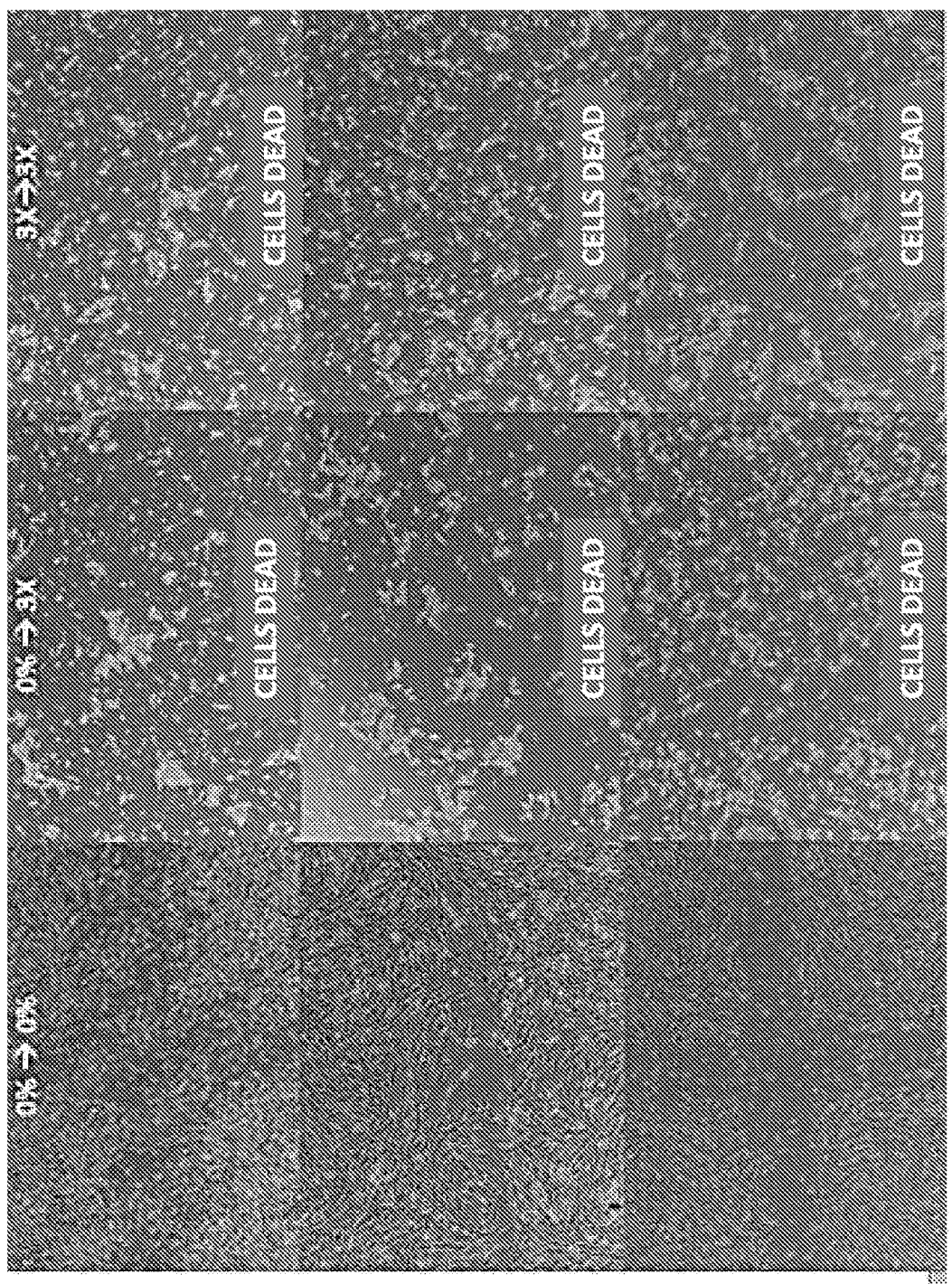

Boyden Chamber Chemotaxis Assay, N=4

Het-1A

CP-A

OE33

SK-GT-4

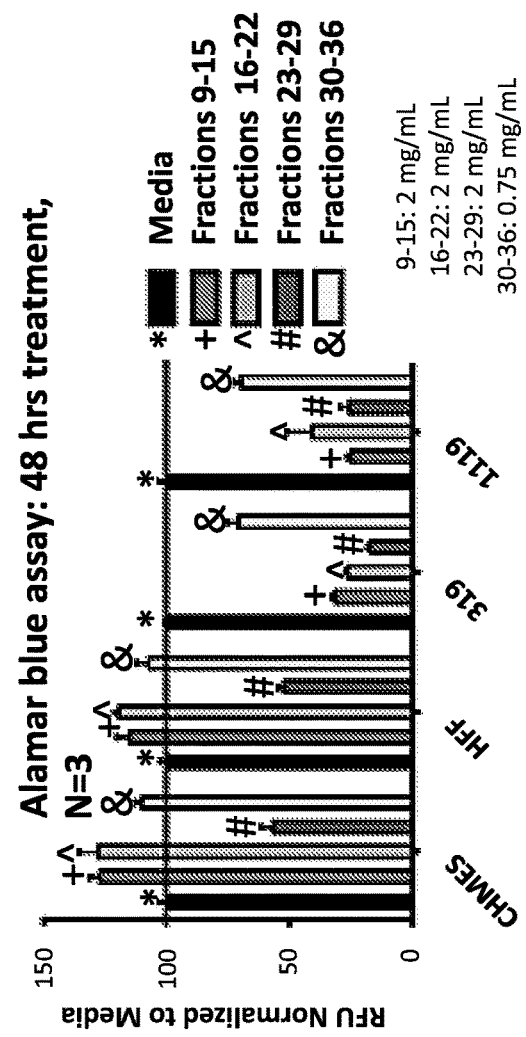
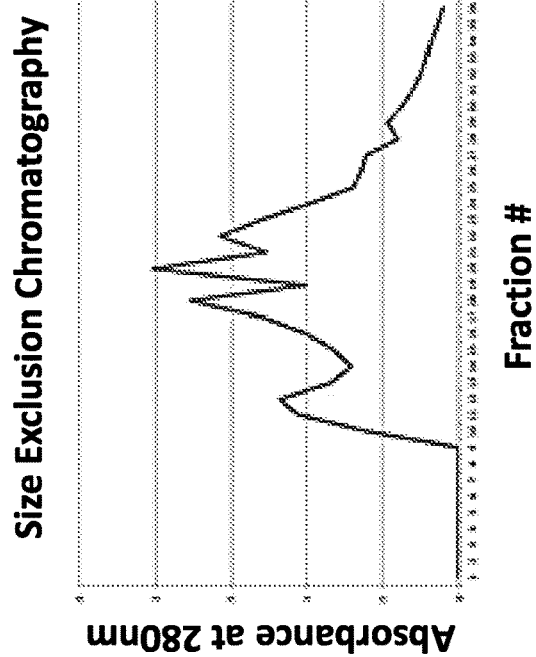
FIG. 25

EXTRACELLULAR MATRIX (ECM) HYDROGEL AND SOLUBLE FRACTION THEREOF FOR THE TREATMENT OF CANCER

CROSS REFERENCE TO RELATED APPLICATION

This is a § 371 U.S. national stage of International Application No. PCT/US2018/020764, filed Mar. 2, 2018, and which claims the benefit of U.S. Provisional Application No. 62/465,988, filed Mar. 2, 2017, which is incorporated herein by reference.

ACKNOWLEDGMENT OF GOVERNMENT SUPPORT

This invention was made with government support under grant nos. CA210694 and TR001858 awarded by the National Institutes of Health. The government has certain rights in the invention.

FIELD

This relates to the field of cancer, specifically to the use of a solubilized extracellular matrix (ECM) hydrogel, and soluble fractions thereof, for the treatment of cancer, such as, but not limited to, glioma.

BACKGROUND

Cancer is the second leading cause of human death next to coronary disease in the United States. Worldwide, millions of people die from cancer every year. In the United States alone, as reported by the American Cancer Society, cancer causes the death of well over a half-million people annually, with over 1.2 million new cases diagnosed per year. Death from cancer is increasing; cancer is soon predicted to become the leading cause of death in the United States.

Gliomas are highly invasive and neurologically destructive tumors that are a leading cause of brain tumor death in both children and adults. Malignant gliomas rarely metastasize outside the central nervous system, but they diffusely invade the brain of an afflicted patient. Treatment for brain gliomas depends on the location, the cell type and the grade of malignancy. Usually treatment involves a combination of surgical resection, systemic chemotherapy and radiotherapy. However, due to the highly infiltrative nature of gliomas, and their intrinsic chemoresistance, 80% of tumors recur. Thus, even with treatment, the median survival time for patients with glioblastoma multiforme is less than 18 months. Thus, there is a need for therapeutic agents to treat cancer, such as glioma.

SUMMARY

It is disclosed herein that a soluble fraction of an extracellular matrix (ECM) hydrogel affects the proliferation, apoptosis and migration of tumor cells, but not non-neoplastic cells.

In some embodiments, methods are for reducing the proliferation of a tumor cell, increasing apoptosis of a tumor cell, and/or decreasing migration of a tumor cell. The method includes contacting the tumor cell with an effective amount of a soluble fraction of an extracellular matrix (ECM) hydrogel, thereby reducing the proliferation of the tumor cell, increasing apoptosis of the tumor cell, and/or decreasing migration of the tumor cell.

In additional embodiments, a method is disclosed for treating a subject with a tumor. The methods include administering to the subject a therapeutically effective amount of a pharmaceutical composition comprising a soluble fraction of an ECM hydrogel and a pharmaceutically acceptable carrier, thereby threating the tumor in the subject.

In specific non-limiting examples, the tumor is a glioma. In other specific non-limiting examples, the ECM hydrogel is a urinary bladder ECM hydrogel.

In further non-limiting examples, the tumor is an esophageal adenocarcinoma. In other specific non-limiting examples, the ECM hydrogel is an esophageal ECM hydrogel.

In yet other embodiments, methods are for reducing the proliferation of a tumor cell, increasing apoptosis of a tumor cell, and/or decreasing migration of a tumor cell. The method includes contacting the tumor cell with an effective amount of a solubilized extracellular matrix (ECM) hydrogel, thereby reducing the proliferation of the tumor cell, increasing apoptosis of the tumor cell, and/or decreasing migration of the tumor cell. In specific non-limiting examples, the tumor is a glioma. In other specific non-limiting examples, the ECM hydrogel is a urinary bladder ECM hydrogel or a small intestinal submucosa (SIS) hydrogel.

The foregoing and other objects, features, and advantages of the invention will become more apparent from the following detailed description, which proceeds with reference to the accompanying figures.

BRIEF DESCRIPTION OF THE DRAWINGS

FIG. 1A-1B: Solubilized ECM bioscaffolds inhibit glioma cell growth. (A) High grade primary human glioma cells were treated with pepsin-solubilized ECM scaffolds for 48 hours. Compared to the no treatment and pepsin control groups, SIS and UBM treatment resulted in a marked reduction in cell viability. The effect of solubilized ECM is tissue specific since neither dermis nor testicular ECM affected cell viability. (B) Primary human glioma cells were treated with soluble fraction from SIS and UBM for 24 hrs.

FIGS. 3A-3D: Solubilized ECM hydrogel decreases esophageal adenocarcinoma proliferation. BrdU proliferation assay (Roche) shows that pepsin-solubilized ECM hydrogel, specifically urinary bladder matrix (UBM) hydrogel and esophageal ECM (eECM) both decrease esophageal epithelial cell cancer cell proliferation (OE33, Sigma) compared to negative control pepsin (C). eECM decreases another esophageal cancer cell (SK-GT-4, Sigma) (D), the cancer precursor Barrett's Esophagus cell line (CP-A, Sigma) (B), and the normal cell line (Het-1A, ATCC) compared to pepsin control (A). UBM does not decrease SK-GT-4, CP-A, or Het-1A cell proliferation (A, B, D) compared to pepsin control. Cells were starved, treated for 24 h, and pulsed with BrdU for 24 h. Absorbance values represent incorporation of BrdU during S phase of replication, with higher absorbance values corresponding to increased proliferation. Experiments are shown for n=3, with technical quadruplicates.

FIGS. 4A-4D: Solubilized ECM hydrogel increases cancer pre-cursor Barrett's Esophagus cell apoptosis. The effect of solubilized ECM on apoptosis was determined using flow cytometry and a dual stain of propidium iodide (PI) and Annexin V. The fold change of early and late apoptotic cells with UBM or eECM treatment compared to pepsin is shown for Het-1A (A), CP-A (B), OE33 (C), and SK-GT-4 (D). For CP-A cells, UBM hydrogel treatment increased late apoptosis (p=0.0095) compared to pepsin control, and eECM hydrogel treatment trended toward increased late apoptosis compared to pepsin control (p=0.0756). UBM and eECM hydrogel did not show differences for early or late apoptosis in Het-1A, OE33, or SK-GT-4 cells compared to pepsin control.

FIG. 9: Soluble fraction of ECM bioscaffolds and MBVs derived from ECM bioscaffolds inhibit esophageal cancer cell viability. The effect of soluble fraction of ECM bioscaffolds and MBV on viability was assessed using an MTT assay. OE33 and OE19 cells showed a decrease in viability with UBM SFF, collagenase MBV (cMBV) and elastase MBV (eMBV) compared to control.

FIG. 12A-12C. Soft Agar Colony Formation Assay, 16 hours (A), 56 hours (B), and 119 hours (C). Colony formation is abrogated in a dose dependent manner in vitro.

FIGS. 14A-14D. Scratch assay, 0 hours (A), 24 hours (B), 48 hours (C), and 96 hours (D). UBM-SF suppresses glioma cell migration. UBM-SF is also lethal for glioma cells.

Figure 23:
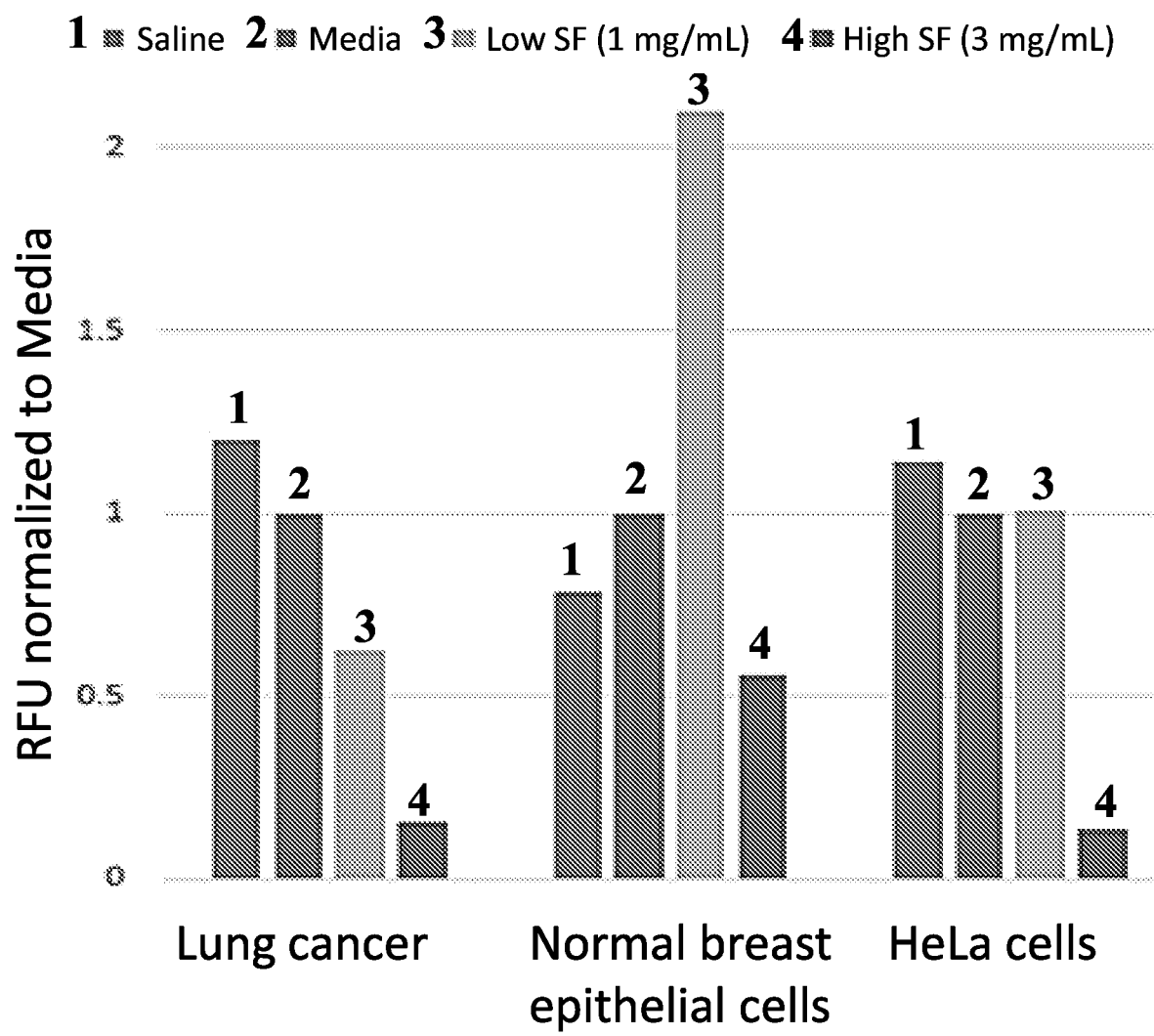

Results from a LIVE/DEAD Cell Viability Assay show that UBM-SF did not affect the viability of normal human primary astrocytes, but significantly decreased the viability glioma cells FIG. 23. UBM Soluble Fraction inhibits cell growth in a variety of neoplastic cells. Cells were treated with indicated test articles for 24 hrs. Cell viability was evaluated by MTT assay.

Figure 24:

FIG. 24. Comparison of Temozolomide to UBM-SF. Temozolomide (TMZ) is an oral alkylating agent used to treat glioblastoma multiforme (GBM) and astrocytomas. Human microglia cells (CHME5), primary human foreskin fibroblasts (HFF), and two primary human glioma cells lines (1015 and 1119) were treated with increasing concentrations of TMZ or UBM-SF for 24 hrs to compare the therapeutic window of each test substrate. TMX was toxic to both normal and neoplastic cell lines, suggesting that TMZ does not have a therapeutic window, or at best, a very narrow therapeutic window. In contrast, UBM-SF had a large therapeutic window where the substrate preferentially killed neoplastic cells without affecting normal cell viability.

FIG. 25. Fractionation of UBM-SF by Size Exclusion Chromatography (SEC). UBM-SF was resolved by SEC using Sepharose CL-6B resin (right panel). The fractions were pooled as indicated and used to treat human microglia cells (CHME5), primary human foreskin fibroblasts (HFF), and two primary human glioma cells lines (0319 and 1119). The data show that fractions 9-22 preferentially kill glioma cells (left panel).

DETAILED DESCRIPTION

It is disclosed herein that solubilized ECM, or a soluble fraction of an ECM hydrogel, can be used to decrease proliferation, increase apoptosis, and/or reduce migration of tumor cells, such as malignant tumor cells. The soluble fraction of ECM hydrogels are not cytotoxic to normal cells, and do not elicit an adverse effect on the surrounding parenchymal tissue. Thus, solubilized ECM, and/or a soluble fraction of an ECM hydrogel, is of use to treat a tumor in a subject. In a specific non-limiting example, the tumor is a glioma and/or the soluble ECM hydrogel is derived from urinary bladder ECM.

Methods are also disclosed herein for reducing the proliferation of a tumor cell, increasing apoptosis of a tumor cell, and/or decreasing migration of a tumor cell. The method includes contacting the tumor cell with an effective amount of a solubilized ECM, or a soluble fraction of an ECM hydrogel, thereby reducing the proliferation of the tumor cell, increasing apoptosis of the tumor cell, and/or decreasing migration of the tumor cell. In specific non-limiting examples, the tumor is a glioma. In other specific non-limiting examples, the ECM hydrogel is a urinary bladder ECM hydrogel or a small intestinal submucosa (SIS) hydrogel. These methods are also of use for treatment of a subject.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Acid Protease: An enzyme that cleaves peptide bonds, wherein the enzyme has increased activity of cleaving peptide bonds in an acidic pH. For example and without limitation, acid proteases can include pepsin and trypsin.

Adenocarcinoma: A type of malignant tumor that can occur in several parts of the body. It is a neoplasia of epithelial tissue that has glandular origin, glandular characteristics, or both.

Apoptosis: A process of programmed cell death that occurs in multicellular organisms. Apoptosis includes characteristic cell changes (morphology) and death. These changes include blebbing, cell shrinkage, nuclear fragmentation, chromatin condensation, chromosomal DNA fragmentation, and global mRNA decay.

Base: A compound or a solution of a compound with a pH greater than 7. For example and without limitation, the base is an alkaline hydroxide or an aqueous solution of an alkaline hydroxide. In certain embodiments, the base is NaOH or NaOH in PBS.

Cancer: A benign or malignant tumor that has undergone characteristic anaplasia with loss of differentiation, increase rate of growth, invasion of surrounding tissue, and is capable of metastasis. For example, thyroid cancer is a tumor that arises in or from thyroid tissue, and esophageal cancer is a tumor that arises in or from esophageal tissue. Residual cancer is cancer that remains in a subject after any form of treatment given to the subject to reduce or eradicate the cancer. Metastatic cancer is a tumor at one or more sites in the body other than the site of origin of the original (primary) cancer from which the metastatic cancer is derived. Cancer includes, but is not limited to, solid tumors.

Centrifugation: The process whereby a centrifugal force is applied to a mixture, whereby more-dense components of the mixture migrate away from the axis of the centrifuge relative to other less-dense components in the mixture. The force that is applied to the mixture is a function of the speed of the centrifuge rotor, and the radius of the spin. In most applications, the force of the spin will result in a precipitate (a pellet) to gather at the bottom of the centrifuge tube, where the remaining solution is properly called a "supernate" or "supernatant." In other similar applications, a density-based separation or "gradient centrifugation" technique is used to isolate a particular species from a mixture that contains components that are both more dense and less dense than the desired component.

During the circular motion of a centrifuge rotor, the force that is applied is the product of the radius and the angular velocity of the spin, where the force is traditionally expressed as an acceleration relative to "g," the standard acceleration due to gravity at the Earth's surface. The centrifugal force that is applied is termed the "relative centrifugal force" (RCF), and is expressed in multiples of "g."

Chemotherapy; chemotherapeutic agents: As used herein, any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating neoplasms such as solid tumors. In one embodiment, a chemotherapeutic agent is radioactive molecule. One of skill in the art can readily identify a chemotherapeutic agent of use (e.g. see Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology 2$^{nd}$ ed., © 2000 Churchill Livingstone, Inc; Baltzer L., Berkery R. (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). Chemotherapeutic agents include those known by those skilled in the art, including but not limited to: 5-fluorouracil (5-FU), azathioprine, cyclophosphamide, antimetabolites (such as Fludarabine), antineoplastics (such as Etoposide, Doxorubicin, methotrexate, and Vincristine), carboplatin, cis-platinum and the taxanes, such as taxol. Rapamycin has also been used as a chemotherapeutic.

Comminute (comminution and comminuting): The process of reducing larger particles into smaller particles, including, without limitation, by grinding, blending, shredding, slicing, milling, cutting, shredding, ECM can be comminuted while in any form, including, but not limited to, hydrated forms, frozen, air-dried, lyophilized, powdered, sheet-form.

Contacting: Placement in direct physical association. Includes both in solid and liquid form.

Cytokine: The term "cytokine" is used as a generic name for a diverse group of soluble proteins and peptides that act as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to, tumor necrosis factor-α, interleukin (IL)-6, IL-10, IL-12, transforming growth factor, and interferon-γ.

Diagnosis: The process of identifying a disease by its signs, symptoms and results of various tests. The conclusion reached through that process is also called "a diagnosis." Forms of testing commonly performed include blood tests, medical imaging, and biopsy.

Extracellular Matrix (ECM): A natural or artificial scaffolding for cell growth. Natural ECMs (ECMs found in multicellular organisms, such as, but not limited to, mammals and humans) are complex mixtures of structural and non-structural biomolecules, including, but not limited to, collagens, elastins, laminins, glycosaminoglycans, proteoglycans, antimicrobials, chemoattractants, cytokines, and growth factors. In mammals, ECM often comprises about 90% collagen, in its various forms. The composition and structure of ECMs vary depending on the source of the tissue. For example, small intestinal submucosa (SIS), urinary bladder matrix (UBM), esophagus (E) and liver stroma ECM each differ in their overall structure and composition due to the unique cellular niche needed for each tissue. An intact "extracellular matrix" and "intact ECM" is an extracellular matrix that retains activity of its structural and non-structural biomolecules, including, but not limited to, collagens, elastins, laminins, glycosaminoglycans, proteoglycans, antimicrobials, chemoattractants, cytokines, and growth factors.

The structure and/or activity of the biomolecules within the ECM can be altered or removed chemically or mechanically, for example, by cross-linking and/or by dialyzing the ECM. Intact ECM essentially has not been enzymatically digested, cross-linked and/or dialyzed, meaning that the ECM has not been subjected to a digestion, dialysis and/or a cross-linking process, or conditions other than processes that occur naturally during storage and handling of ECM prior to solubilization. Thus, ECM that is substantially cross-linked and/or dialyzed (in anything but a trivial manner which does not substantially affect the gelation and functional characteristics of the ECM in its uses described herein) is not considered to be "intact." "Acellular" ECM represents a source tissue that has been treated to remove the cells such that the ECM remains.

Gelation: The formation of a gel from a sol.

Glioma: A tumor that arises from glial cells. Gliomas include ependymomas, astrocytomas, oligodendrogliomas, brainstem gliomas, optic nerve gliomas, and mixed gliomas. Gliomas can be characterized by grade. The World Health Organization (WHO) classifies gliomas as grade I-IV. Low-grade gliomas (WHO grade II) are well-differentiated (not anaplastic) that exhibit benign tendencies and generally have a better prognosis. However, they can reoccur and increase in grade over time so they are classified as malignant. High-grade (WHO grade III-IV) gliomas are undifferentiated or anaplastic. High grade gliomas are malignant and have a poor prognosis. Gliomas are supratentorial (above the tentorium, in the cerebrum, and mostly found in adults) intratentorial (below the tentorium, in the cerebellum, and mostly found in children), or pontine (located in the pons of the brainstem). The symptoms of gliomas depend on wherein the tumor is located within the central nervous system is affected. Symptoms of a brain glioma are headaches, vomiting, seizures, and cranial nerve disorders. A symptom of an optic nerve glioma is visual loss. Symptoms of spinal cord gliomas are pain, weakness, or numbness in the extremities. Generally gliomas spread via the cerebrospinal fluid and can cause "drop metastases" to the spinal cord.

Hydrogel: A network of polymer chains that are hydrophilic, sometimes found as a colloidal gel in which water is the dispersion medium. Hydrogels are highly absorbent natural or synthetic polymeric networks. Hydrogels also possess a degree of flexibility similar to natural tissue.

Inflammation: A localized protective response elicited by injury to tissue. Inflammation is characterized by the appearance in or migration into any tissue space, unit or region of any class of leukocyte in numbers that exceed the number of such cells found within such region of tissue under normal (healthy) circumstances. Inflammation is orchestrated by a complex biological response of vascular tissues to harmful stimuli, such as pathogens, damaged cells, or irritants.

Isolated: An "isolated" biological component (such as a nucleic acid, peptide or protein) has been substantially separated, produced apart from, or purified away from other biological components in the matrix, cell or the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids. An isolated ECM has been separated from cells that produce the ECM.

Isotonic Buffered Solution: A solution that is buffered to a pH between 7.2 and 7.8 and that has a balanced concentration of salts to promote an isotonic environment.

Mammal: This term includes both human and non-human mammals. Similarly, the term "subject" includes both human and veterinary subjects.

Metastasis: Spread of cancer from one location to another in the body. This is a complex series of steps wherein the cancer cells leave the original tumor site and migrate via the bloodstream, lymphatic system, the cerebral spinal fluid, or by extension.

Preventing or treating a disease: "Preventing" a disease refers to inhibiting the partial or full development of a disease, for example in a person who is known to have a predisposition to a disease such as a cancer. An example of a person with a known predisposition is someone with a history of breast cancer in the family, or who has been exposed to factors that predispose the subject to a condition, such as melanoma. "Treatment" refers to a therapeutic intervention that ameliorates a sign or symptom of a disease or pathological condition after it has begun to develop. In several embodiments, treatment refers to a reduction in size of a tumor, a decrease in the number and/or size of metastases, or a decrease in a symptom of the tumor.

Proliferation: Division of cells such that they increase in number. The process of cell division is called mitosis.

Therapeutic agent: Used in a generic sense, it includes treating agents, prophylactic agents, and replacement agents. "Treatment" or "treating" means providing a substance, such as a soluble fraction of an ECM hydrogel, to a patient in an amount sufficient to measurably reduce any disease symptom, slow disease progression or cause disease regression, such as of a tumor. In certain embodiments treatment of the disease may be commenced before the patient presents symptoms of the disease, such as a tumor.

Therapeutically effective amount: A "therapeutically effective amount" of a composition, such as an ECM hydrogel, means an amount effective, when administered to a patient, to provide a therapeutic benefit such as an amelioration of symptoms, reduced decrease progression, or cause disease regression. A quantity of a specified soluble fraction of an ECM hydrogel is sufficient to achieve a desired effect in a subject being treated. A therapeutically effective amount can be administered systemically or locally, such as to the brain. In addition, an effective amount of a soluble fraction of an ECM hydrogel can be administered in a single dose, or in several doses over time. However, the effective amount will be dependent on the preparation applied, the subject being treated, the severity and type of the affliction, and the manner of administration of the compound. The soluble factions of ECM hydrogels of use in the methods disclosed herein have equal applications in medical and veterinary settings. Therefore, the general term "subject" or "patient" is understood to include all animals, including, but not limited to, humans or veterinary subjects, such as other primates, dogs, cats, horses, and cows.

Tumor: An abnormal growth of cells, which can be benign or malignant. Other features often associated with malignancy include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system.

The amount of a tumor in an individual is the "tumor burden" which can be measured as the number, volume, or weight of the tumor. A tumor that invades the surrounding tissue and/or can metastasize is referred to as "malignant." Examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma and retinoblastoma). In one non-limiting example, a tumor is a glioma.

Ultrasonication: The process of exposing ultrasonic waves with a frequency higher than 15 kHz and lower than 400 kHz.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Extracellular Matrix (ECM) Hydrogels and Soluble Fractions Thereof

Methods of preparing ECM hydrogels, are disclosed for example, in U.S. Pat. No. 8,361,503. Any type of extracellular matrix tissue can be used to produce a hydrogel which can be used in the methods as disclosed herein (see U.S. Pat. Nos. 4,902,508; 4,956,178; 5,281,422; 5,352,463; 5,372,821; 5,554,389; 5,573,784; 5,645,860; 5,771,969; 5,753,267; 5,762,966; 5,866,414; 6,099,567; 6,485,723; 6,576, 265; 6,579,538; 6,696,270; 6,783,776; 6,793,939; 6,849,273; 6,852,339; 6,861,074; 6,887,495; 6,890,562; 6,890,563; 6,890,564; and 6,893,666 related to ECM). In certain embodiments, the ECM is isolated from a vertebrate animal, for example and without limitation, from a warm blooded mammalian vertebrate animal including, but not limited to, humans, monkeys, horses, pigs, cows and sheep. In specific non-limiting examples, the ECM is porcine or human.

The ECM can be derived from any organ or tissue, including without limitation, urinary bladder, intestine, liver, esophagus and dermis. The ECM can be obtained from a cell culture. In one embodiment, the ECM is isolated from a urinary bladder. In another embodiment, the ECM is from an esophagus. The ECM may or may not include the basement membrane portion of the ECM. In certain embodiments, the ECM includes at least a portion of the basement membrane.

In some embodiments, as U.S. Pat. No. 8,361,503 (incorporated herein by reference), a urinary bladder ECM, such as porcine bladder ECM is prepared by abrading bladder tissue to remove the outer layers including both the tunica serosa and the tunica muscularis using a longitudinal wiping motion with a scalpel handle and moistened gauze. Following eversion of the tissue segment, the luminal portion of the tunica mucosa is delaminated from the underlying tissue using the same wiping motion. In some embodiments, perforation of the submucosa is prevented. After these tissues are removed, the resulting ECM consists mainly of the tunica submucosa. The production of hydrogels from decellularized dermal ECM is disclosed in Wolf et al., Biomaterials 33: 7028-7038, 2012, incorporated herein by reference. The production of ECM from esophageal tissue is disclosed, for example, in Badylak et al. J Pediatr Surg. 35(7):1097-103, 2000 and Badylak et al., J Surg Res. 2005 September; 128(1):87-97, 2005, both incorporated herein by reference. U.S. Pat. No. 6,893,666, incorporated herein by reference, discloses production of ECM from urinary bladder, skin, esophagus and small intestine.

Commercially available ECM preparations can also be used in the methods, devices and compositions described herein. In one embodiment, the ECM is derived from small intestinal submucosa or SIS. Commercially available preparations include, but are not limited to, SURGISIS™, SURGISIS-ES™, STRATASIS™, and STRATASIS-ES™ (Cook Urological Inc.; Indianapolis, Ind.) and GRAFTPATCH™ (Organogenesis Inc.; Canton Mass.). In another embodiment, the ECM is derived from dermis. Commercially available preparations include, but are not limited to PELVICOL™ (sold as PERMACOL™ in Europe; Bard, Covington, Ga.), REPLIFORM™ (Microvasive; Boston, Mass.) and ALLODERM™ (LifeCell; Branchburg, N.J.). In another embodiment, the ECM is derived from urinary bladder. Commercially available preparations include, but are not limited to UBM (Acell Corporation; Jessup, Md.).

Tissue for preparation of ECM can be harvested in a large variety of ways and once harvested, a variety of portions of the harvested tissue may be used. ECM has also been prepared from the esophagus and small intestine, and hydrogels have been prepared from this ECM, see, for example, Keane et al., Tissue Eng. Part A, 21(17-18): 2293-2300, 2015, incorporated herein by reference. Esophageal ECM can be prepared by mechanically separating the mucosa and submucosa from the muscularis externa and digesting the mucosal layers in a buffer including trypsin, followed by exposure to sucrose, TRITON-X100®, deoxycholic acid, peracetic acid and DNAse. Small intestine submucosa (SIS) can be prepared by mechanically removing the superficial layers of the tunica mucosa, tunica serosa, and tunica muscularis externa from the intact small intestine, leaving the submucosa, muscularis mucosa, and basilar stratum compactum intact. The SIS is then treated with peracetic acid. Exemplary protocols are provided in Keane et al. Dermal hydrogels can be produced, for example, as disclosed in Wolf et al, *J Biomed Mater Res A*. 2013. 35(25): 6838-49. PMID: 23873846. PMCID: 3808505, incorporated herein by reference.

In one embodiment, the ECM is isolated from harvested porcine urinary bladder to prepare urinary bladder matrix (UBM). Excess connective tissue and residual urine are removed from the urinary bladder. The tunica serosa, tunica muscularis externa, tunica submucosa and most of the muscularis mucosa can be removed by mechanical abrasion or by a combination of enzymatic treatment, hydration, and abrasion. Mechanical removal of these tissues can be accomplished by abrasion using a longitudinal wiping motion to remove the outer layers (particularly the abluminal smooth muscle layers) and even the luminal portions of the tunica mucosa (epithelial layers). Mechanical removal of these tissues is accomplished by removal of mesenteric tissues with, for example, Adson-Brown forceps and Metzenbaum scissors and wiping away the tunica muscularis and tunica submucosa using a longitudinal wiping motion with a scalpel handle or other rigid object wrapped in moistened gauze. The epithelial cells of the tunica mucosa can also be dissociated by soaking the tissue in a de-epithelializing solution, for example and without limitation, hypertonic saline. The resulting UBM comprises basement membrane of the tunica mucosa and the adjacent tunica propria, which is further treated with peracetic acid, lyophilized and powdered, see U.S. Pat. No. 8,361,503, incorporated herein by reference.

Dermis sections can used for the preparation of the ECM hydrogels, see PCT Application No. 2015/15164728, incorporated herein by reference. In a specific non-limiting example, the dermis can be decellularized with 0.25% Trypsin/1% Triton X-100 (i.e. no SDS) on a vortex shaker at 300 RPM at room temperature in the following solutions: 0.25% trypsin for 6 hours, 1×; deionized water, 15 minutes, 3×; 70% ethanol, 10 to 12 hours, 1×; 3% $H_2O_2$, 15 minutes, 1×, deionized water, 15 minutes, 2×; 1% Triton X-100 in 0.26% EDTA/0.69% Tris, 6 hours, 1× and then overnight, 1×; deionized water, 15 minutes, 3×; 0.1% peracetic acid/4% ethanol, 2 hours, 1×; PBS, 15 minutes, 2×; and finally deionized water, 15 minutes, 2×. Dermis sheets are then lyophilized and subsequently reduced to particulate form using a Waring blender and a Wiley Mill with a #20 mesh screen.

In some embodiments, the epithelial cells can be delaminated first by first soaking the tissue in a de-epithelializing solution such as hypertonic saline, for example and without limitation, 1.0 N saline, for periods of time ranging from 10 minutes to 4 hours. Exposure to hypertonic saline solution effectively removes the epithelial cells from the underlying basement membrane. The tissue remaining after the initial delamination procedure includes epithelial basement membrane and the tissue layers abluminal to the epithelial basement membrane. This tissue is next subjected to further treatment to remove the majority of abluminal tissues but not the epithelial basement membrane. The outer serosal, adventitial, smooth muscle tissues, tunica submucosa and most of the muscularis mucosa are removed from the remaining de-epithelialized tissue by mechanical abrasion or by a combination of enzymatic treatment, hydration, and abrasion.

ECM can be sterilized by any number of standard techniques, including, but not limited to, exposure to peracetic acid, low dose gamma radiation, gas plasma sterilization, ethylene oxide treatment or electron beam treatment. More typically, sterilization of ECM is obtained by soaking in 0.1% (v/v) peracetic acid, 4% (v/v) ethanol, and 95.9% (v/v) sterile water for two hours. The peracetic acid residue is removed by washing twice for 15 minutes with PBS (pH=7.4) and twice for 15 minutes with sterile water. ECM material can be sterilized by propylene oxide or ethylene oxide treatment, gamma irradiation treatment (0.05 to 4 mRad), gas plasma sterilization, peracetic acid sterilization, or electron beam treatment. The ECM can also be sterilized by treatment with glutaraldehyde, which causes cross linking of the protein material, but this treatment substantially alters the material such that it is slowly resorbed or not resorbed at all and incites a different type of host remodeling which more closely resembles scar tissue formation or encapsulation rather than constructive remodeling. Cross-linking of the protein material can also be induced with carbodiimide or dehydrothermal or photooxidation methods. As disclosed in U.S. Pat. No. 8,361,503, ECM is disinfected by immersion in 0.1% (v/v) peracetic acid (a), 4% (v/v) ethanol, and 96% (v/v) sterile water for 2 h. The ECM material is then washed twice for 15 min with PBS (pH=7.4) and twice for 15 min with deionized water.

Following isolation of the tissue of interest, decellularization is performed by various methods, for example and without limitation, exposure to hypertonic saline, peracetic acid, TRITON-X® or other detergents. Sterilization and decellularization can be simultaneous. For example and without limitation, sterilization with peracetic acid, described above, also can serve to decellularize the ECM. Decellularized ECM can then be dried, either lyophilized (freeze-dried) or air dried. Dried ECM can be comminuted by methods including, but not limited to, tearing, milling, cutting, grinding, and shearing. The comminuted ECM can also be further processed into a powdered form by methods, for example and without limitation, such as grinding or milling in a frozen or freeze-dried state. In order to prepare solubilized ECM tissue, comminuted ECM is digested with an acid protease in an acidic solution to form a digest solution.

In one embodiment, the decellularized ECM material is partially digested by the acid protease. In one example, the decellularized ECM material is digested less completely than a digestion of 1 mg/mL lyophilized, powdered ECM material with 1 mg/mL pepsin in 0.01 M HCl for 48 hours. In another example, the decellularized ECM material is digested less completely than a digestion of 10 mg/mL lyophilized, powdered ECM material with 1 mg/mL pepsin in 0.01 M HCl for 48 hours. In one further embodiment, hyaluronic acid in the ECM material is digested less than 50%, 40%, 30%, 25%, 20% or 10% as compared to undigested ECM material, see PCT Application No. WO 2015/164728, incorporated herein by reference.

The digest solution of ECM typically is kept at a constant stir for a certain amount of time at room temperature. The ECM digest can be used immediately or be stored at −20° C., or frozen at, for example and without limitation, −20° C. or −80° C. Thus, the ECM digest can be kept in a solubilized form. Methods for keeping a hydrogel in a solubilized form are disclosed, for example, in PCT Application No. PCT/US16/52261, filed Sep. 10, 2016, incorporated herein by reference. Any of these methods disclosed in this PCT application are of use to produce solubilized hydrogels to treat tumors, or soluble fractions thereof.

Once the ECM is solubilized (typically substantially completely) the pH of the solution is raised to between 7.2 and 7.8, and according to one embodiment, to pH 7.4. Bases, such as bases containing hydroxyl ions, including NaOH, can be used to raise the pH of the solution. Likewise buffers, such as an isotonic buffer, including, without limitation, Phosphate Buffered Saline (PBS), can be used to bring the solution to a target pH, or to aid in maintaining the pH and ionic strength of the gel to target levels, such as physiological pH and ionic conditions. This forms a "pre-gel" solution which is a solubilized ECM hydrogel. The neutralized digest solution (pre-gel, solubilized ECM hydrogel) can be gelled a lower critical solution temperature, see PCT Publication No. 2015/164728, incorporated herein by reference.

The ECM hydrogel forms a gel (sol to gel transition) upon an increase in temperature. The lower critical solution temperature (LCST) in a reverse gel is a temperature below which a reverse-gelling polymer is soluble in its solvent (e.g. water or an aqueous solvent). As the temperature rises above the LCST in a reverse gel, a hydrogel is formed. The general concept of reverse gelation of polymers and its relation to LCST are broadly known in the chemical arts. The ECM gels described herein are prepared, for example from decellularized, intact ECM as described below, by digestion of the ECM material with an acid protease, neutralization of the material to form a pre-gel, raising the temperature of the pre-gel above the LCST of the pre-gel to cause the pre-gel to gel, such as to form a hydrogel. The transition temperature for acid-protease-digested from solution to gel is typically within the range of from 10° C. to 40° C. and any increments or ranges there between, for example from 20° C. to 35° C. For example, the pre-gel can be warmed to 37° C. to form a hydrogel. The hydrogel is then centrifuged, and the soluble fraction is collected. In order to separate the structural from soluble components of the resultant hydrogel, the hydrogel is centrifuged at a sufficient g-force and for a sufficient time to separate the solution and structural components of the hydrogel. By solution in the context of this separation method, it is referred to the resultant aqueous solution and constituents dissolved or otherwise remaining in the aqueous solution after centrifugation at about 10,000 g (10,000 times gravity) to about 100,000 g, such as about 10,000 g, 15,000 g, 20,000 g, 25,000 g, 30,000 g, 35,000 g, 40,000 g, 45,000 g, 50,000 g, 55,000 g, 60,000 g, 65,000 g, 70,000 g, 75,000 g, 80,000 g, 85,000 g, 90,000 g, 95,000 g, or 100,000 g. In one specific non-limiting example, centrifugation is performed at about 25,000 g for about 30 minutes. In some embodiments, centrifugation is about 10,000 g for about 1 hour to about 24 hours, such as about 1 hour to about 20 hours, about 1 hour to about 10 hours, or about 1 hour to about 5 hours, such as about 1, 2, 3, 4, 5, 6, 7, 8, 9, 10, 11, 12, 13, 14, 15, 16, 17, 18, 19, 20, 21, 22, 23, or 24 hours. Centrifugation can be performed, for example, for about 12 hours to about 24 hours, or about 18 to about 24 hours. In other embodiments, centrifugation is about 100,000 g for about 1 to about 20 minutes, such as about 5 to about 10 minutes, such as for about 1, 2, 3, 4, 5, 6, 7, 8, 9, 10, 11, 12, 13, 14, 15, 16, 17, 18, 19 or 20 minutes. In a non-limiting example, centrifugation is performed at 100,000 g for about 10 minutes. The method typically does not include a dialysis step prior to gelation, yielding a more-complete ECM-like matrix that typically gels at 37° C. at specific rates (see below).

Thus, the ECM typically can be derived from mammalian tissue, such as, without limitation from one of urinary bladder, esophagus, or small intestine. In one specific non-limiting example, the ECM is derived from urinal bladder. According to one embodiment, the decellularized ECM material prepared from the tissue is not dialyzed prior to the partial or complete digestion with the acid protease and/or is not dialyzed after digesting with an acid protease and before gelling of the neutralized, digested ECM material.

In one non-limiting embodiment, the ECM is lyophilized and comminuted. The ECM is then solubilized with an acid protease in an acidic solution to produce digested ECM, such as urinary bladder ECM. The acid protease may be, without limitation, pepsin or trypsin, or a combination thereof. The ECM can then be solubilized at an acid pH suitable or optimal for the protease, such as greater than about pH 2, or between pH and 4, for example in a 0.01M HCl solution. The solution typically is solubilized for about 12 to about 48 hours, depending upon the tissue type (e.g., see examples below), with mixing (stirring, agitation, admixing, blending, rotating, tilting, etc.). ECM hydrogel is prepared by (i) comminuting an extracellular matrix, (ii) solubilizing intact, non-dialyzed or non-cross-linked extracellular matrix by digestion with an acid protease in an acidic solution to produce a digest solution, (iii) raising the pH of the digest solution to a pH between 7.2 and 7.8 to produce a neutralized digest solution (pre-gel solution), and (iv) gelling the solution. The ECM hydrogel is then centrifuged, and the soluble fraction is collected.

Soluble fractions of ECM hydrogels can be produced, for example, by partially or completely digesting an ECM, such as a decellularized ECM with an acid protease, neutralizing the digested ECM material to a pH of 7.0-8.0, e.g., 7.2-7.8 or 7.4, gelling the neutralized, digested ECM material at a temperature above its Lower Critical Solution Temperature, and centrifuging the gelled ECM material to produce a pellet and a supernatant. The supernatant is then collected and utilized in the methods disclosed herein.

Exemplary methods for fractionation of an ECM hydrogel are disclosed, for example, in PCT Publication No. WO 2015/164728, incorporated herein by reference. The methods disclosed in this PCT publication include partially or completely digesting with an acid protease, such as pepsin, decellularized ECM material prepared from a tissue; neutralizing the digested ECM material to a pH of 7.0-8.0, 7.2-7.8 or 7.4; gelling the neutralized, digested ECM material at a temperature above its Lower Critical Solution Temperature; centrifuging the gelled ECM material to produce a pellet and a supernatant; and separating the supernatant and the pellet thereby separating a structural and a soluble fraction of the ECM material.

The ECM hydrogel, when exposed to temperatures above the Lower Critical Solution Temperature, such as a temperature of about 37° C., forms the gel. The ECM hydrogel in the "pre-gel" form (the solubilized ECM hydrogel), can be frozen and stored at, for example and without limitation, −20° C. or −80° C. The ECM hydrogel in the "pre-gel" form can be stored at room temperature, such about 25° C. In some non-limiting examples, the ECM hydrogel is in the pre-gel form at below 37° C., such as at 25, 24, 23, 22, 21, 20, 19, 18, 17, 16, 15, 14, 13, 12, 11, 10, 9, 8, 7, 6, 5, 4° C. The ECM hydrogel can be frozen for storage, and thus, can be stored at below 0° C. As used herein, the term "pre-gel form" or "pre-gel" refers to the ECM hydrogel wherein the pH is increased, but has not gelled. For example and without limitation, an ECM hydrogel in the pre-gel form has a pH between 7.2 and 7.8. In some embodiments, the solubilized ECM hydrogel is used in the methods disclosed herein. Methods for keeping a hydrogel in a solubilized form are disclosed, for example, in PCT Application No. PCT/US16/52261, filed Sep. 10, 2016, incorporated herein by reference.

Any of these methods disclosed in this PCT application are of use to produce solubilized hydrogels to treat tumors, or soluble fractions thereof.

When it is of interest to produce the soluble fraction, the temperature of the ECM hydrogel is raised above its Lower Critical Solution Temperature. The ECM hydrogel is then centrifuged, and the soluble faction is collected.

In some embodiments, the soluble fraction is utilized in the methods disclosed herein. The soluble fraction can be applied directly, or can be included in a pharmaceutical composition with additional ingredients, such as, but not limited to, pharmaceutically acceptable carriers. The soluble fraction, and pharmaceutical compositions including the soluble fraction, may be applied or administered in a variety of ways, either as a dry, e.g., lyophilized powder, a solution, a gel, etc. The composition can be administered by itself, or with a device.

In another embodiment, the supernatant/soluble fraction is further purified by precipitating remaining structural components from the supernatant, for example, by salting out those structural components such as by increasing the salt concentration in the supernatant. The soluble fraction is optionally dried, for example by lyophilization and then can be re-hydrated using an appropriate aqueous solution, such as water, saline, isotonic buffer, PBS, or serum-free medium. According to one embodiment, the supernatant is concentrated. That is, the lyophilized supernatant is re-hydrated to a volume, less than the volume of the supernatant before lyophilization, optionally the lyophilized supernatant is re-hydrated to a volume <10%, 10%, 20%, 25% or 50% of the volume of the supernatant before lyophilization, thereby producing a concentrated solution of soluble ECM components.

In some embodiments, the biologically active soluble fraction of ECM composition prepared by any method described herein is absorbed into, adsorbed onto, or otherwise dispersed onto or into a biocompatible substrate. Non-limiting examples of a biocompatible substrate include: a mesh, a non-woven, decellularized tissue, a polymer composition, a polymeric structure, a cell growth scaffold, an implant, an orthopedic implant, and intraocular lens, sutures, intravascular implants, stents, and transplants. The compositions described herein can be applied to or incorporated into, by any suitable method, a non-woven material, such as a bandage, a suture, an implant, such as a ceramic, metal, or polymeric implant, for example a prosthesis, artificial or otherwise-modified vessel, a valve, an intraocular lens, or a tissue implant. As used herein, the term "coat", and related cognates such as "coated" and "coating," refers to a process comprising of covering, in part or in whole, an inorganic structure with a composition described herein. For example and without limitation, coating of an inorganic structure with solubilized fraction can include methods such as pouring, embedding, layering, dipping, spraying. Ultrasonication may be used to aid in coating of an inorganic structure.

In another embodiment, the composition including the soluble fraction of an ECM hydrogel is coated onto a biocompatible structural material, such as a metal, an inorganic calcium compound such as calcium hydroxide, calcium phosphate or calcium carbonate, or a ceramic composition. Non-limiting examples of suitable metals are cobalt-chrome alloys, stainless steel alloys, titanium alloys, tantalum alloys, titanium-tantalum alloys, which can include both non-metallic and metallic components, such as molybdenum, tantalum, niobium, zirconium, iron, manganese, chromium, cobalt, nickel aluminum and lanthanum, including without limitation, CP Ti (commercially pure titanium)

of various grades or Ti 6Al 4V (90% wt. Ti, 6% wt. Al and 4% wt. V), stainless steel 316, Nitinol (Nickel-titanium alloy), titanium alloys coated with hydroxyapatite. Metals are useful due to high strength, flexibility, and biocompatibility. Metals also can be formed into complex shapes and many can withstand corrosion in the biological environments, reduce wear, and not cause damage to tissues. Other compositions, including ceramics, calcium compounds, such as, without limitation, aragonite. Combinations of metal, ceramics and/or other materials also can be of use.

Any useful agent can be mixed into, co-delivered, co-applied or otherwise combined with any composition as described herein. For example and without limitation, useful agents include interferons, interleukins, chemokines, monokines, hormones, angiogenic factors, chemotherapeutics and antibiotics.

Methods of Use

Methods are disclosed herein for reducing the proliferation of tumor cells, either in vivo or in vitro. Methods are also disclosed herein for increasing the apoptosis of tumor cells, either in vivo or in vitro. In addition, methods are disclosed herein for decreasing the migration of tumor cells, either in vivo or in vitro. In some embodiments, the methods include contacting the tumor cells with an effective amount of a solubilized ECM hydrogel. In other embodiments, the methods include contacting the tumor cells with an effective amount of a soluble fraction of an extracellular matrix hydrogel. In some embodiments, the tumor cells are glioma cells. In other embodiments, the ECM is urinary bladder ECM. In further embodiments, the tumor cells are glioma cells and the ECM is urinary bladder ECM or SIS ECM. In further embodiments, the tumor cells are esophageal adenocarcinoma cells. In other embodiments, the extracellular matrix is esophageal ECM. In further embodiments, the tumor cells are esophageal adenocarcinoma and the ECM is esophageal ECM.

All of the methods disclosed herein can be used for any type of glioma or glioma cell. The glioma can be an ependymoma, astrocytoma, oligodendroglioma, brainstem glioma, optic nerve glioma, or a mixed glioma. The glioma can be WHO grade I, II, III or IV. The glioma can be a Low-grade gliomas or a high-grade (WHO grade III-IV) glioma. The glioma can be supratentorial, intratentorial or pontine.

Methods are also provided for treating a tumor in a subject. In some embodiments, the methods include treating an existing tumor in a subject. In additional embodiments, methods are disclosed herein for preventing conversion of a benign to a malignant lesion, or preventing metastasis in a subject. In some non-limiting examples, the methods reduce a symptom of the tumor in the subject. In additional non-limiting examples, the tumor is a solid tumor. In some embodiments, the tumor cells are glioma cells. In other embodiments, the ECM is urinary bladder ECM. In further embodiments, the tumor cells are glioma cells and the ECM is urinary bladder ECM. In further embodiments, the tumor cells are esophageal adenocarcinoma cells. In other embodiments, the extracellular matrix is esophageal ECM. In further embodiments, the tumor cells are esophageal adenocarcinoma and the ECM is esophageal ECM.

Generally, the methods include selecting a subject having a tumor, such as a benign or malignant tumor, and administering to the subject a therapeutically effective amount of a solubilized ECM hydrogel and/or a soluble fraction of an ECM hydrogel. In some embodiments, methods disclosed herein include selecting a subject in need of treatment, such as a subject with a glioma, and administering to the subject a therapeutically effective amount of the soluble fraction of the ECM hydrogel. Additional agents can also be administered to the subject of interest, such as, but not limited to, chemotherapeutic agents. Additional treatments can also be administered to the subject, such as, but not limited to, surgical resection of the tumor.

The tumor can be benign or malignant. The tumor can be a solid tumor or a lymphoproliferative tumor. The tumor can be any tumor of interest, including, but not limited to, glioma. In other embodiments, the tumor is a lymphoma, breast cancer, lung cancer and colon cancer. Additional examples are skin tumors, breast tumors, brain tumors, cervical carcinomas, testicular carcinomas, head and neck tumors, gastrointestinal tract tumors, genitourinary system tumors, gynecological system tumors, breast, endocrine system tumors, skin tumors, a sarcoma of the soft tissue and bone, a mesothelioma, a melanoma, a neoplasm of the central nervous system, or a leukemia. In some embodiments, the tumor is a head and neck tumor, such as tumors of the nasal cavity, paranasal sinuses, nasopharynx, oral cavity, oropharynx, larynx, hypopharynx, salivary glands and paragangliomas. In other embodiments, the tumor is a lung tumor, such as a non-small cell lung cancer or a small cell lung cancer. In further embodiments, the tumor can be a tumor of the gastrointestinal tract, such as cancer of the esophagus, stomach, pancreas, liver, biliary tree, small intestine, colon, rectum and anal region. In yet other embodiments, the tumor can be a tumor of the genitourinary system, such as cancer of the kidney, urethra, bladder, prostate, urethra, penis and testis. In some embodiments, the tumor is a gynecologic tumor, such as cancer of the cervix, vagina, vulva, uterine body, gestational trophoblastic diseases, ovarian, fallopian tube, peritoneal, or breast. In other embodiments, the tumor is an endocrine system tumor, such as a thyroid tumor, parathyroid tumor, adrenal cortex tumor, pancreatic endocrine tumor, carcinoid tumor and carcinoid syndrome. The tumor can be a sarcoma of the soft tissue and bone, a mesothelioma, a cancer of the skin, a melanoma, comprising cutaneous melanomas and intraocular melanomas, a neoplasm of the central nervous system, a cancer of the childhood, comprising retinoblastoma, Wilm's tumor, neurofibromatoses, neuroblastoma, Ewing's sarcoma family of tumors, rhabdomyosarcoma. The tumor can be a lymphoma, comprising non-Hodgkin's lymphomas, cutaneous T-cell lymphomas, primary central nervous system lymphoma, and Hodgkin's disease. The tumor can be a leukemia, such as acute leukemia, chronic myelogenous leukemia and lymphocytic leukemia. The tumor can be plasma cell neoplasms, a cancer of unknown primary site, a peritoneal carcinomastosis, a Kaposi's sarcoma, AIDS-associated lymphomas, AIDS-associated primary central nervous system lymphoma, AIDS-associated Hodgkin's disease and AIDS-associated anogenital cancers, a metastatic cancer to the liver, metastatic cancer to the bone, malignant pleural and pericardial effusions and malignant ascites. In specific non-liming examples, the tumor is melanoma or colon cancer.

Treatment of the tumor is generally initiated after the diagnosis of the tumor, or after the initiation of a precursor condition (such as dysplasia or development of a benign tumor). Treatment can be initiated at the early stages of cancer, for instance, can be initiated before a subject manifests symptoms of a condition, such as during a stage I diagnosis or at the time dysplasia is diagnosed. However, treatment can be initiated during any stage of the disease, such as but not limited to stage I, stage II, stage III and stage IV cancers. In some examples, treatment is administered to these subjects with a benign tumor that can convert into a malignant or even metastatic tumor.

The presence of a tumor can be determined by methods known in the art, and typically include cytological and morphological evaluation. The tumor can be an established tumor.

Treatment initiated after the development of a condition, such as malignant cancer, may result in decreasing the severity of the symptoms of one of the conditions, or completely removing the symptoms, or reducing metastasis, tumor volume or number of tumors. In some examples, the tumor becomes undetectable following treatment. In one aspect of the disclosure, the formation of tumors, such as metastasis, is delayed, prevented or decreased. In another aspect, the size of the primary tumor is decreased. In a further aspect, a symptom of the tumor is decreased. In yet another aspect, tumor volume is decreased.

In some embodiments, methods are disclosed for the treatment of a subject with a tumor. In some non-limiting examples, a therapeutically effective amount of any of the solubilized fractions of the ECM hydrogel, as disclosed herein, is utilized. In other non-limiting examples, a therapeutically effective amount of any of the solubilized form of the ECM hydrogel, as disclosed herein, is utilized.

In specific non-limiting examples, the ECM hydrogel is a urinary bladder ECM hydrogel. In other non-limiting examples, the ECM hydrogel is a SIS ECM hydrogel. In some embodiments the administration reduces tumor cell proliferation, increases tumor cell apoptosis and/or decreases tumor cell migration. The administration can be directly to the tumor. In specific non-limiting examples, the tumor is a glioma.

Treatment prior to the development of the condition, such as treatment upon detecting dysplasia or an early (benign) precursor condition, is referred to herein as treatment of a subject that is "at risk" of developing the condition. In some embodiments, administration of a composition, such as a solubilized fraction of a ECM hydrogel, or a pharmaceutical composition comprising the soluble fraction, can be performed during or after the occurrence of the conditions described herein. In some embodiments, the subject does not have Barrett's esophagus. In other embodiments, the subject has Barrett's esophagus. In some examples the subject has an epithelial dysplasia, for example of the uterine cervix, vaginal or anal epithelium, or epithelial dysplasia in the oral cavity or sinus. In some examples the epithelial dysplasia has occurred or is at risk of occurring, because of infection with an oncogenic human papilloma virus (HPV).

Pharmaceutical compositions can include the soluble fraction of the ECM hydrogel, and/or the solubilized ECM hydrogel, and optionally one or more additional chemotherapeutic agents. These compositions are of use for threating a tumor. These compositions can be formulated in a variety of ways for administration to a subject to affect the proliferation of cells in the tumor, or to delay, prevent, reduce the risk of developing, or treat, or reduce the incidence of metastasis, of any tumor of interest. The compositions described herein can also be formulated for application such that they prevent metastasis of an initial lesion. In some embodiments, the compositions are formulated for local administration, such as intratumoral administration. Pharmaceutical compositions are thus provided for both local use and for systemic use, formulated for use in human or veterinary medicine. Local administration can be directly to a tumor, or a site of tumor resection.

While the disclosed methods and compositions will typically be used to treat human subjects they may also be used to treat similar or identical diseases in other vertebrates, such as other primates, dogs, cats, horses, and cows. A suitable administration format may best be determined by a medical practitioner for each subject individually. Various pharmaceutically acceptable carriers and their formulation are described in standard formulation treatises, e.g., *Remington's Pharmaceutical Sciences* by E. W. Martin. See also Wang, Y. J. and Hanson, M. A., *Journal of Parenteral Science and Technology*, Technical Report No. 10, Supp. 42: 2S, 1988. The dosage form of the pharmaceutical composition will be determined by the mode of administration chosen.

In some embodiments, when locally administered into cells in an affected area or a tissue of interest, such as a tumor, the disclosed compositions reduce tumor cell proliferation, increase tumor cell apoptosis and/or reduce tumor cell migration. Local administration can also be by direct injection into the tumor, or by spraying, brushing, or other application to a tumor or site of tumor excision. In some embodiments, a delivery vehicle, such as collagen, is utilized. Biocompatible supports, such as mesh, can also be used, wherein the support is coated with the hydrogel. The soluble fraction of the solubilized ECM hydrogel, or the solubilized ECM hydrogel can be administered by any route, including parenteral administration, for example, intravenous, intraperitoneal, intramuscular, intraperitoneal, intrasternal, or intraarticular injection or infusion, or by sublingual, oral, topical, intranasal, or transmucosal administration, or by pulmonary inhalation. The appropriate route of administration can be selected by a physician based on the presentation of the tumor.

When the soluble faction of the solubilized ECM hydrogels is provided as parenteral compositions, e.g. for injection or infusion, they are generally suspended in an aqueous carrier, for example, in an isotonic buffer solution at a pH of about 3.0 to about 8.0, preferably at a pH of about 3.5 to about 7.4, such as about 7.2 to about 7.4. Useful buffers include sodium citrate-citric acid and sodium phosphate-phosphoric acid, and sodium acetate-acetic acid buffers.

A form of repository or "depot" slow release preparation may be used so that therapeutically effective amounts of the preparation are delivered into the bloodstream over many hours or days following injection or delivery. Suitable examples of sustained-release compositions include suitable polymeric materials (such as, for example, semi-permeable polymer matrices in the form of shaped articles, e.g., films, or microcapsules), suitable hydrophobic materials (such as, for example, an emulsion in an acceptable oil) or ion exchange resins, and sparingly soluble derivatives (such as, for example, a sparingly soluble salt). Sustained-release formulations may be administered orally, rectally, parenterally, intracisternally, intravaginally, intraperitoneally, topically (as by powders, ointments, gels, drops or transdermal patch), bucally, or as an oral or nasal spray, depending on the location of the tumor. The pharmaceutical compositions may be in the form of particles comprising a biodegradable polymer and/or a polysaccharide jellifying and/or bioadhesive polymer, an amphiphilic polymer, an agent modifying the interface properties of the particles and a pharmacologically active substance. These compositions exhibit certain biocompatibility features which allow a controlled release of the active substance. See U.S. Pat. No. 5,700,486.

The pharmaceutically acceptable carriers and excipients useful in the disclosed methods are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate. Actual methods of preparing such dosage forms are known, or will be apparent, to those skilled in the art.

The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated. Multiple treatments are envisioned, such as over defined intervals of time, such as daily, bi-weekly, weekly, bi-monthly or monthly, such that chronic administration is achieved. Administration may begin whenever the suppression or prevention of disease is desired, for example, at a certain age of a subject, or prior to an environmental exposure.

The exact dose is readily determined by one of skill in the art based on the potency of the specific fraction, the age, weight, sex and physiological condition of the subject.

Additional agents can be administered, such as a cytokine, a chemokine, or a chemotherapeutic agent. These can be included in the disclosed pharmaceutical compositions. A cytokine can be administered, such an interleukin (IL) or an interferon, such as interferon (IFN), such as IL-1β, IL6, IL-10, IFN-α, IFN-β or IFN-γ. In one example, for the prevention and treatment of tumors, surgical treatment can be administered to the subject. In one example, this administration is sequential. In other examples, this administration is simultaneous.

Examples of chemotherapeutic agents are alkylating agents, antimetabolites, natural products, or hormones and their antagonists. Examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine). Examples of antimetabolites include folic acid analogs (such as methotrexate), pyrimidine analogs (such as 5-FU or cytarabine), and purine analogs, such as mercaptopurine or thioguanine. Examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocycin C), and enzymes (such as L-asparaginase). Examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide). Examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Examples of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol. Non-limiting examples of immunomodulators that can be used include AS-101 (Wyeth-Ayerst Labs), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

This disclosure is illustrated by the following non-limiting examples:

EXAMPLES

Example 1

Production of a Soluble Fraction

Urinary Bladder Matrix Preparation: Porcine urinary bladders were acquired from market weight pigs (110-130 kg) as a byproduct of routine commercial production The extracellular matrix from this tissue referred to as UBM was prepared as previously described (Freytes et al, J Biomed Mater Res B Appl Biomater 2006; 78:327-33). Briefly, the tunica serosa, tunica muscularis externa, tunica submucosa, and most of the tunica muscularis mucosa were mechanically removed and the luminal urothelial cells of the tunica mucosa were dissociated by rinsing in sterile water. The remaining tissue consisted of the basement membrane, the subjacent tunica propria of the tunica mucosa, and any resident cells in those layers. The matrix was decellularized by agitation in 0.1% peracetic acid with 4% ethanol for 2 hours at high speed followed by extensive rinsing with phosphate-buffered saline (PBS) and sterile water. Decellularization was verified using 4'-6-diamidino-2-phenylindole (DAPI, Fisher Scientific, Waltham, Mass.) nuclear staining and quantification of remnant DNA (Crapo et al., Biomaterials 2011; 32:3233-43). The UBM was then lyophilized into a dry sheet and either milled into particulates using a Wiley Mill with a #60 mesh screen (Gilbert et al., Biomaterials 2005; 26:1431-5) or left as a dry sheet.

Esophageal ECM preparation: Porcine esophagi were acquired from market weight pigs (110-130 kg) as a byproduct of routine commercial production. The extracellular matrix from this tissue referred to as eECM was prepared as previously described (Keane et al, Tissue Eng Part A 2015; 21(17-18):2293-30). Porcine esophagi were stored at −20° C. and thawed overnight at 4° C. eECM was prepared by mechanically separating the mucosa and submucosa layers from the subjacent muscularis externa. The mucosa and submucosa were decellularized with the following steps: 1% trypsin (Amresco)/0.05% EDTA (Sigma) for 1 h at 37° C. on a rocker plate, Type 1 water for 15 minutes, 1M sucrose (Sigma) for 30 min, Type 1 water for 30 min, 3.0% Triton X-100 (Sigma) for 48 h, Type 1 water for 15 minutes, PBS for 15 min, 10% sodium deoxycholate (Sigma) for 4 h, Type 1 water for 30 min, 0.1% peracetic acid (PAA) (Rochester Midland) in 4% ethanol for 4 h, 100 U/mL DNase (Invitrogen) for 2 h on a rocker plate, and 15 min washes of PBS, Type 1 water, PBS, and Type 1 water to create eECM. All decellularization steps were performed at 300 rpm at room temperature on a shaker plate.

Small Intestinal Submucosa (SIS) ECM Preparation: Porcine small intestines were acquired from market weight pigs (110-130 kg) as a byproduct of routine commercial production. SIS was prepared by mechanically removing the superficial layers of the tunica mucosa, tunica serosa, and tunica muscularis externa from the intact small intestine, leaving the submucosa, muscularis mucosa, and basilar stratum compactum intact in accordance with a previously established decellularization protocol (Badylak et al. Biomaterials 1999; 20:2257). SIS was then subjected to 0.1% peracetic acid in 4.0% ethanol for 4 h at room temperature with agitation on a shaker plate at 300 rpm.

Dermis ECM Preparation: Full thickness skin from the porcine dorsolateral flank was harvested immediately after euthanasia. The extracellular matrix from this tissue referred to as dermis was prepared as previously described (Reing et al. Biomaterials. 2010; 31(33):8626-33). The full thickness skin sheets were cut into 6 cm×10 cm rectangles and subsequently split to remove subcutaneous fat, connective tissue and the overlying epidermis, leaving the reticular and papillary layers of dermis. Consecutive washes with Trypsin, hydrogen peroxide, Triton X-100 and EDTA, and peracetic acid achieved decellularization.

Testicular ECM preparation: Porcine testes were purchased from Tissue Source (Lafayette, Ind.), and stored at −20° C. Frozen testes were thawed in lukewarm running water, sliced to 4 mm, rinsed in type I water which was replaced every 20-60 minutes until water remained colorless, decapsulated, and agitated in a 0.02% and 0.05% EGTA solution at 37° C. for 2.5 hours. Tissue was then agitated at room temperature in 0.075% sodium dodecyl sulfate (SDS) for 24 hours; SDS solution was replaced with fresh solution at 12 hours. Tissue was rinsed with Type 1 water for 20 minutes, followed by PBS for 20 minutes, Type 1 water for 20 minutes, and PBS for 20 minutes. Tissue was then agitated at room temperature for 2 hours in 1% TX-100 and rinsed again with water/PBS/water/PBS for 20 minutes each. Material was then washed in 0.1% PAA and 4% EtOH for 2 hours and rinsed with water/PBS as described above.

Preparation of Pepsin Solubilized ECM: ECM was enzymatically digested as previously described (Freytes et al., Biomaterials 2008; 29: 1630-7) with pepsin by mixing lyophilized, powdered UBM or eECM (10 mg/mL) and pepsin (1 mg/mL) in 0.01 M HCl (pH 2.0). This solution was stirred at room temperature for 48 hours. After stirring, the UBM slurry was neutralized to a pH of 7.4 in 1×PBS (137 mM NaCl, 2.7 mM KCl, 12 mM Phosphate, Fisher Scientific, Waltham, Mass.) to inactivate the pepsin and prepare the material for cell culture assays. A solution of pepsin (1 mg/mL) in 0.01M H Cl, treated in the same fashion as the UBM sample, served as the control condition for all experiments. All materials were stored at −80° C. until use.

Fractionation of Pepsin Solubilized ECM: Neutralized ECM digest was incubated at 37° C. to induce gelation. The ECM hydrogel was then centrifuged at 25,000×g for 30 minutes to compress the insoluble, structural components of the scaffold into a pellet, leaving a clear supernatant above the pellet. The gel pellet containing the structural components was collected and resuspended to the starting volume in 1×PBS. Due to the insolubility of the gel pellet, the gel pellet suspension was vigorously pipetted through a 10 µl pipet tip to homogenize the material as much as possible. The homogenized suspension was stored at −80° C. until use. The clear supernatant containing the soluble components was removed and lyophilized to dryness. The dried supernatant was rehydrated in 10% of its original volume with sterile water to drive the PBS concentration from 1× to 10λ. The rehydrated soluble components were centrifuged at 20,000×g to clarify the solution. The supernatant from this final spin was removed, diluted to the starting volume, and stored at −80° C. until use. Dilution to the starting volume for both fractionated components allowed direct comparison of the biological activity of the fractions using the same dilution factor for all materials.

Preparation of ECM Soluble Fraction by Salt Extraction: 10 mg of UBM was incubated in 10 ml of 0.154 molar NaCl in a conical container for 24 hours at 22° C. on an orbital rocker. After incubation, the sample was centrifuged at 10,000×g for 10 minutes, and the supernatant was transferred to a new tube. The supernatant was filtered through a 0.22 micron filter, and lyophilized. The lyophilized saline soluble fraction was resuspended in 10 ml ultrapure water and desalted using a 10 kDa molecular weight cutoff column by centrifuging at 5,000×g for 30 minutes. The eluate was discarded, and the volume of desalted soluble fraction was adjusted to 1 ml using ultrapure water, yielding a UBM saline soluble fraction (UBM-SF) solution designated as a 10× concentration.

Example 2

Results

Figure 1B:
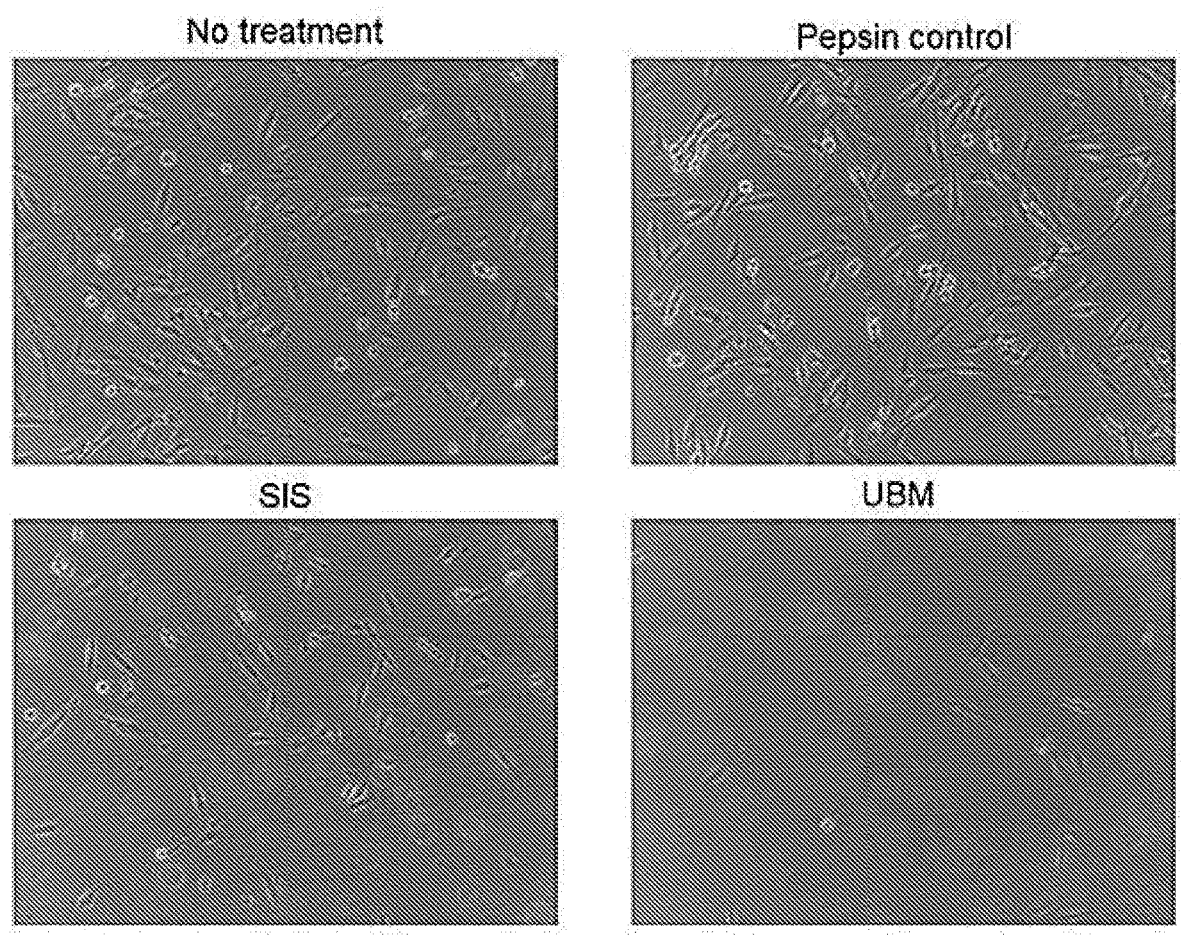

The soluble fraction of pepsin-solubilized ECM modulated primary human glioma cell phenotype. Primary human glioma cells react to pepsin solubilized ECM from various source tissues within 24 h. These effects cannot be attributed to the presence of pepsin, as shown by the pepsin control matching the media control. SIS and UBM treatment cause a dramatic reduction in viable glioma cells, suggesting these ECM environments decrease the proliferation rates or glioma cells, cause them to undergo cell death, or both (FIG. 1).

Figure 2:
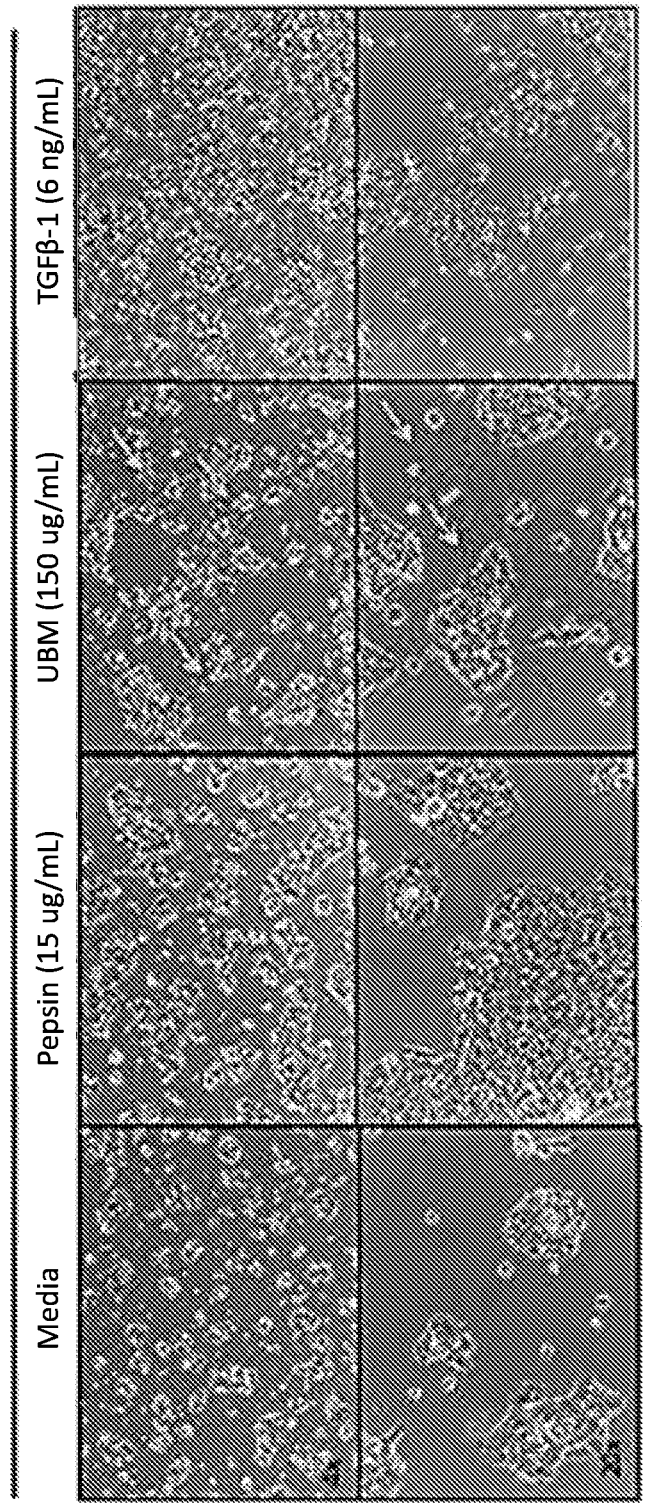
FIG. 2: ECM hydrogel modulates cancer cell phenotype. Solubilized ECM hydrogel, specifically urinary bladder matrix (UBM) hydrogel induce cancer cells to form "cellular bridges," a phenotype that is distinct from the negative control pepsin and media. The phenotype is also distinct from TGFβ positive control, a known inducer of cancer cell migration.

ECM hydrogel modulated esophageal cancer cell phenotype. The OE33 esophageal cancer cells showed a striking phenotypic change after 24 h of treatment with pepsin solubilized UBM with the appearance of "cell bridges" (indicated by arrows) which were absent in the pepsin or media control. The phenotype is also distinct from TGFβ-1 positive control, a known inducer of cancer cell migration (FIG. 2).

ECM hydrogel decreased esophageal adenocarcinoma proliferation. The effect of solubilized UBM or eECM on Het-1A, CP-A, and EAC (OE33, SK-GT-4) cell proliferation was evaluated using a BrdU proliferation assay. Representative graphs of the biological replicates (n=3) are shown (FIG. 3A-D). UBM-ECM decreased the proliferation of OE33 cancer cells compared to pepsin control (p=0.0008, FIG. 3C), but showed no change in proliferation compared to pepsin control for Het-1A (FIG. 3A), CP-A cells (FIG. 3B), or SK-GT-4 cells (FIG. 3D). eECM decreased proliferation of all cell types compared to pepsin control: Het-1A (p<0.0001), CP-A (p<0.0001), OE33 (0.0003), and SK-GT-4 (p<0.0001) (FIGS. 3A-3D).

Comparing ECM tissue types, eECM significantly decreased proliferation of all cell types compared to UBM-ECM for Het-1A (p<0.0001, FIG. 3A), CP-A (p<0.0001, FIG. 3B), and SK-GT-4 (p<0.0001, FIG. 3D). There was no difference between eECM and UBM-ECM to decrease OE33 cell proliferation (FIG. 3C). Thus, esophageal ECM was of particular use to treat esophageal cancer.

Pepsin solubilized UBM and eECM increased metaplastic cell apoptosis (FIG. 4A-4D). The effect of solubilized ECM on apoptosis was determined using a dual stain of propidium iodide (PI) and Annexin V. The fold change of early and late apoptotic cells with pepsin solubilized UBM or eECM treatment compared to pepsin is shown for Het-1A (FIG. 4A), CP-A (FIG. 4B), OE33 (FIG. 4C), and SK-GT-4 (FIG. 4D). For CP-A cells, UBM-ECM treatment increased late apoptosis (p=0.0095) compared to pepsin control, and eECM treatment trended toward increased late apoptosis compared to pepsin control (p=0.0756). UBM and eECM did not show differences for early or late apoptosis in Het-1A, OE33, or SK-GT-4 cells compared to pepsin control. The results showed that UBM increased apoptosis of an esophageal cancer precursor cell.

Figure 5:
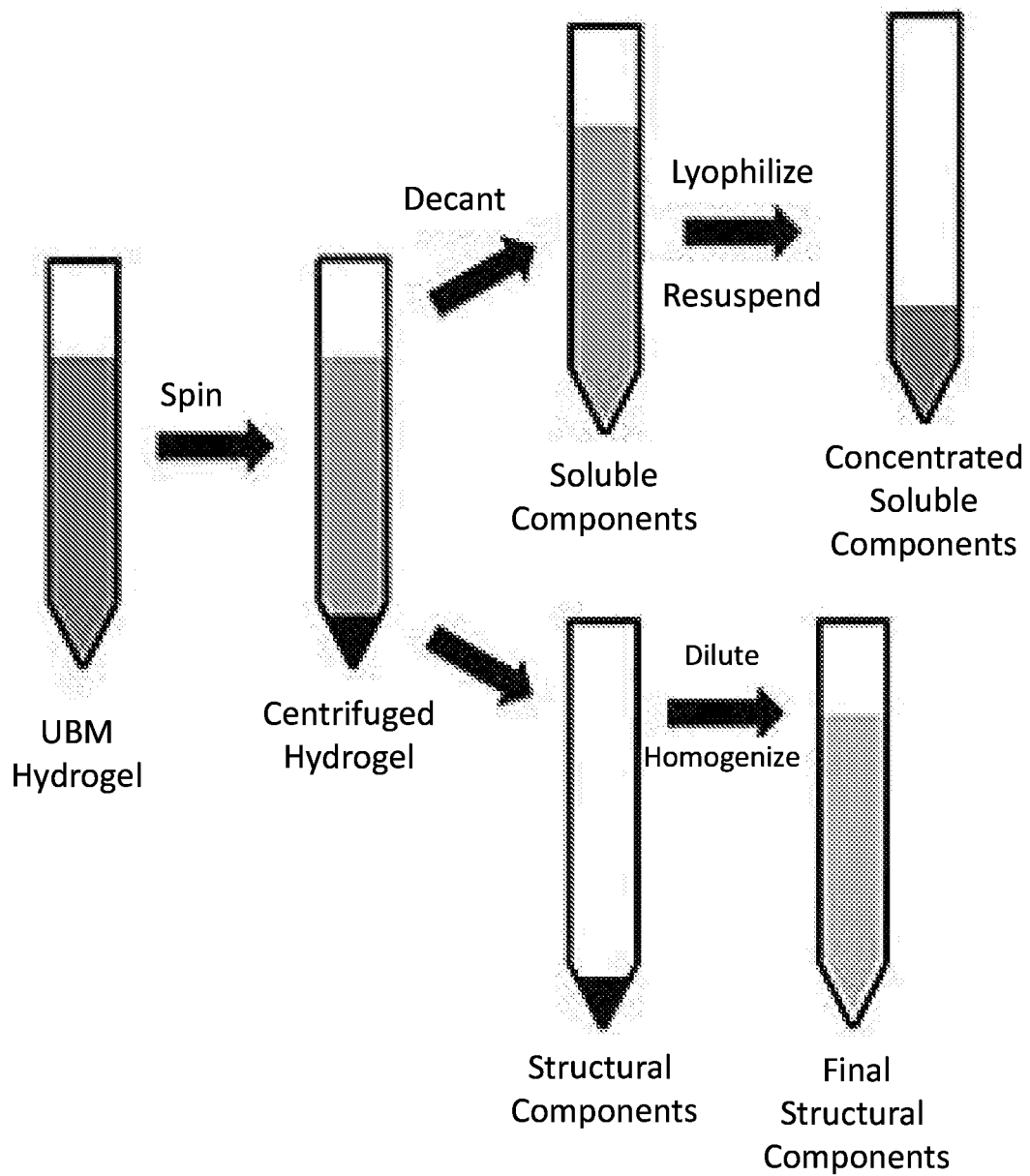
FIG. 5: Schematic diagram illustrating the methodology for the preparation of soluble and structural fractions from ECM bioscaffolds.

ECM hydrogels can be separated into constituent parts. In a specific non-limiting example, this figure presents one method of dividing a UBM hydrogel into structural and soluble components, or into high-density and low-density components, through centrifugation (FIG. 5). Neutralized ECM digest was incubated at 37° C. to induce gelation. The ECM hydrogel was then centrifuged at 25,000×g for 30 minutes to compress the insoluble, structural components of the scaffold into a pellet, leaving a clear supernatant above the pellet. The gel pellet containing the structural components was collected and resuspended to the starting volume in 1×PBS. Due to the insolubility of the gel pellet, the gel pellet suspension was vigorously pipetted through a 10 µl, pipet tip to homogenize the material as much as possible. The homogenized suspension was stored at −80° C. until use. The clear supernatant containing the soluble components was removed and lyophilized to dryness. The dried supernatant was rehydrated in 10% of its original volume with sterile water to drive the PBS concentration from 1× to 10×. The rehydrated soluble components were centrifuged at 20,000×g to clarify the solution. The supernatant from this final spin was removed, diluted to the starting volume, and stored at −80° C. until use. Dilution to the starting volume for both fractionated components allowed direct comparison of the biological activity of the fractions using the same dilution factor for all materials.

Figure 6:
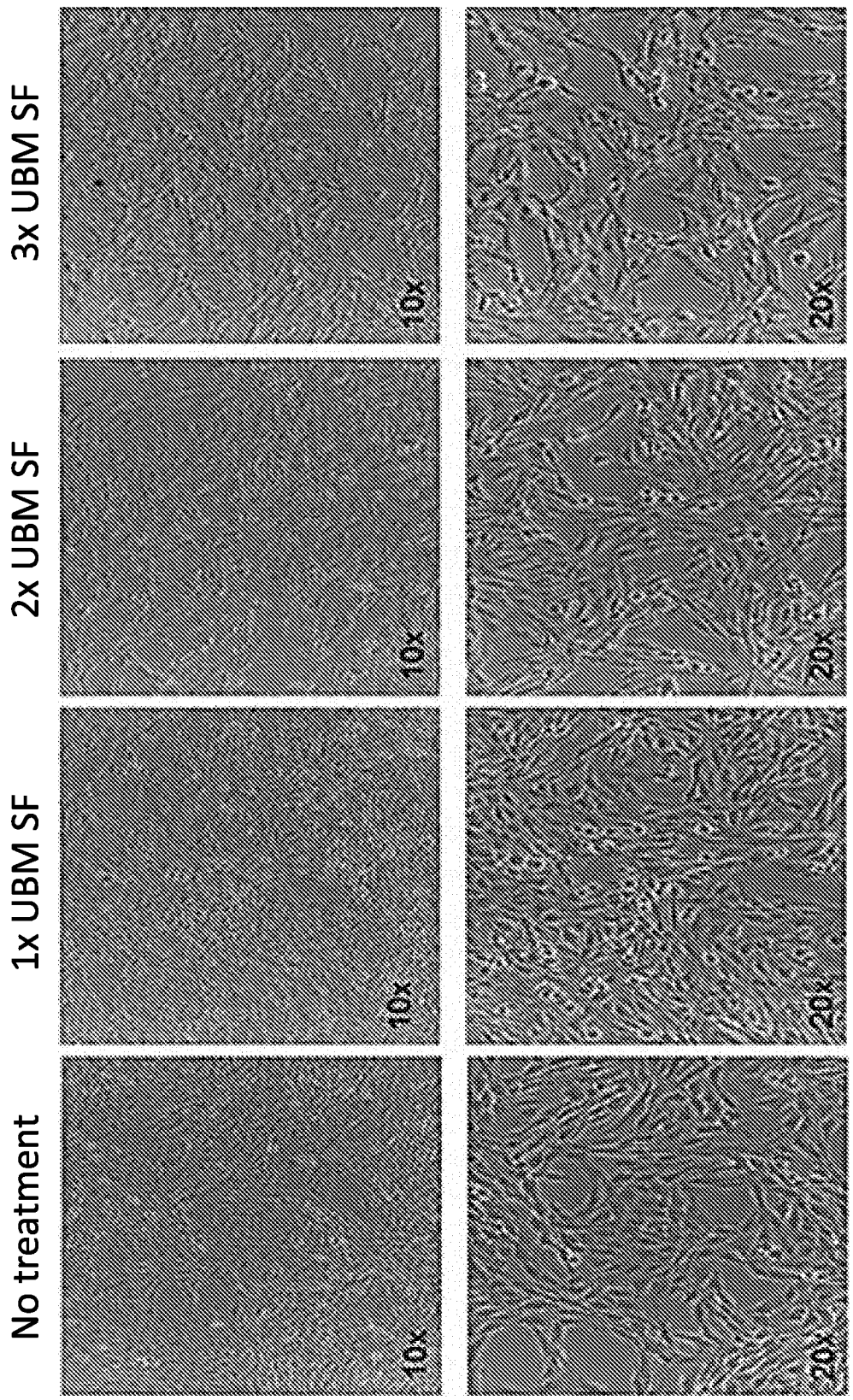
FIG. 6: Soluble ECM bioscaffolds do not affect non-neoplastic cell growth. Human fetal microglia were treated with increasing concentrations of UBM soluble fraction for 24 r

Non-neoplastic microglia cell line was unaffected by UBM-SF. CHME5 cells treated with increasing concentrations of UBM-SF appeared to grow normally. Thus, non-neoplastic cell types were not harmed (and often benefitted) by the presence of non-neoplastic ECM added to culture media (FIG. 6).

Figure 7:
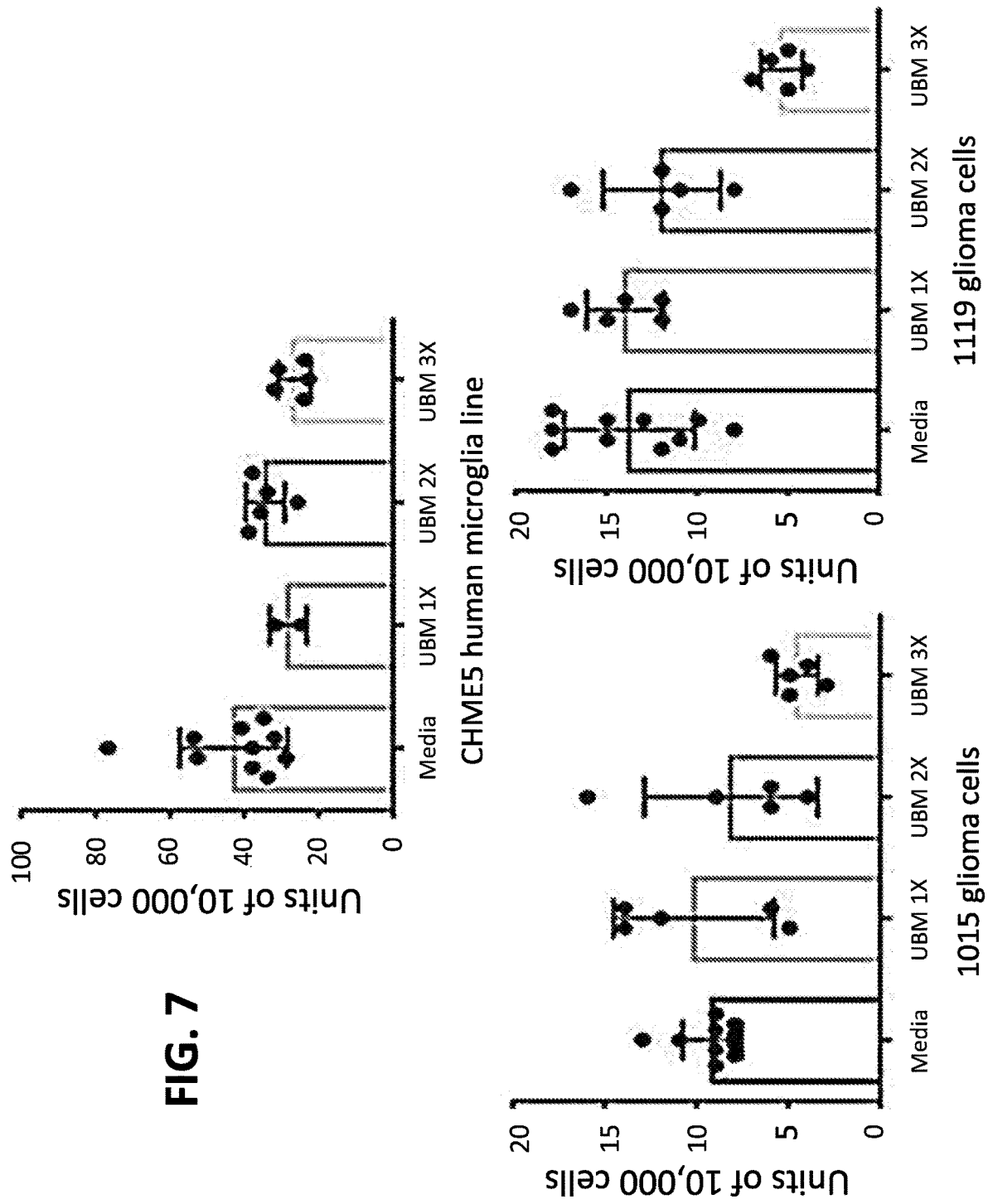
FIG. 7: Quantification of cell growth after treatment with ECM soluble fraction.

UBM saline soluble fraction (UBMSF) decreased glioma cell count in a dose-dependent manner while supporting microglia cells. Cell count data showed that increasing concentrations of UBM-SF decreased the total cell number of both high grade (1015) and low grade (1119) primary human glioma cells while a microglia cell line (CHME5) grows unaffected, suggesting that. UBM-SF possesses oncolytic activity, as compared to pancytotoxic activity (FIG. 7). See also FIGS. 10, 20, 21 and 23-25.

Figure 8:
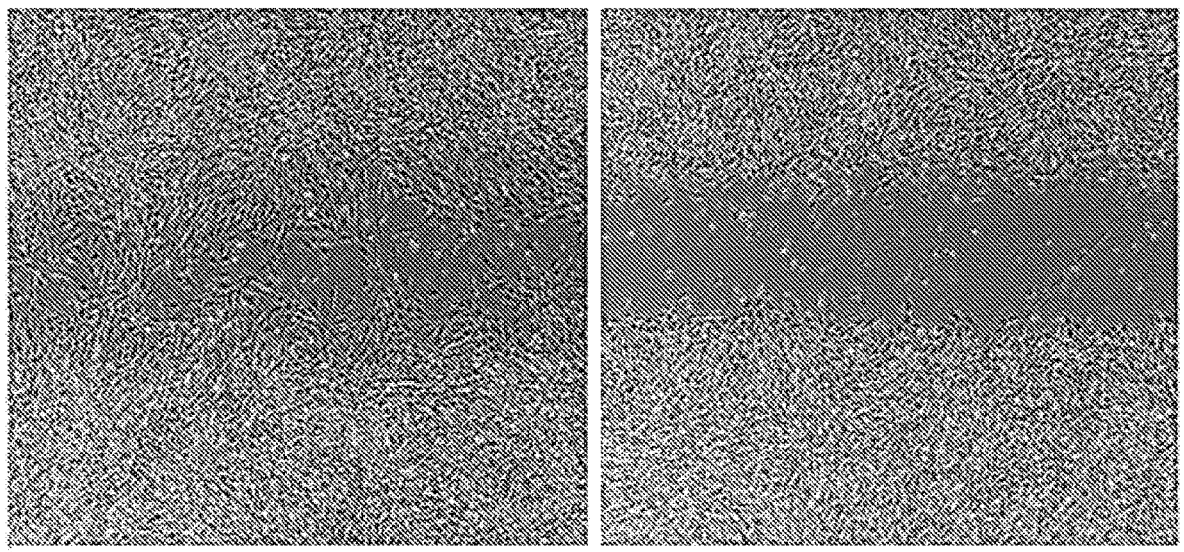
FIG. 8: Soluble fraction of ECM bioscaffolds inhibit migration of glioma cells. Scratch assay. Low grade primary human glioma cells (1119) were treated with the soluble fraction from UBM. After 24 hrs of treatment, cells showed reduced capacity to migrate compared to the no treatment control.

UBM-SF decreased glioma cell migration. In a classical scratch assay (Liang et al. Nature Protocols. 2007; 2:329-333), glioma cells exposed to UBM-SF exhibit decreased migration within 24 hours compared to a media control (FIG. 8). See also FIGS. 14A-14D, which show a scratch assay.

Saline soluble fraction of ECM bioscaffolds and membrane bound vesicle (MBVs) derived from ECM bioscaffolds inhibited esophageal cancer cell viability. The effect of saline soluble fraction of ECM bioscaffolds and MBV on viability was assessed using an MTT assay. OE33 and OE19 cells showed a decrease in viability with UBM SFF, collagenase MBV (cMBV) and elastase MBV (eMBV) compared to control (FIG. 9).

Figure 10:
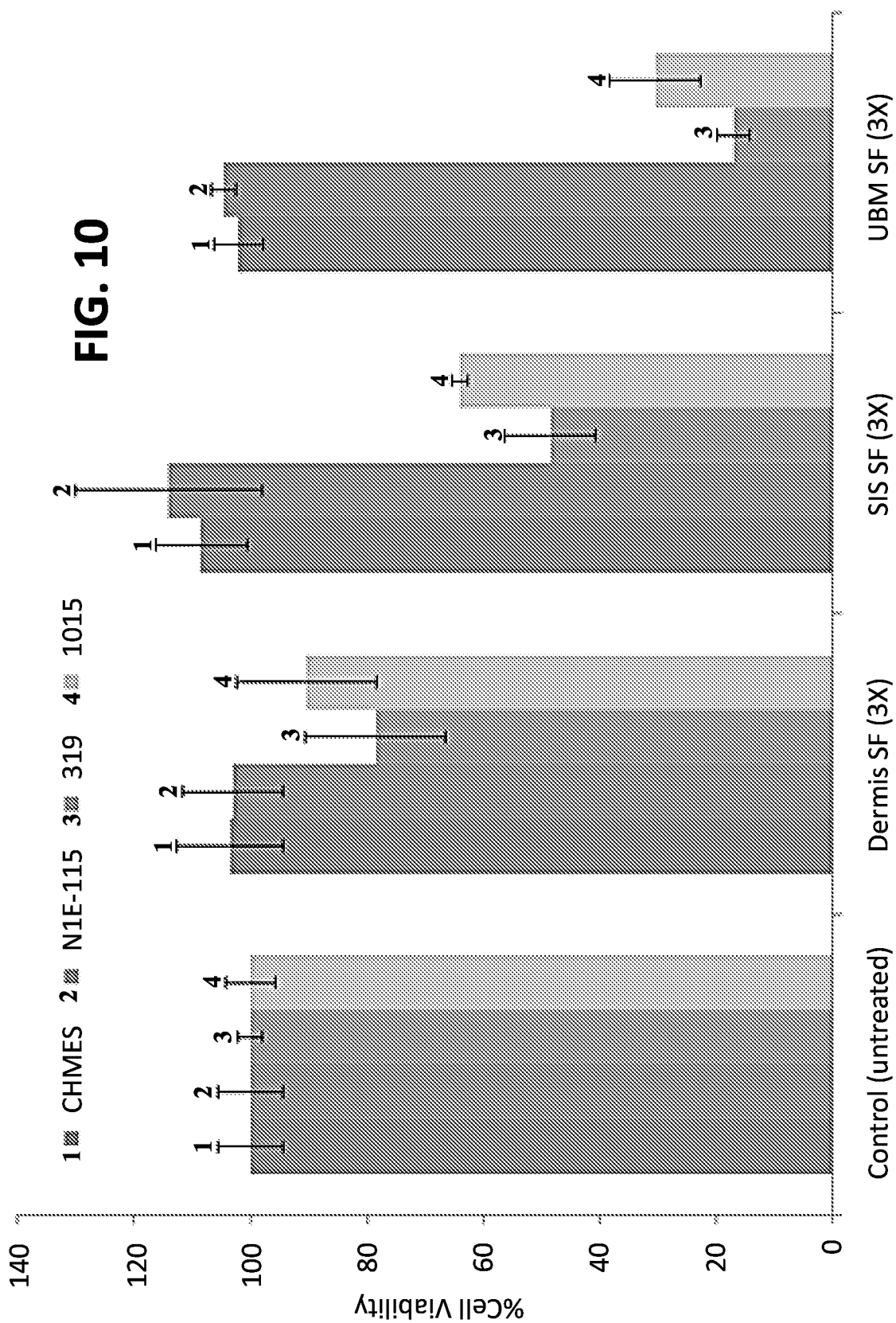
FIG. 10. Soluble fraction of Urinary Bladder ECM (UBM-SF) markedly decreased glioma cell viability. UBM-SF was more potent that the soluble fraction of small intestinal submucosa (SIS-SF) or the soluble fraction of dermal ECM (dermis-SF).

Saline soluble fractions of ECM bioscaffolds decreased glioma but not non-neoplastic cell viability. Glioma cell viability was decreased by soluble fractions of dermal ECM, SIS, and UBM, in order of increasing potency. These same ECM components did not decrease the viability of microglia cells (CHME5) or neuroblasts (N1E-115). This suggests UBM-SF possesses preferential oncolytic activity, as compared to pancytotoxic activity (FIG. 10). Additional results are shown in FIGS. 7, 20, 21, and 23-25.

Figure 11:
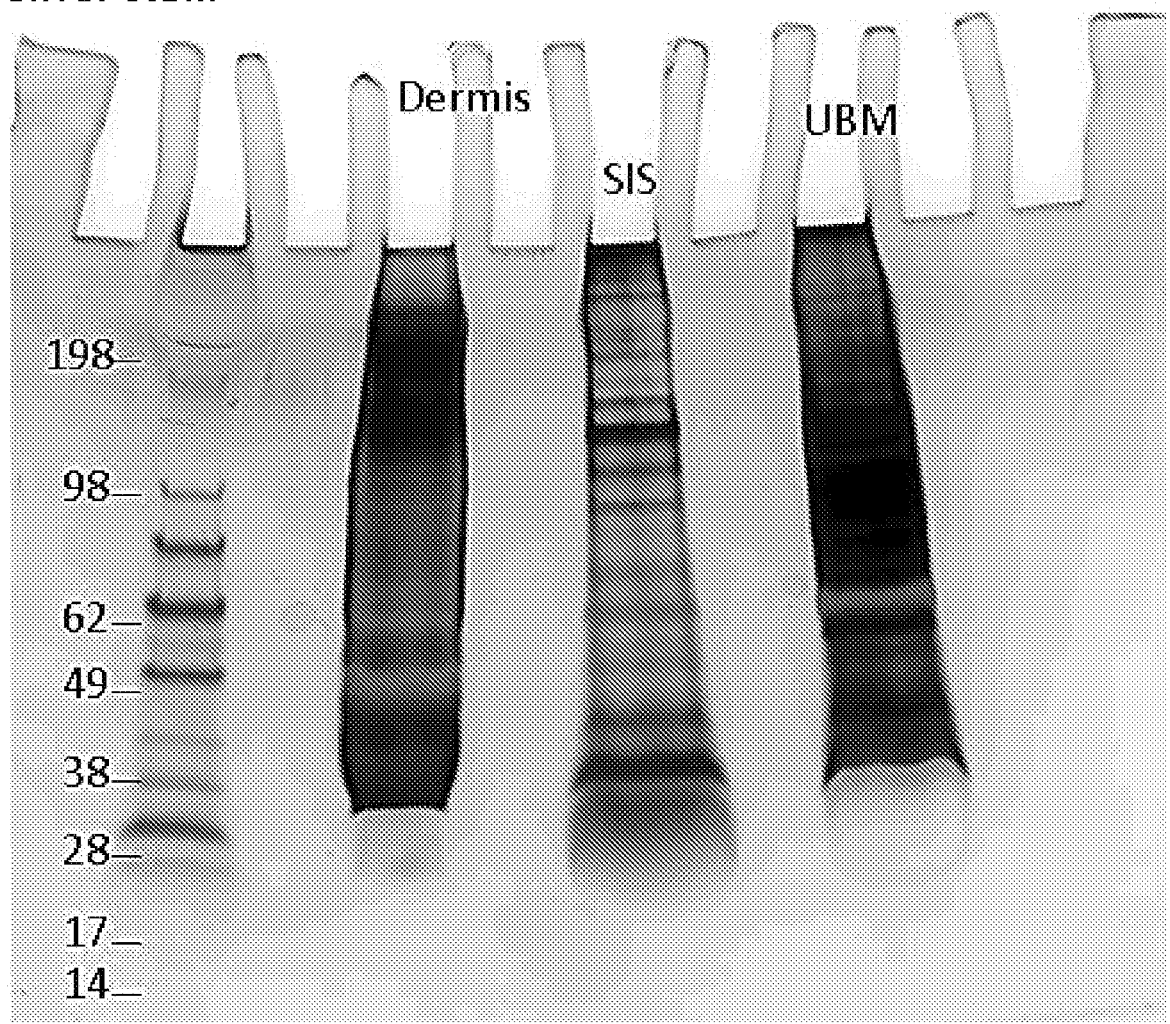
FIG. 11. Various source ECM provide distinct soluble fractions.

Protein composition of ECM environment is complex and varied by source tissue. The differential effects of source tissue ECM on cells can be explained, at least partially, by the differential protein compositions of those source tissues. As shown in FIG. 11, the protein signature is complex.

Figure 12A:
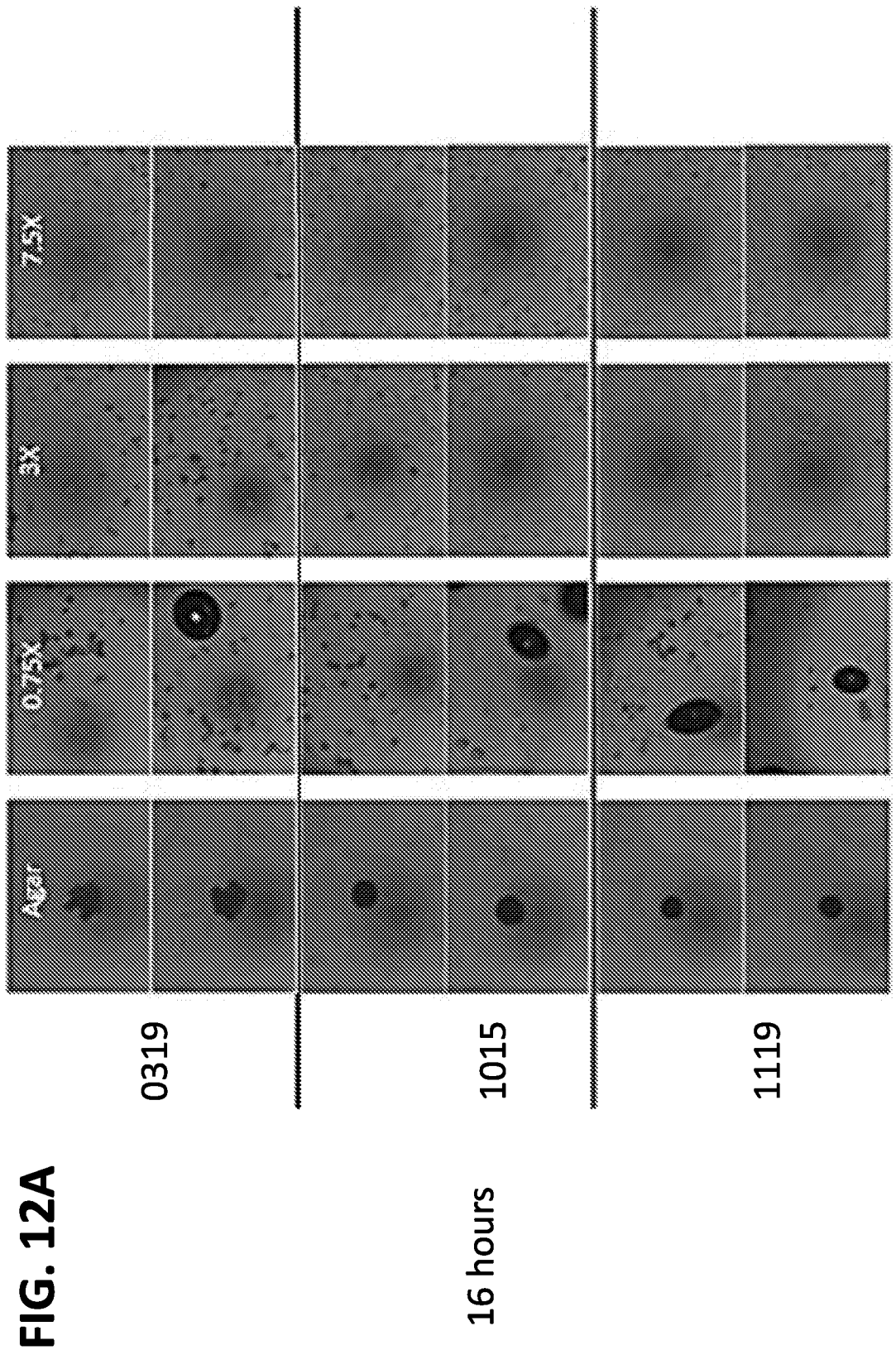
Figure 12B:
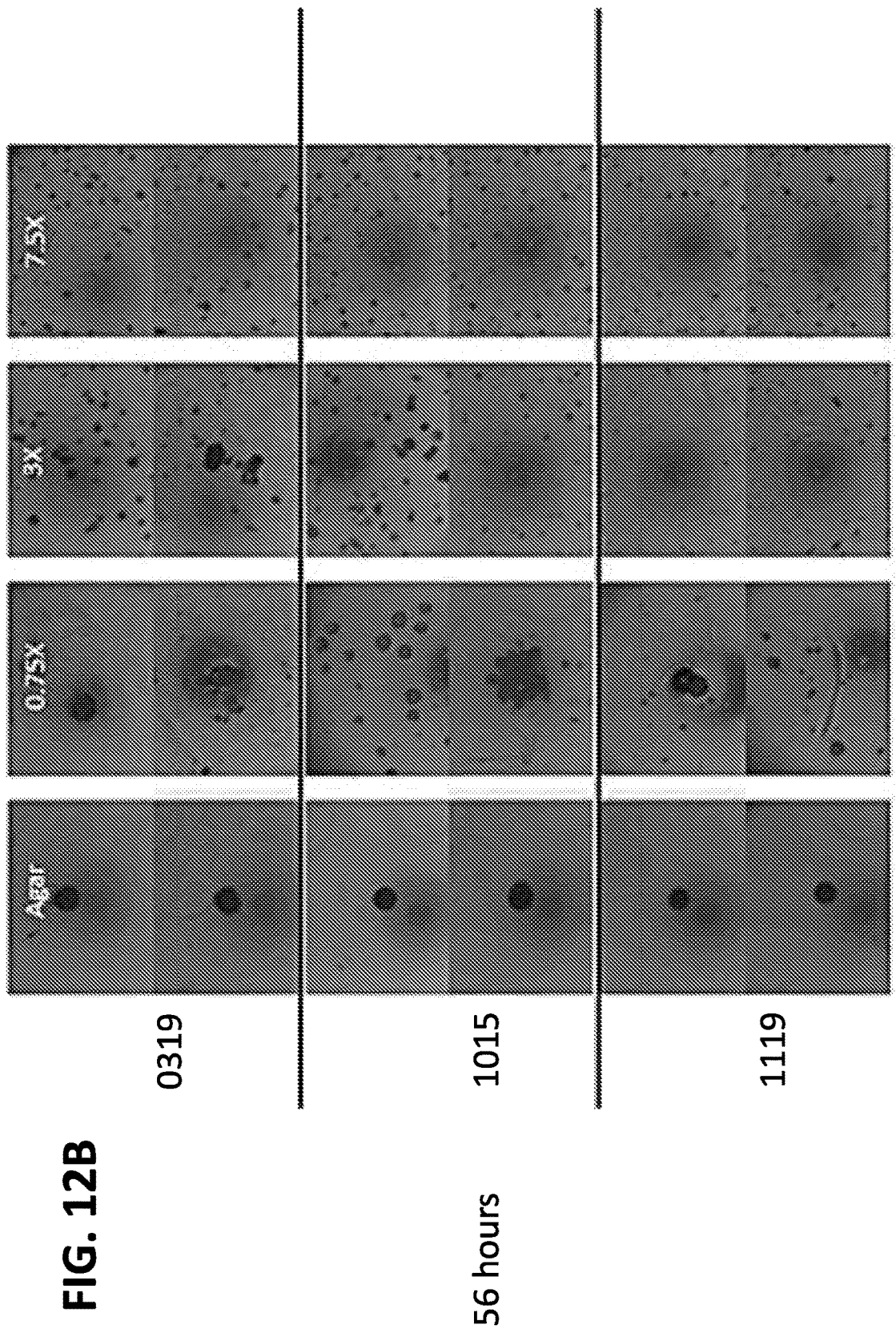
Figure 13:
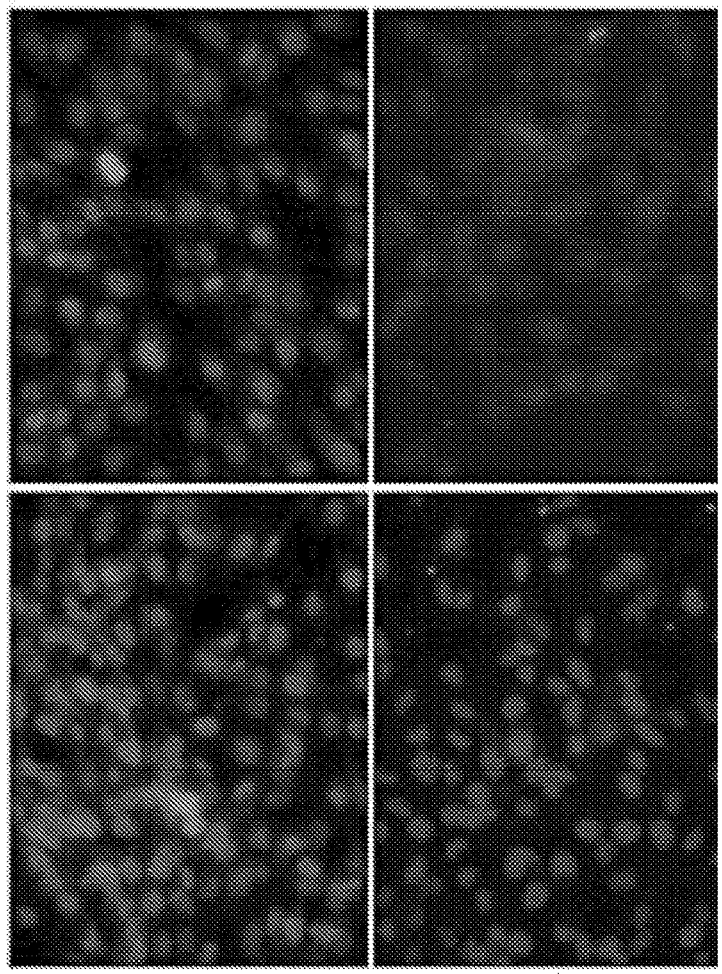
FIG. 13. Immunocytochemistry for Erk1/2 and pErk1/2 in 0319 cells after 24 hours of 3×UBM-SF treatment. UBM-SF increases phosphorylated ERK signaling in 0319 glioma cells. UBM-SF may decrease glioma cell proliferation through the MPAK/ERK pathway.

Glioma colony formation was abrogated by UBM-SF in a dose-dependent manner. Colony formation in soft agar (0.5%) is an art-accepted assay for in vitro screening of chemotherapeutic drugs. Results are shown in FIG. 12A-12C for N=2 of two high grade (0319, 1015) and one low grade (1119) primary human glioma cells. It was apparent that formation of a large colony occurred within 16 hours of cell plating in agar. However, this was interrupted in the presence of UBM-SF (FIG. 12A). At later time points this colony disruptive effect was dependent on the concentration of UBM-SF present and this trend held true for each glioma cell type tested (FIGS. 12B and 12C).

pERK1/2 was upregulated in glioma cells treated with UBM-SF. The oncolytic/oncostatic properties exhibited by UBM-SF can be explained by modulation of the MAPK/ERK pathway. As shown in FIG. 13, there is increased pERK1/2 in glioma cells after treatment with UBM-SF. The upregulation of pERK has been observed to decrease glioma cell proliferation (Chen et al. PLoS ONE. 2014; 9(1): e87281).

Figure 14A:
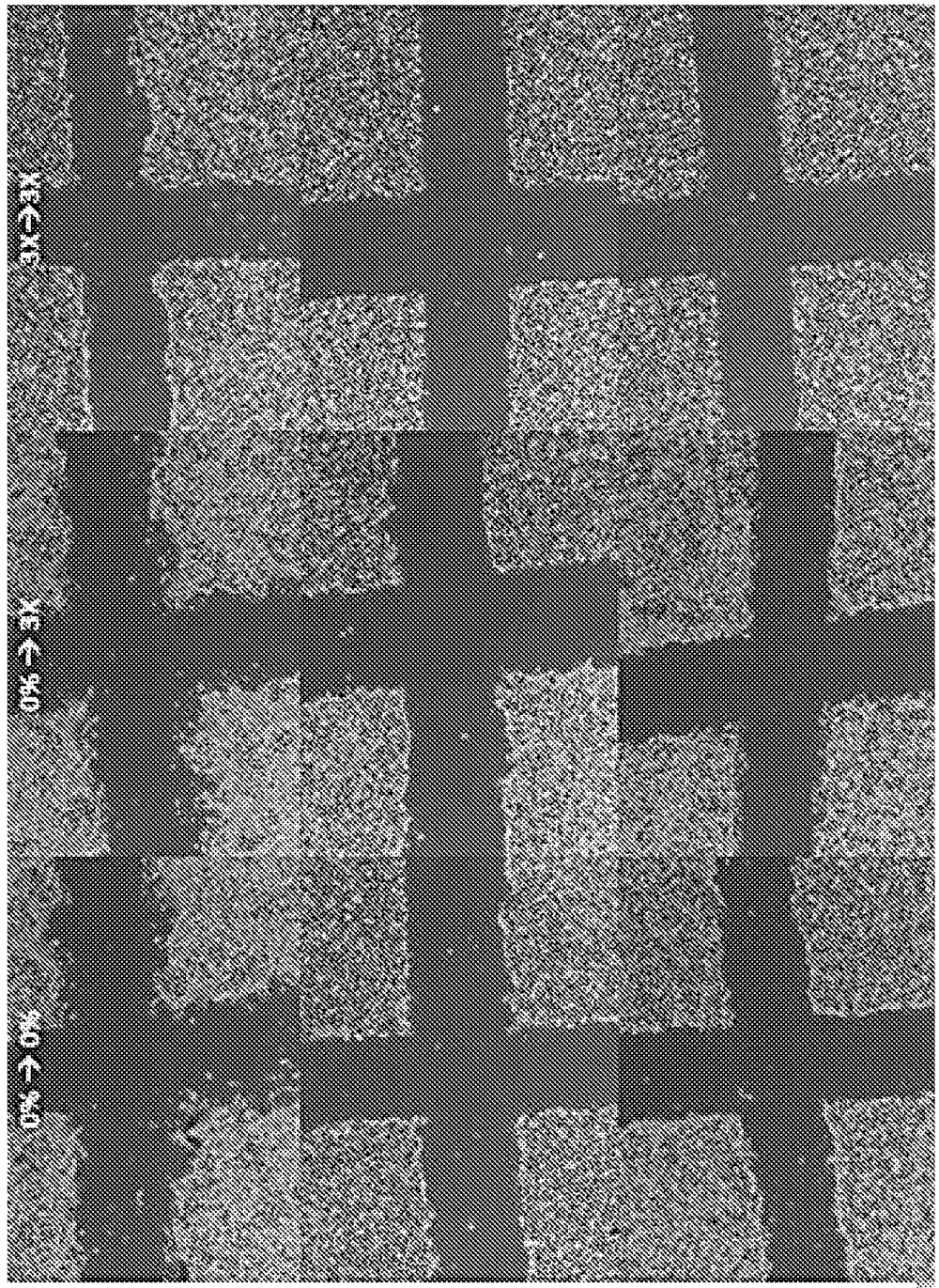
Figure 14B:
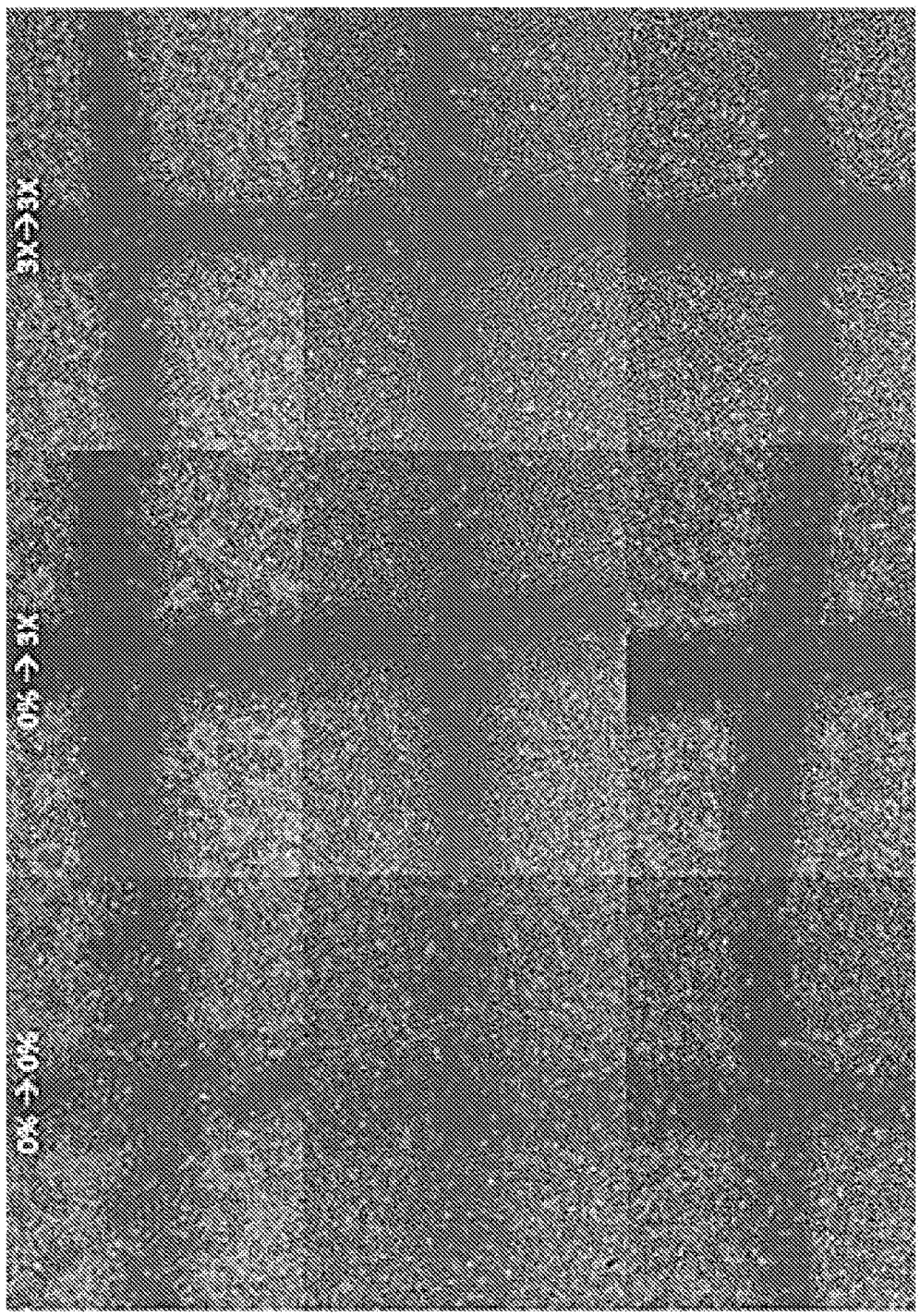

UBM-SF decreased glioma cell migration at early time points and causes cell death at later time points. Two high grade (0310, 1015) and one low grade (1119) glioma cell types were tested in a classical scratch assay (FIG. 14A-14D). Cells were pre-treated with serum free media with or without 3×UBM-SF, the scratch was introduced, and then treatment groups were introduced (corresponding to the first symbol, the right arrow "→", and the second symbol at the top of each column). 0% designates a serum-free media, and 3X indicates UBM-SF at a concentration of 3 mg/mL as measured by a spectrophotometer. At time 0, immediately after the scratch, all conditions were observed to be essentially identical (FIG. 14A). Twenty-four hours (24 h) later it was apparent that the cells given serum free media were migrating to fill the scratch much more rapidly than the cells exposed to UBM-SF (FIG. 14B). At 48 hours, certain groups given UBM-SF were obviously dead; cells in the media control continue to migrate and fill in the scratch. Cells given UBM-SF which were not dead had migration halted (FIG. 14C). At 96 hours after treatment, all glioma cells given UBM-SF are dead (FIG. 14D).

Figure 15:
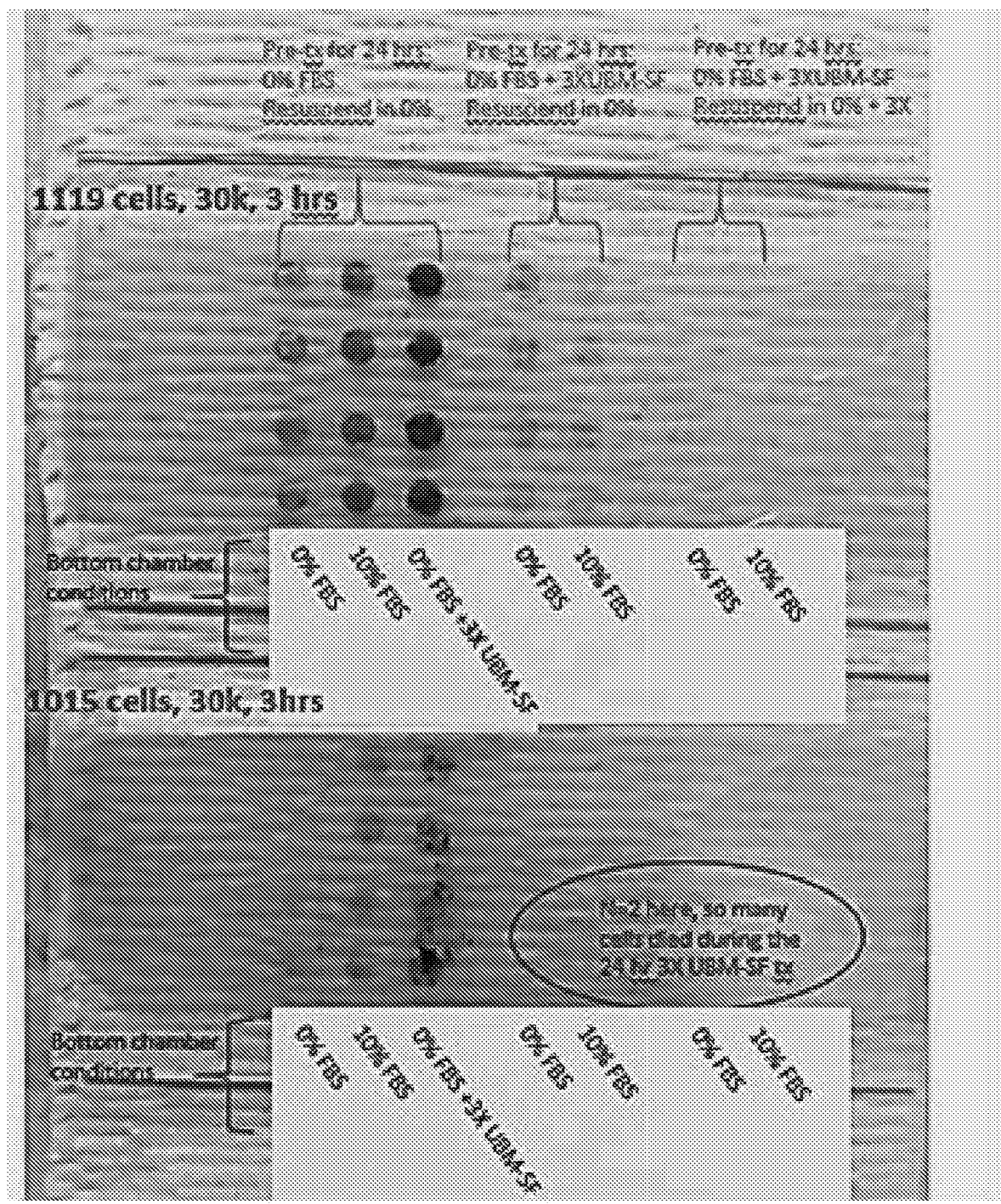
FIG. 15. Boyden Chamber Chemotaxis assay, N=4. In the absence of nutrients, glioma cells migrate toward UBM-SF. Glioma cell migration is dramatically reduced (almost non-existent) once exposed to UBM-SF.
Figure 16A:
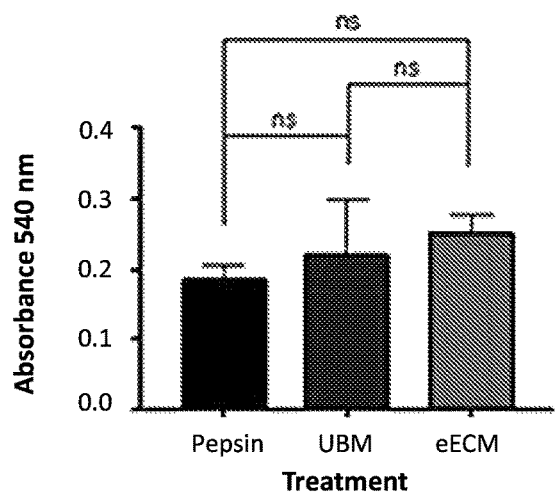
FIGS. 16A-16D. Solubilized ECM hydrogel inhibits esophageal cancer cell viability. The effect of solubilized ECM on normal, Barrett's, and EAC cell metabolic activity was evaluated using an MTT assay. UBM and eECM had no effect on metabolic activity of normal Het-la cell line (A) or CP-A cell line (B) compared to pepsin negative control. UBM decreased the metabolic activity of the OE33 (C) and SK-GT-4 (D) esophageal epithelial cancer cell line compared to pepsin negative control.
Figure 16B:
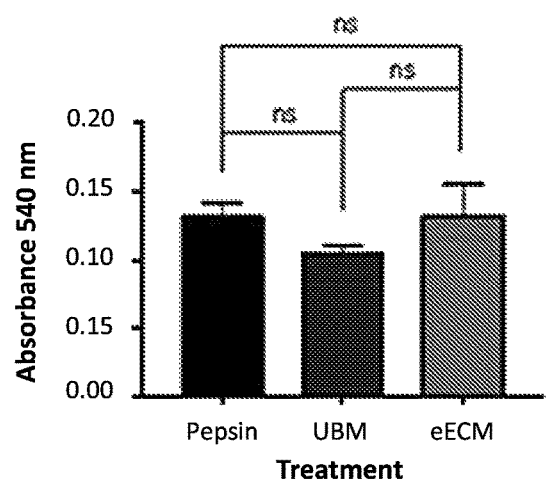
Figure 16C:
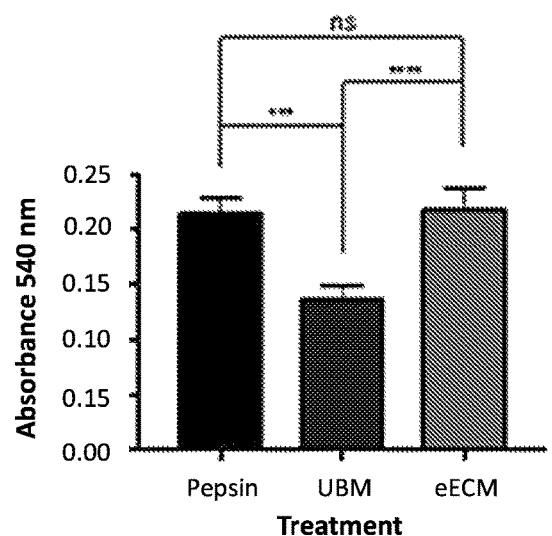
Figure 16D:
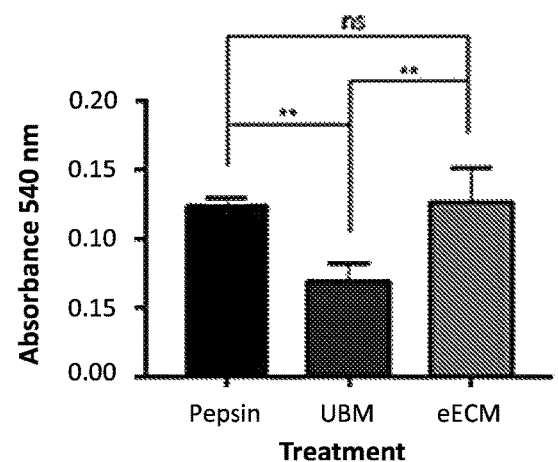

Migration of glioma cells mitigated by UBM-SF. Migration of glioma cells in the presence of UBM-SF was measured by a Boyden chamber assay. High grade 1015 cells were shown to be killed by UBM-SF at early time points and so no migration was observed. Low grade 1119 cells were shown to migrate less toward 10% FBS in the presence of UBM-SF when pre-treated with 0% FBS. Similarly, 1119 cells pre-treated with UBM-SF in 0% FBS media did not migrate at all toward 10% FBS, perhaps due to cell death (FIG. 15).

Pepsin solubilized ECM decreased esophageal adenocarcinoma cell metabolism. The effect of solubilized ECM on normal, Barrett's, and EAC cell metabolic activity was evaluated using an MTT assay. Representative graphs of the biological replicates (n=3) are shown (FIG. 16A-D). UBM and eECM did not affect the metabolic activity of Het-1A (FIG. 16A) or CP-A (FIG. 16B) cells compared to pepsin control. UBM decreased the metabolic activity of the OE33 (p=0.0001, FIG. 16C) and SK-GT-4 (p=0.0035, FIG. 23D) cells compared to pepsin control. UBM also decreased the metabolic activity of OE33 (p<0.0001, FIG. 16C) and SK-GT-4 (p=0.0024, FIG. 16D) cells compared to eECM.

Figure 17:
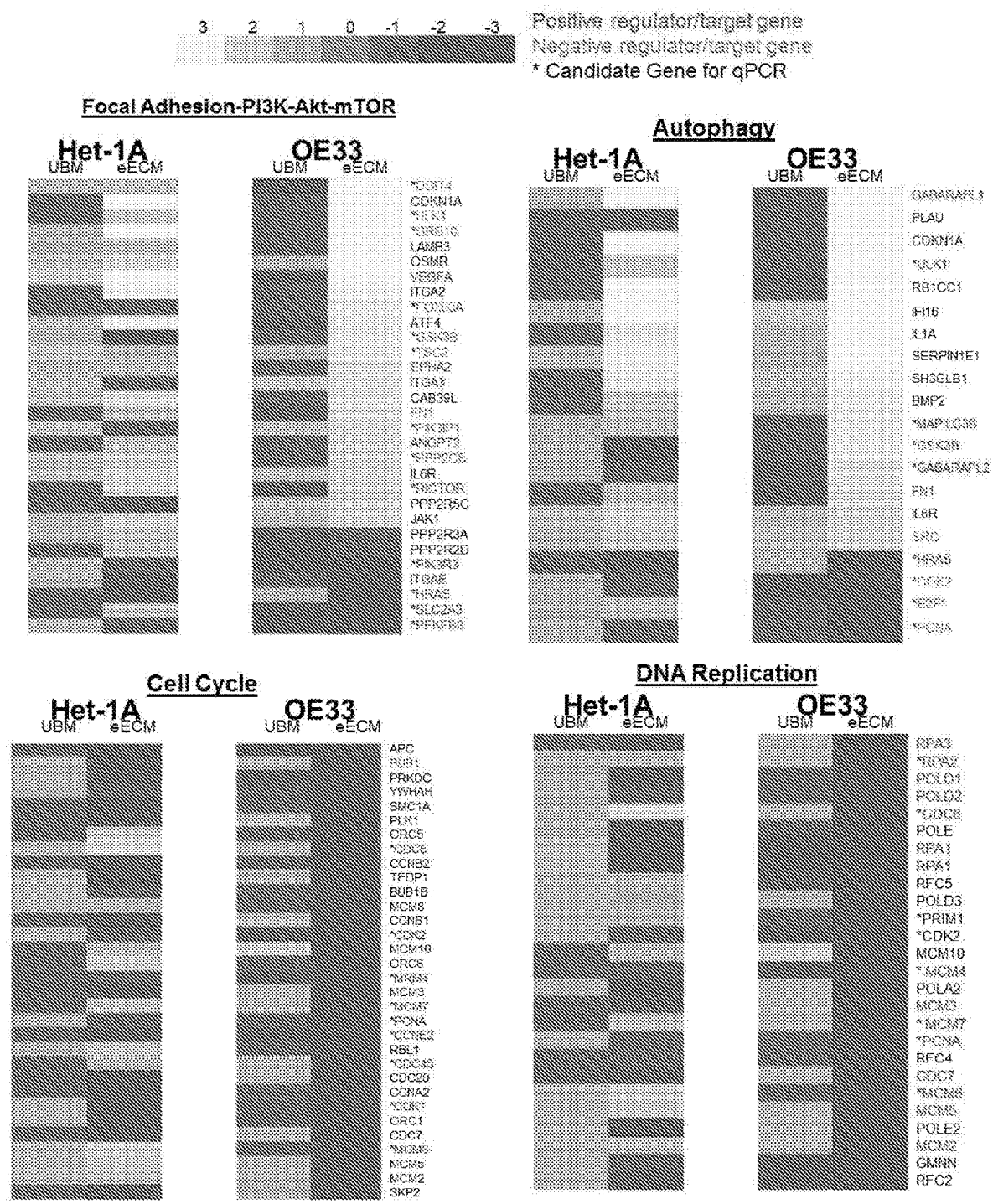
FIG. 17. UBM and eECM downregulate esophageal cancer cell signaling pathways—Whole transcriptomics analysis was used to identify the gene signature of Het-1A normal cells and OE33 esophageal epithelial cancer cells treated with UBM or eECM compared to pepsin negative control for 24 h. Genes that were differentially expressed (defined as greater or less than 2-fold change, with significance by one-way ANOVA p<0.05) were analyzed using unbiased pathway signaling analysis to identify top signaling pathways. Notably, the top differentially expressed pathways regulated by UBM and eECM treatment compared to pepsin negative control are related to cancer progression. eECM downregulated focal adhesion-PI3K-Akt-mTOR, Cell Cycle, and DNA replication, and upregulated autophagy (controlled cancer cell death) as shown by whole transcriptomics analysis and quantitative polymerase chain reaction (qPCR), with a net effect of downregulating esophageal cancer cell phenotype.
Figure 18:
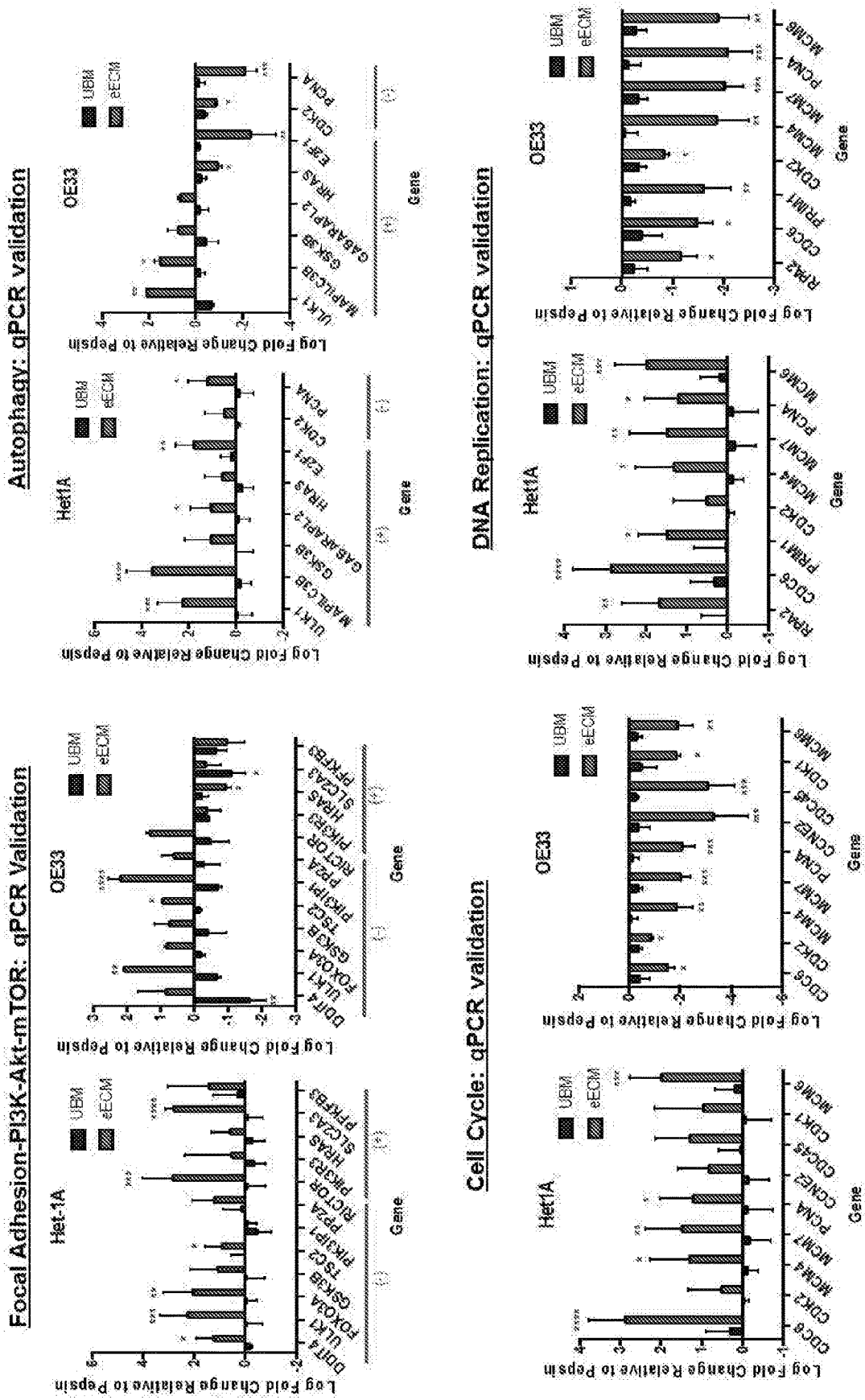
FIG. 18. qPCR validation of whole transcriptomics analysis. The results shown in FIG. 17 were validated using qPCR.

Pepsin solubilized UBM and eECM downregulated esophageal cancer cell signaling pathways. Whole transcriptome analysis was used to identify the gene signature of Het-1A normal cells and OE33 esophageal epithelial cancer cells treated with UBM or eECM compared to pepsin negative control for 24 h. Genes that were differentially expressed (defined as greater or less than 2-fold change, with significance by one-way ANOVA $p<0.05$) were analyzed using unbiased pathway signaling analysis to identify the top signaling pathways. Notably, the top differentially expressed pathways regulated by UBM and eECM treatment compared to pepsin negative control are related to cancer progression. eECM downregulated focal adhesion-PI3K-Akt-mTOR, Cell Cycle, and DNA replication, and upregulated autophagy (controlled cancer cell death), with a net effect of downregulating esophageal cancer cell phenotype (FIG. 17).

qPCR validation of whole transcriptomics analysis. The results shown in FIG. 17 were validated using qPCR (FIG. 18). For focal adhesion-PI3K-Akt-mTOR signaling in OE33 cells, eECM treatment upregulated 3 negative regulators (ULK1, TSC2, PIK3IP1) and downregulated 1 positive regulators (HRAS). UBM-ECM downregulated 1 negative regulator (DDIT4) and 1 positive regulator (SLC2A3). For focal adhesion-PI3K-Akt-mTOR signaling in Het1-A cells, eECM treatment increased 4 negative regulators (DDIT4, ULK1, FOXO3A, TSC2), and increased 2 positive regulators (RICTOR, SLC2A3).

For autophagy signaling in OE33 cells, eECM upregulated 2 positive regulators (ULK1, MAPILC3B) and downregulated 4 negative regulators/genes (HRAS, E2F1, CDK2, PCNA). For autophagy signaling in Het-1A cells, eECM increased tumor suppressor ULK1, proliferation markers PCNA and E2F1, and autophagy related genes MAPILC3B and GABARAPL2.

For the Cell Cycle and DNA replication pathways, many genes overlapped. For cell cycle signaling, eECM downregulated nine positive regulators in OE33 cells (CDCl6, CDK2, MCM4, MCM7, PCNA, CCNE2, CDCl45, CDK1, MCM6), and upregulated five positive regulators in the Het-1A cells (CDCl6, MCM4, MCM7, PCNA, MCM6). For DNA replication signaling in OE33 cells. eECM downregulated eight positive regulators (RPA2, CDCl6, PRIM1, CDK2, MCM4, MCM7, PCNA, MCM6) and upregulated seven positive regulators in Het-1A cells (RPA2, CDCl6, PRIM1, MCM4, MCM7, PCNA, MCM6).

Figure 19A:
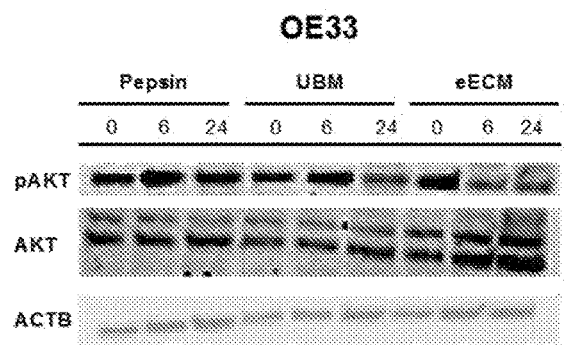
FIGS. 19A-19B. UBM and eECM downregulate OE33 AKT phosphorylation and increase Het-1A AKT phosphorylation. Western blot was performed on OE33 and Het-1A cells treated with pepsin, UBM, and eECM for 0, 6, or 24 h for pAKT, a positive regulator of cancer cell proliferation, cell metabolism, and cell survival. OE33 cells and Het-1A cells showed no change in pAKT in the pepsin control. OE33 cells show a downregulation in pAKT expression with UBM-ECM treatment at 24 h, and a downregulation in pAKT expression with eECM treatment at 6 and 24 h (FIG. 26A). In contrast, Het-1A cells showed an upregulation in pAKT expression with UBM-ECM and eECM treatment at 6 and 24 h (FIG. 26B). PI3K-Akt-mTOR has been shown to be upregulated in many cancers, including the progression from BE to EAC. PI3K-Akt is an EAC signaling pathway, but its activation is also shown to be vital in wound healing processes in non-malignant cells. The opposite regulation of phosphorylated AKT in Het-1A and OE33 cells in response to the same ECM hydrogel stimuli would be favorable for a therapy promoting tissue reconstruction in a setting of previous cancer FIG. 20. UBM Soluble Fraction induces caspase-3-mediated apoptosis in primary glioma cells. Normal primary human foreskin fibroblasts or primary human glioma cells (0319) were treated with 3 mg/ml UBM soluble fraction (UBM-SF) for 12 hr. Phase contrast microscopy shows that in contrast to the normal human fibroblasts, primary human glioma cells undergo rapid apoptosis after treatment with UBM-SF. Evaluation of the cell culture using a Nucview caspase-3 substrate at 12 hours (hr) shows that caspase-3 is mediating the apoptotic effect of UBM-SF.
Figure 19B:
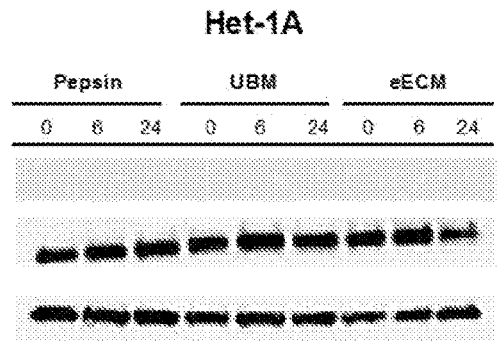

Pepsin solubilized UBM and eECM decreased phosphorylated AKT protein expression in OE33 cells and increased phosphorylated AKT in Het-1A cells. Western immunoblot was performed on the OE33 and Het-1A lysates for pAKT, a key upstream regulator of proliferation, cell cycle, and metabolism. OE33 cells and Het-1A cells showed no change in pAKT in the pepsin control. OE33 cells showed a downregulation in pAKT expression with UBM treatment at 24 h, and a downregulation in pAKT expression with eECM treatment at 6 and 24 h (FIG. 19A). In contrast, Het-1A cells showed an upregulation in pAKT expression with UBM and eECM treatment at 6 and 24 h (FIG. 19B).

PI3K-Akt-mTOR has been shown to be upregulated in many cancers, including the progression from BE to EAC. PI3K-Akt is an EAC signaling pathway, but its activation is also shown to be vital in wound healing processes in non-malignant cells. The opposite regulation of phosphorylated AKT in Het-1A and OE33 cells in response to the same ECM hydrogel stimuli is a favorable outcome for a therapy promoting tissue reconstruction in a setting of previous cancer.

Figure 20:
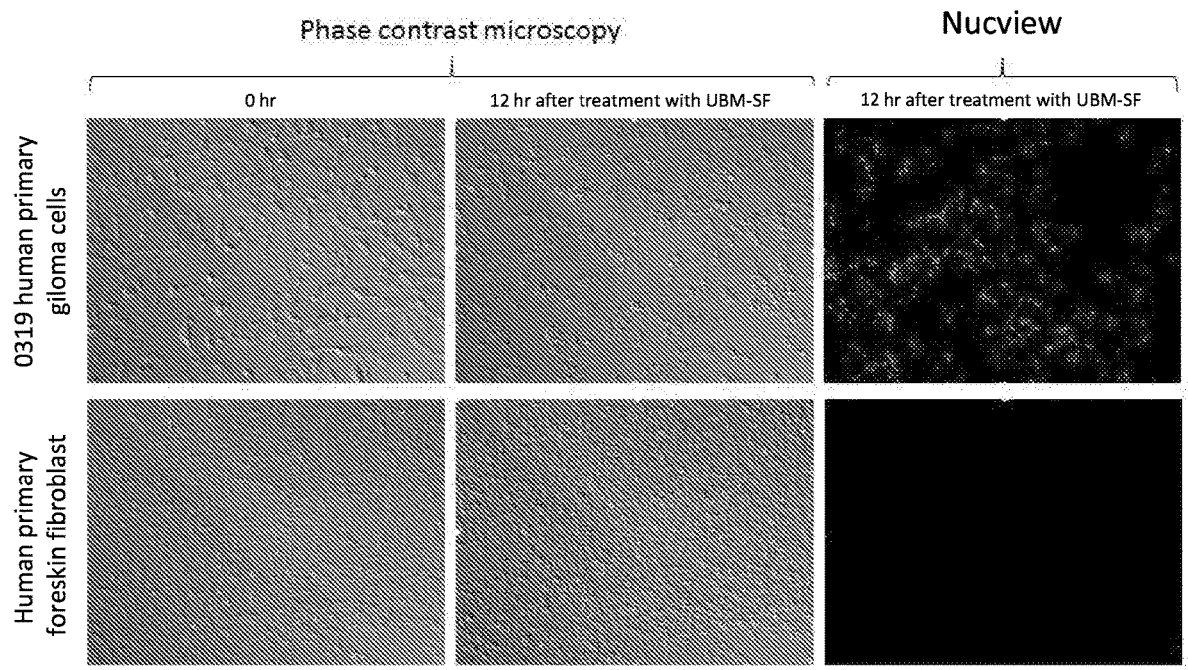
Figure 21:
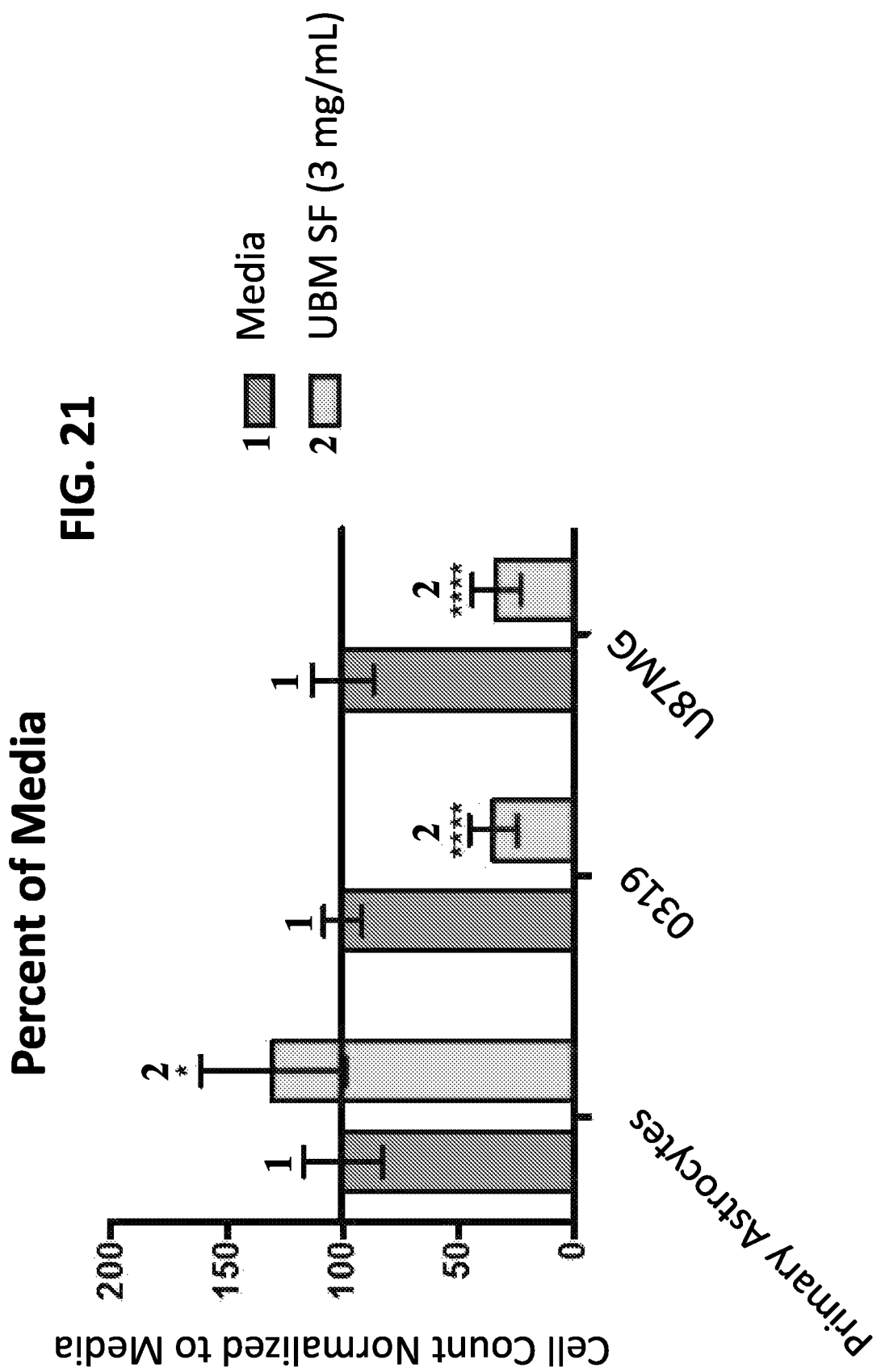
FIG. 21. UBM Soluble Fraction increases the proliferation rate of normal primary human astrocytes. Primary human astrocytes, primary human glioma cells (0319), or an immortalized glioma cell line (U87MG) were treated with or without 3 mg/ml UBM soluble fraction (UBM-SF) for 24 r. The data show that UBM-SF increased the proliferation of normal human primary astrocytes, but significantly decreased the number of glioma cells.

UBM-SF caused glioma cell death through caspase-3 mediated apoptosis. Time-lapse video was acquired by imaging cells every 20 minutes for 12 hours. Glioma cells (0319) given UBM-SF underwent cell death while human foreskin fibroblasts continued to grow and divide. Addition of the NUCVIEW™ reagent, specifically cleaved by caspase-3, to the wells revealed that the glioma cells underwent caspase-3 mediated apoptosis, whereas no apoptosis is observed in the fibroblast cells (FIG. 20).

Figure 22:
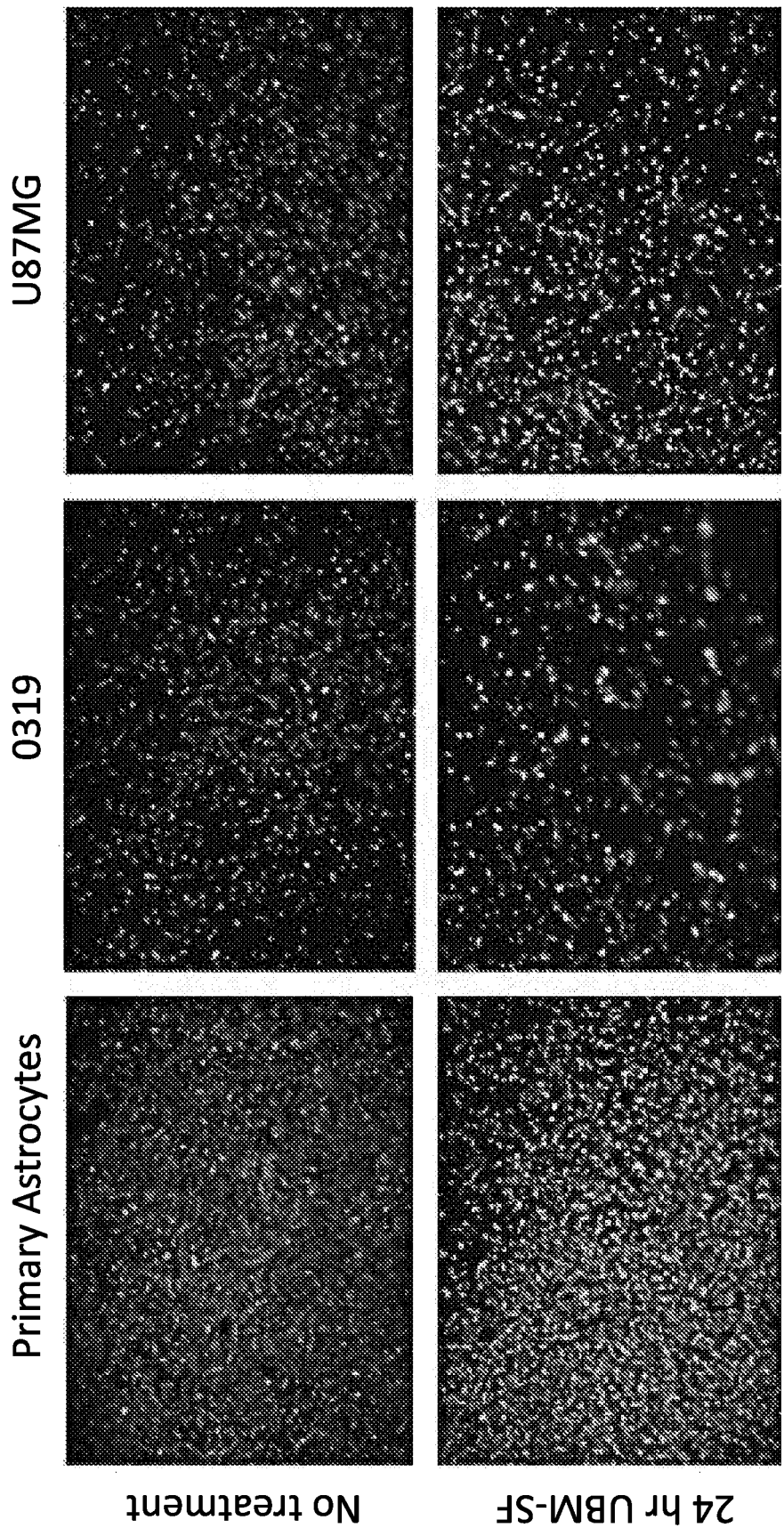
FIG. 22. UBM Soluble Fraction is toxic to primary glioma cells but not primary human astrocytes. Primary human astrocytes, primary human glioma cells (0319), or an immortalized glioma cell line (U87MG) were treated with or without 3 mg/ml UBM soluble fraction (UBM-SF) for 24 r.

UBM-SF killed primary human gliomas and an established glioma cell line while supporting primary astrocyte growth. Cell viability was measured by a live/dead fluorescent assay and then quantified using Cell Profiler. Primary astrocytes remained viable while a primary human glioma cell type (0319) and an established glioma cell line (U-87MG) underwent cell death when treated with UBM-SF (FIG. 22A). This observation was quantified by Cell Profiler and primary astrocytes treated with UBM-SF proliferated significantly more than media control in 24 hours whereas populations of glioma cells were significantly decreased (FIG. 22B).

UBM-SF decreased lung and breast cancer cell viability and supports normal breast epithelial cells. Lung cancer and HeLa cells showed dose-dependent decreased viability when treated with UBM-SF while normal breast epithelial cells were largely unchanged. Thus, mammalian ECM (specifically the saline-extracted fraction of lyophilized UBM) possessed oncolytic properties across many cancer cell types (FIG. 23).

UBM-SF showed a therapeutic window for targeting glioma cells, unlike temozolomide (TMZ). When non-neoplastic and glioma wells were treated with the alkylating agent, TMZ, the current gold standard of therapy for patients with grade IV glioma, all cells were seen to die at similar rates in a dose-dependent manner. However, when these same cells were treated with increasing concentrations of UBM-SF, the non-neoplastic cells always survived in greater numbers than the glioma cells, thereby exhibiting the presence of a therapeutic window for UBM-SF (FIG. 24).

Multiple sub-fractions of UBM-SF retained anti-glioma properties. UBM-SF was sub-divided into sub-fractions by size exclusion chromatography using Sepharose CL-6B. Fractions were pooled and used to treat microglia cells (CHME5), primary human foreskin fibroblasts (HFF), one high grade glioma cell type (0319) and one low grade glioma cell type (1119). Multiple pooled fractions retained anti-glioma properties from the parent solution while also supporting the non-neoplastic cells (FIG. 25).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for reducing the proliferation of a tumor cell, increasing apoptosis of a tumor cell, and/or decreasing migration of a tumor cell, comprising
contacting the tumor cell with an effective amount of a solubilized extracellular matrix (ECM) hydrogel or soluble fraction thereof, thereby reducing the proliferation of the tumor cell, increasing apoptosis of the tumor cell, and/or decreasing migration of the tumor cell.

2. The method of claim 1, wherein the soluble faction is produced by
    a. partially or completely digesting decellularized extracellular matrix (ECM) from a tissue to produce digested ECM material;
    b. neutralizing the digested ECM material to a pH of 7.2 to about 7.8 to produce neutralized, digested ECM material;
    c. gelling the neutralized, digested ECM material at a temperature at or above 37° C. to produced gelled ECM material;
    d. centrifuging the gelled ECM material to produce a pellet and a supernatant; and
    e. isolating the supernatant which is the soluble fraction of the solubilized ECM hydrogel.

3. The method of claim 2, wherein the decellularized ECM is not dialyzed prior to partially or completely digesting the decellularized ECM.

4. The method of claim 2, wherein the extracellular matrix is partially or completely digested with an acid protease in an acidic solution.

5. The method of claim 1, wherein the tumor cell is in vivo.

6. The method of claim 1, wherein the tumor cell is in vitro.

7. The method of claim 1, wherein the tumor cell is a glioma cell, a breast cancer cell or a lung cancer cell.

8. The method of claim 1, wherein the ECM is urinary bladder ECM.

9. A method for reducing the proliferation of a tumor cell, increasing apoptosis of a tumor cell, and/or decreasing migration of a tumor cell, comprising
contacting the tumor cell with an effective amount of a solubilized extracellular matrix (ECM) hydrogel or soluble fraction thereof, thereby reducing the proliferation of the tumor cell, increasing apoptosis of the tumor cell, and/or decreasing migration of the tumor cell, wherein the extracellular matrix is esophageal ECM and wherein the tumor cell is an esophageal adenocarcinoma cell.

10. A method of treating a subject with a tumor, comprising
selecting the subject with the tumor; and
administering to the subject a therapeutically effective amount of a pharmaceutical composition comprising a solubilized extracellular matrix (ECM) hydrogel or soluble fraction thereof and a pharmaceutically acceptable carrier,
thereby treating the tumor in the subject.

11. The method of claim 9, wherein the soluble fraction is produced by
    a. partially or completely digesting decellularized extracellular matrix (ECM) from a tissue to produce digested ECM material;
    b. neutralizing the digested ECM material to a pH of 7.2 to about 7.8 to produce neutralized, digested ECM material;
    c. gelling the neutralized, digested ECM material at a temperature at or above 37° C. to produce a gelled ECM material;
    d. centrifuging the gelled ECM material to produce a pellet and a supernatant; and
    e. isolating the supernatant which is the soluble fraction of the solubilized ECM hydrogel.

12. The method of claim 11, wherein the decelluarized ECM is not dialyzed prior to partially or completely digesting the decellularized ECM.

13. The method of claim 11, wherein the extracellular matrix is partially or completely digested with an acid protease in an acidic solution.

14. The method of claim 10, wherein the tumor is a solid tumor.

15. The method of claim 14, wherein the solid tumor is a glioma, lung cancer or a breast cancer.

16. The method of claim 15, wherein the tumor is a glioma, and wherein the glioma is an ependymoma, astrocytoma, oligodendroglioma, brainstem glioma, optic nerve glioma, or a mixed glioma.

17. The method of claim 10, wherein the ECM is urinary bladder ECM.

18. The method of claim 10, wherein the solubilized extracellular matrix (ECM) hydrogel or soluble fraction thereof is administered locally to the tumor.

19. The method of claim 10, wherein treating the tumor comprises decreasing tumor volume; decreasing the number or size of metastases; or lessening a symptom of the tumor.

20. The method of claim 10, further comprising surgically resecting the tumor.

21. The method of claim 10, further comprising administering to the subject a therapeutically effective amount of an additional chemotherapeutic agent to the subject.

22. A method of treating a subject with a tumor, comprising
selecting the subject with the tumor; and
administering to the subject a therapeutically effective amount of a pharmaceutical composition comprising a solubilized extracellular matrix (ECM) hydrogel or soluble fraction thereof and a pharmaceutically acceptable carrier,
thereby treating the tumor in the subject, wherein the ECM is esophageal ECM and wherein the tumor is an esophageal adenocarcinoma.

* * * * *

UNITED STATES PATENT AND TRADEMARK OFFICE
CERTIFICATE OF CORRECTION

PATENT NO. : 11,291,688 B2
APPLICATION NO. : 16/490056
DATED : April 5, 2022
INVENTOR(S) : Badylak et al.

It is certified that error appears in the above-identified patent and that said Letters Patent is hereby corrected as shown below:

In the Claims

Claim 2, Column 29, beginning at Line 23, "temperature at or above 37° C. to produced gelled ECM" should read -- temperature at or above 37° C. to produce gelled ECM --

Signed and Sealed this
Twenty-fifth Day of October, 2022

Katherine Kelly Vidal
*Director of the United States Patent and Trademark Office*